United States Patent [19]
Kikuchi et al.

[11] Patent Number: 5,408,263
[45] Date of Patent: Apr. 18, 1995

[54] ELECTRONIC ENDOSCOPE APPARATUS

[75] Inventors: Kenichi Kikuchi; Akira Watanabe, both of Hachioji; Masaki Terakubo, Sagamihara; Takehiro Nakagawa; Yasuo Komatsu, both of Hachioji, all of Japan

[73] Assignee: Olympus Optical Co., Ltd., Tokyo, Japan

[21] Appl. No.: 76,771

[22] Filed: Jun. 15, 1993

[30] Foreign Application Priority Data

Jun. 16, 1992 [JP] Japan .................................. 4-156949

[51] Int. Cl.$^6$ .............................. A61B 1/04; A61B 1/06
[52] U.S. Cl. ...................................... 348/68; 348/223; 348/229; 348/370
[58] Field of Search .................. 348/68, 69, 70, 72, 348/65, 45, 229, 370, 371, 222, 223; H04N 7/18

[56] References Cited

U.S. PATENT DOCUMENTS

| | | | |
|---|---|---|---|
| 4,495,520 | 1/1985 | Kravitz et al. | 348/229 |
| 4,884,133 | 11/1989 | Kanno | 348/72 |
| 5,065,248 | 11/1991 | Homma | 348/229 |
| 5,315,383 | 5/1994 | Yabe | 348/68 |

FOREIGN PATENT DOCUMENTS

| | | |
|---|---|---|
| 1-17621 | of 0000 | Japan . |
| 1-85631 | of 0000 | Japan . |
| 63-155984 | of 0000 | Japan . |
| 63-240827 | of 0000 | Japan . |

*Primary Examiner*—Howard W. Britton
*Attorney, Agent, or Firm*—Armstrong, Westerman, Hattori, McLeland & Naughton

[57] ABSTRACT

An electronic endoscope apparatus has an arrangement that its discrimination circuit discriminates the type or the operational state of the light source in accordance with a discrimination signal transmitted from a discrimination signal generator, and in accordance with the result of the discrimination, the processing operation to be performed by its video signal processing circuit is changed over to correspond to the difference in the type or the operational state of the light source. The video signal processing circuit performs a proper signal processing operation to correspond to the difference in the type of the light source to prevent deterioration in the image quality. The electronic endoscope apparatus is structured so that a different type light source can be adaptably connected to it.

76 Claims, 58 Drawing Sheets

TO DISCRIMINATION CIRCUIT

TO DISCRIMINATION CIRCUIT

FIG.36
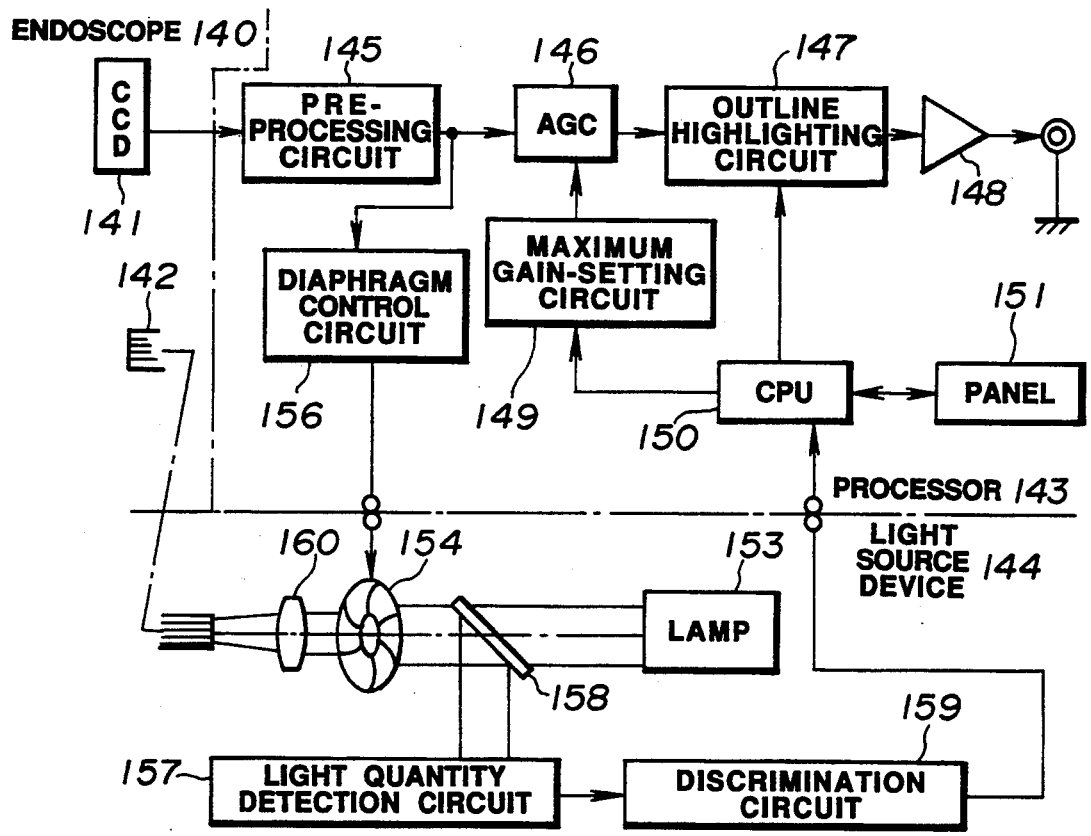
FIG.37
| | STATE<br>SET PANEL | NORMAL STATE | IN A SMALL LIGHT QUANTITY STATE |
|---|---|---|---|
| OUTLINE HIGHLIGHT LEVEL | "L" | 3dB | 0dB |
| | "M" | 6dB | 3dB |
| | "H" | 9dB | 6dB |
| MAXIMUM GAIN OF AGC | | 9dB | 18dB |
FIG.38
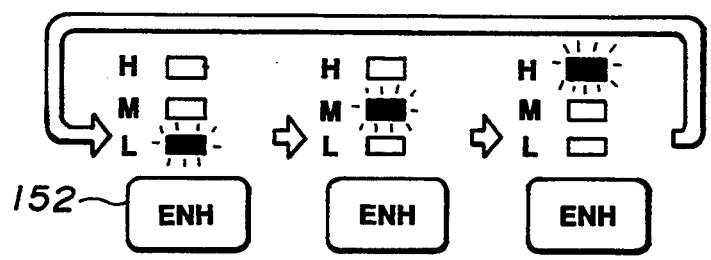

FIG. 41a

| SETTING OF PANEL | INSTRUCTED VALUE OF COLOR SIGNAL R | INSTRUCTED VALUE OF COLOR SIGNAL R |
|---|---|---|
| +5 | 28 | 28 |
| +4 | 26 | 26 |
| +3 | 24 | 24 |
| +2 | 22 | 22 |
| +1 | 20 | 20 |
| 0 | 18 | 18 |
| -1 | 16 | 16 |
| -2 | 14 | 14 |
| -3 | 12 | 12 |
| -4 | 10 | 10 |
| -5 | 8 | 8 |

FIG. 41b

| SETTING OF PANEL | INSTRUCTED VALUE OF COLOR SIGNAL B | INSTRUCTED VALUE OF COLOR SIGNAL B |
|---|---|---|
| +5 | 22 | 32 |
| +4 | 20 | 30 |
| +3 | 18 | 28 |
| +2 | 16 | 26 |
| +1 | 14 | 24 |
| 0 | 12 | 22 |
| -1 | 10 | 20 |
| -2 | 8 | 18 |
| -3 | 6 | 16 |
| -4 | 4 | 14 |
| -5 | 2 | 12 |

ROTATIONAL PLANE OF
ROTATIVE FILTER

REGION IN WHICH IRRADIATION LIGHT LACKS

CHILD IMAGE PLANE (KINETIC IMAGE)

PARENT IMAGE PLANE (STILL IMAGE)

THRESHOLD VALUE

EFFECTIVE IMAGE PLANE

FIG.76a
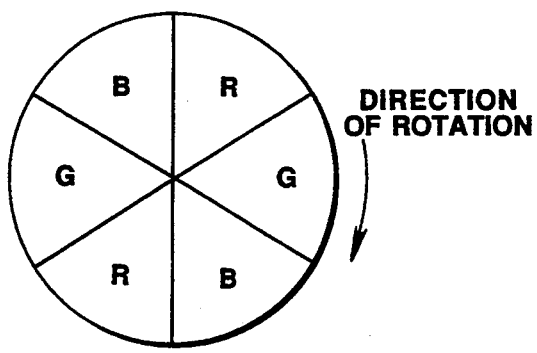
FIG.76b
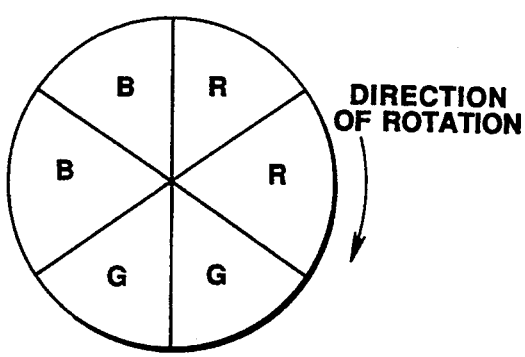
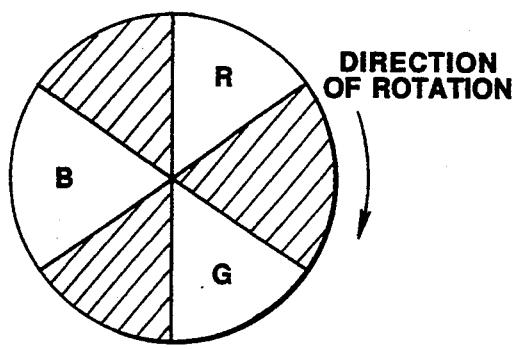
FIG.76c
FIG.77a
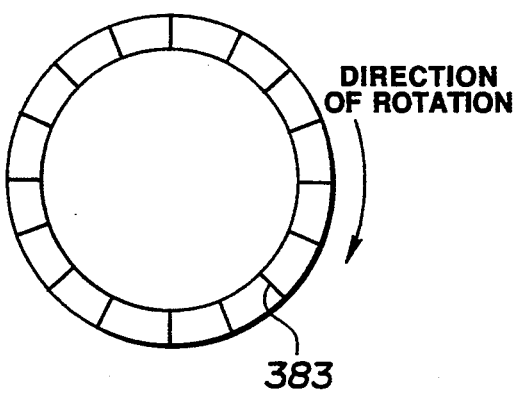
FIG.77b
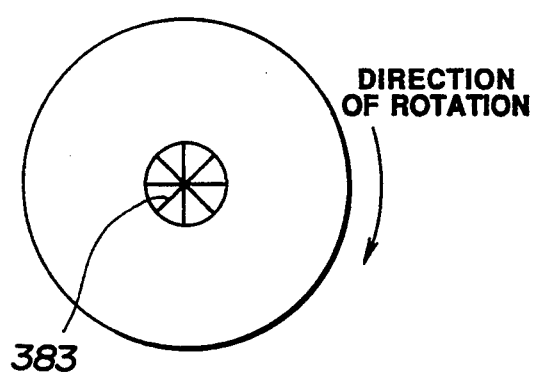

O : ODD-NUMBER FIELD
E : EVEN-NUMBER FIELD

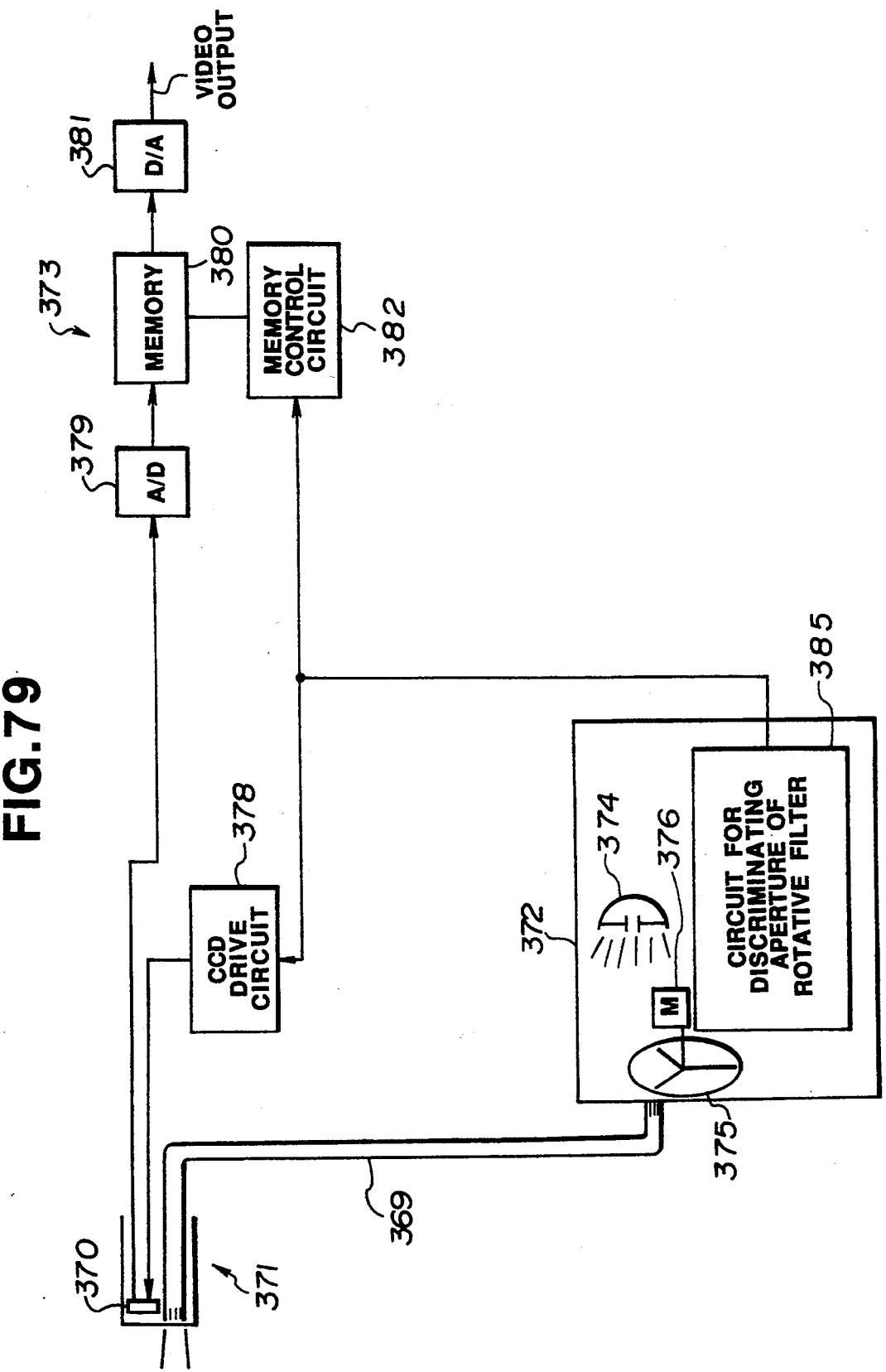

DIRECTION OF ROTATION

DIRECTION OF ROTATION

DIRECTION OF ROTATION

BAR CODE

DIRECTION OF ROTATION

BAR CODE

O : ODD-NUMBER FIELD
E : EVEN-NUMBER FIELD

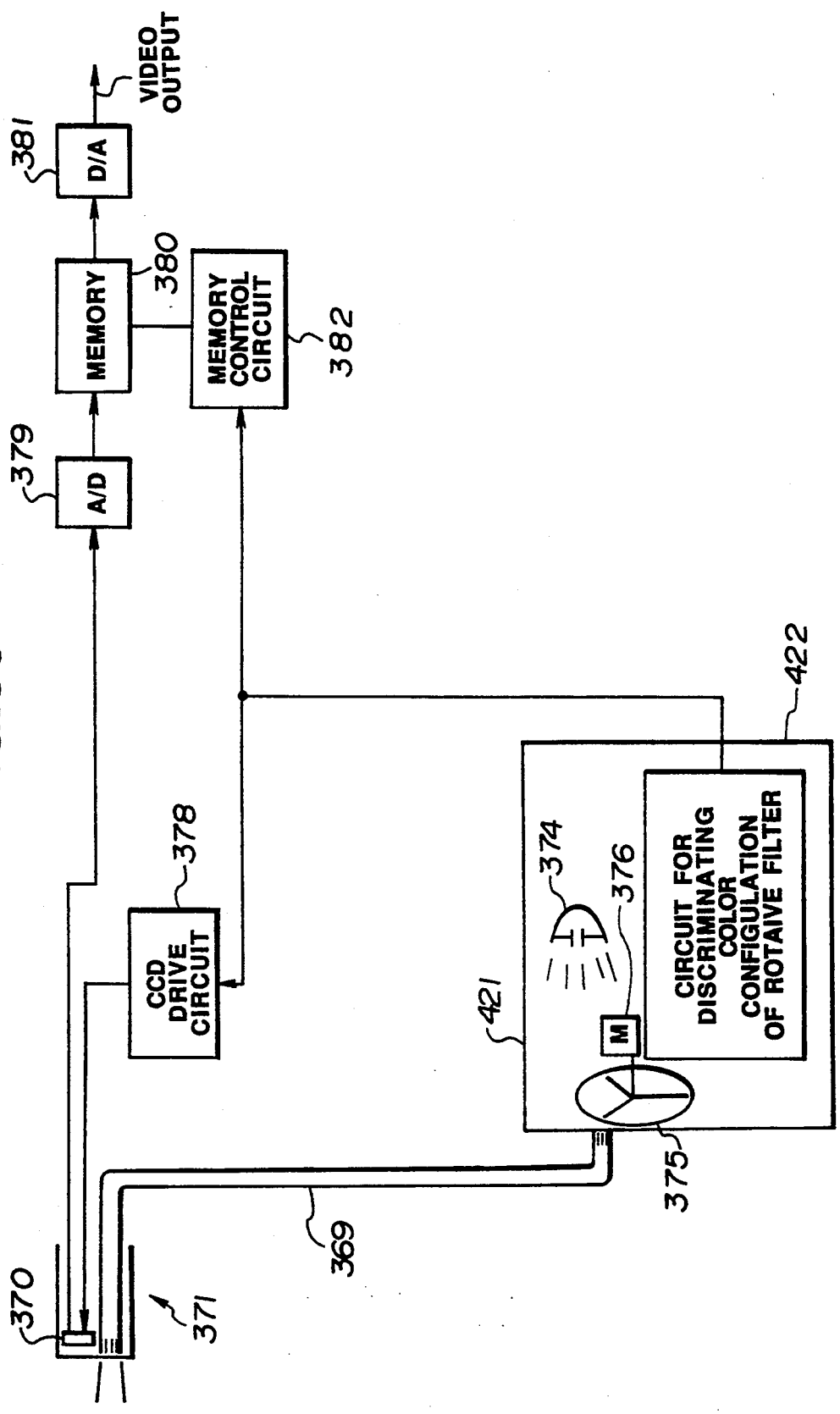

FIG. 86a
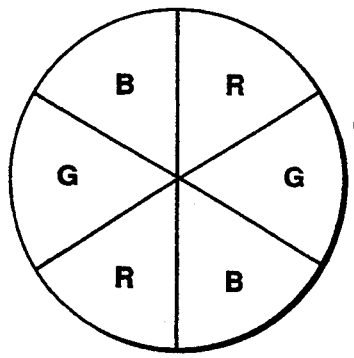
FIG. 86b
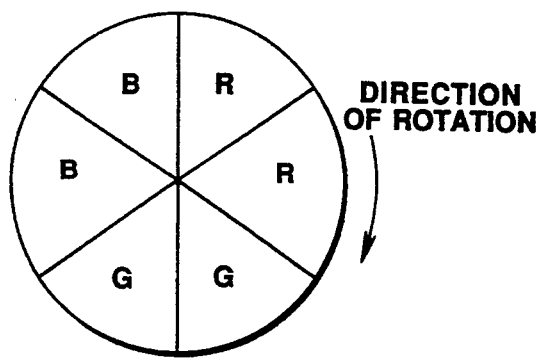
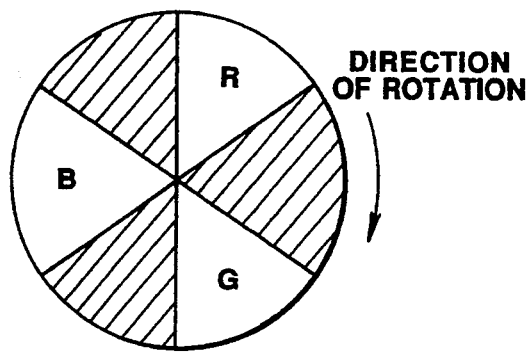
FIG. 86c
FIG. 87a
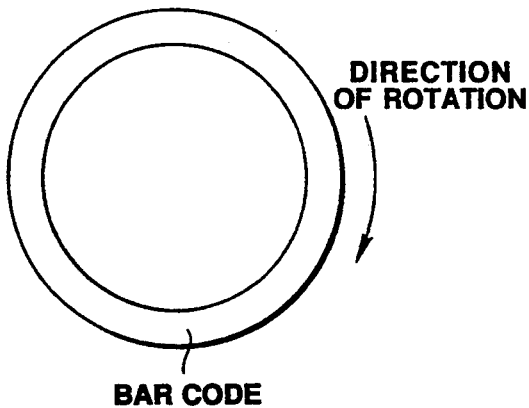
FIG. 87b
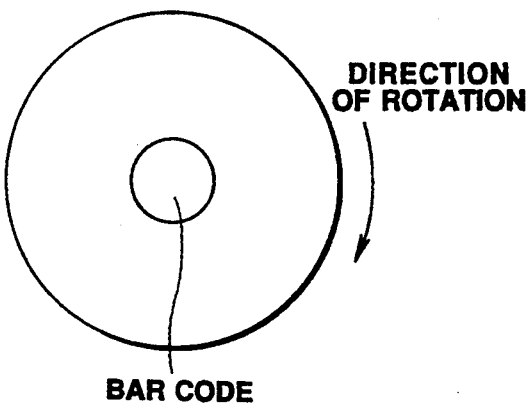

O : ODD-NUMBER FIELD
E : EVEN-NUMBER FIELD

O : ODD-NUMBER FIELD
E : EVEN-NUMBER FIELD

ELECTRONIC ENDOSCOPE APPARATUS

BACKGROUND OF THE INVENTION

1. Field of the Invention

The present invention relates to an electronic endoscope apparatus to be inserted into a subject for inspection to enable its inside to be observed.

2. Related Art And Prior Art Statement

Endoscopes have been widely used, each of which comprises an elongated insertion portion to be inserted into the coelom to observe the internal organ in the coelom, and which uses a curing tool inserted into a channel for the curing tool to perform a variety of treatments, if necessary.

Also industrial endoscopes have been widely used for the purpose of observing and inspecting internal flaws or corrosion occurring in boilers, gas turbine engines, pipes in chemical plants and the bodies of automobiles.

Further, a variety of electronic endoscopes have been used each of which has an image pickup means comprising a solid-state image sensing device, such as a charge-coupled-device (CCD).

FIG. 1 illustrates an example of the structure of an electronic endoscope apparatus which uses an electronic endoscope 81. The electronic endoscope 81 has an elongated and, for example, flexible insertion portion 82. Further, a control portion 83 having a large diameter is connected to the trailing end of the insertion portion 82. A flexible cable 84 is extended sidewards from the trailing end of the control portion 83, the cable 84 having a connector 85 in the leading portion thereof. The electronic endoscope 81 is connected to a video processor 86 via the connector 85, the video processor 86 including a light source device serving as an irradiation-light generating means and a signal processing circuit. Further, a monitor 87 is connected to the video processor 86.

The insertion portion 82 has, in the leading portion thereof, a hard leading portion 89 and a warp-enabled portion 90 which can be warped and which is disposed sequentially, the warp-enabled portion 90 being disposed adjacently to the trailing portion of the leading portion 89. Further, the endoscope 81 has an arrangement that a warp-control-portion knob 91 disposed in the control portion 83 can be rotated so that the warp-enabled portion 90 is warped horizontally or vertically. The control portion 83 has an insertion port 92 communicated with a channel (omitted from illustration) for a curing tool disposed in the insertion portion 82.

As shown in FIG. 2, a light guide 94 for transmitting irradiation light is arranged to penetrate the insertion portion 82 of the electronic endoscope 81. The leading surface of the light guide 94 is disposed in a leading portion 89 of the insertion portion 82 so that irradiation light can be emitted from the leading portion 89. The light-incidental end of the light guide 94 is passed through the universal cord 84 and connected to the connector 85. The leading portion 89 has an objective lens system 95 fastened thereto. A solid-state image sensing device 96, such as CCD, is disposed at a position at which an image is formed by the objective lens system 95. The solid-state image sensing device 96 has sensitivity in a wide range from the ultraviolet region to the infrared region including a visible region. Signal lines 71 and 72 are connected to the solid-state image sensing device 96, the signal lines 71 and 72 being passed through the insertion portion 82 and the universal cord 84 as to be connected to the connector 85.

On the other hand, a lamp 73 serving as an irradiation light source for emitting light in a wide band zone from ultraviolet rays to infrared rays is disposed in the video processor 86. The lamp 73 may be an ordinary xenon lamp, a strobe lamp or a halogen lamp. The xenon lamp, the strobe lamp and the halogen lamp are able to emit ultraviolet rays and infrared rays by a large quantity as well as visible rays. The lamp 73 is supplied with electric power from a light source portion 77. Light emitted from the lamp 73 is made incident upon the light-incidental end of the light guide 94 and guided to the leading portion 89 via the light guide 94. As a result, light is emitted from the leading portion 89 so that the portion to be observed is irradiated with light.

Irradiation light is then returned by the portion to be observed, and it is imaged on the solid-state image sensing device 96 by the objective lens system 95 so that returned light is photoelectrically converted. The solid-state image sensing device 96 is, via the signal line 71, applied with drive pulses from a driver circuit 70 disposed in the video processor 86. A video signal is read from the solid-state image sensing device 96 in response to the drive pulse to transfer the video signal.

The video signal read from the solid-state image sensing device 96 is, via the signal line 72, supplied to a pre-amplifier 74 disposed in the video processor 86 or in the electronic endoscope 81. The video signal amplified by the pre-amplifier 74 is supplied to a processing circuit 75 to be subjected to signal processes, such as a γ-correction process and a white balance process. As a result, the video signal is transmitted as R, G and B signals and as well as supplied to an encoder 76. The encoder 76 subjects the R, G and B signals to conversion processes to transmit an NTSC composite signal.

The white balance operation is so controlled that, if a white subject is imaged for example, the values of the transmitted R, G and B signals are the same.

The R, G and B signals or the NTSC composite signal is supplied to a color monitor 87 so that the observed portion is color-displayed by the color monitor 87.

It can be considered that the foregoing conventional example encounters the following problems in a case where the type of the light source serving as information about the irradiation light generating means, for example, the type of the lamp, is changed. The lamp for the endoscope is typified by the foregoing xenon lamp and the halogen lamp. The xenon (Xe) lamp and the halogen lamp have different radiation energy distributions and also exhibits a difference in the color temperature of about 2000K. If the color temperature is considerably different by the foregoing degree, the white balance adjustment performed to adjust the color reproduction is insufficient to realize satisfactory reproductions of the other colors. In general, the xenon lamp is used as a usual lamp and the halogen lamp is used as an emergency lamp.

What is worse, a signal processing method must be varied between different irradiation (imaging) methods, which are the types of the light sources serving as information about the irradiation-light generating means, for example, between a plane sequential method and a single-plate color method (hereinafter sometimes expressed as a "simultaneous method"). The conventional structure cannot cope with the foregoing problem.

Since medical endoscopes among the endoscopes for use in a variety of fields are so used that the inner wall of the body is the subject of imaging, the reproduced color has a feature that red shades are made relatively thick. Therefore, if the distance from the leading portion of the endoscope to the subject is elongated, a major portion of irradiation light emitted from the light guide is applied to the subject after light has been reflected by the inner wall. Hence, red shades are intensified excessively in the colors of the imaged subject. That is, the image is affected by so-called secondary reflected light.

Some light source devices have a light-quantity adjustment means, such as a diaphragm, for the purpose of obtaining a proper light quantity. The position of the diaphragm, which is the operational state of the light source, or a deflection between the diaphragm and the optical axis sometimes varies the color of irradiation light emitted from the lamp. Therefore, there arises a problem in that the diaphragm is changed due to the brightness of the subject and the change in the brightness changes the overall color even if the white balance adjustment is performed.

An electronic endoscope adapted to the plane sequential method has an arrangement that a color-decomposing rotative filter is disposed in the light source. If the color-decomposing rotative filter has been changed, the color reproducibility of the obtained image depends upon scatter of the spectrum characteristics of the filter. The conventional apparatus has an arrangement that the scatter of the color-decomposing filter is adjusted by only the white balance adjustment. Therefore, the colors, which are critical for making a diagnosis with the endoscope, have not been collected satisfactorily.

There has been a light source device of a type having three types of irradiation modes, that is, a plane sequential method/a single-plate color method/an optical-type-endoscope so that the mode is changed over in accordance with the type of the endoscope and that of the processor that are combined at the time of using. In the case where a processor adaptable to both plane sequential method and the simultaneously method is combined with a light source device at the time of use, a system is desired that is able to efficiently and correctly set each device and exhibits excellent operational facility.

In an electronic endoscope apparatus capable of processing image signals respectively obtained by the plane sequential method and the simultaneous method, the signals respectively obtained by the two methods have different forms. Therefore, the signal process, for example, a white balance processing operation and the like must be changed to be adaptable to the foregoing methods.

Further, the wave detection method for generating a signal for controlling the gain must be changed in an AGC (Automatic Gain Control) provided for the processor portion to be adaptable to the different modes, that is, the plane sequential mode and the simultaneous mode, which is one of the operational states of the light source.

In the conventional electronic endoscope apparatus, drive of the CCD thereof cannot be changed to be adaptable to a state whether the light source is the light source for the plane sequential irradiation light or the light source for the white light irradiation. Therefore, the resolution has deteriorated or the dynamic range has fallen undesirably.

A light source device solely adaptable to the plane sequential method encounters an undesirable color mixture if the rotational speed of a rotative filter for separating irradiation light into a plurality of different wavelength regions is changed. If the numerical aperture of an optical filter disposed in the rotative filter is changed, light is undesirably introduced and a flicker and/or a color mixture takes place. If the sequential order or the configuration of colors of the optical filter is changed, an undesirable color mixture takes place. Each of the foregoing facts is one of the operational states of the light source.

Some of the electronic endoscope apparatuses use special light, such as infrared rays, for the purpose of observing, for example, blood flows as well as performing the imaging operation using plane sequential irradiation light and white irradiation light.

In the case where the special-light observation is performed, the white balance realized in a usual observation operation has been insufficient to always obtain color tone that is suitable for the observation.

If the xenon lamp, which is the usual lamp of the light source device, is burned out and, accordingly, changing over to the halogen lamp serving as the emergency lamp is performed, the signal processing operation of the processor has not been changed. Therefore, if changing over to the emergency lamp is performed during an inspection, color is rapidly changed. Therefore, the observation rapidly becomes difficult to be performed, causing a problem to rise at the time of performing the inspection.

The lamp serving as the emergency lamp emits light by a quantity smaller than that emitted by the diagnosis irradiation xenon lamp. Therefore, there arises a problem in that the observed image is darkened when the emergency lamp is used.

Further, setting, in which the white balance arranged with the xenon lamp is as it is used, has been employed at the time of performing the process although the lamp, which is being lit, is the halogen lamp. Therefore, the obtained image is excessively reddened.

Since a precise inspection cannot be performed under the emergency lamp as described above, only removal of the endoscope has been performed usually in order to secure safety of a patient.

In order to obtain a further excellent image, a countermeasure must be taken against the reduction in the light quantity of the lamp due to an aged deterioration as well as that against the life and a failure of the lamp. For example, the light quantity of a xenon lamp for use in the light source device is in inverse proportion to the time in which the xenon lamp is lit. Therefore, the light quantity of the light source becomes changed by a quantity of two times or more before and after the lamp is changed.

Hitherto, the automatic light regulation loop characteristics of irradiation light has been set while making a lamp which has been lit for tens of hours to be a standard. Therefore, the light regulation loop gain is undesirably set to a low level due to lack of the light quantity immediately before a new lamp is installed. As a result, the response is delayed excessively. On the other hand, the light regulation loop gain is raised excessively due to an excessively large light quantity immediately after the change of the lamp. Therefore, tendency of hunting rises.

When the light regulation operation is performed, the relationship between the diaphragm blade and the optical path, that is, the degree of the diaphragm (the position of the diaphragm) sometimes changes the color of irradiation light. Therefore, there arises a problem that the color tone is changed.

What is worse, the relationship between the reduction in the light quantity of the lamp and the AGC (Automatic Gain Control) of the processor raises the following problem.

The processor of an electronic endoscope apparatus usually performs the AGC in order to maintain a signal obtained by performing imaging with a CCD at a predetermined level. However, if the AGC is performed in a case where the light quantity of the lamp has been reduced, noise becomes conspicuous. In particular, the abnormality of the color tone becomes conspicuous when the usual lamp has been changed over to the emergency lamp.

As for the operation of the AGC, another problem arises due to the relationship between it and the diaphragm serving as a light quantity adjustment means for the light source.

There has been available an apparatus for displaying the image of an endoscope of a type which simultaneously displays a parent image plane and a child image plane. The foregoing apparatus usually displays a kinetic image by only the parent image plane thereof. However, it is convenient for an observer to also display the kinetic image in a case where a still image is displayed. Accordingly, an apparatus has been suggested which displays a kinetic image on either image plane thereof and which displays a still image on the residual image plane.

In the foregoing apparatus, when freezing is performed in a CCD shutter mode, the iris (the blade) of the diaphragm provided for the light source device is operated in order to give the CCD a proper exposure light quantity. As a result, the diaphragm is opened. However, if proper brightness cannot be obtained due to a too long observation distance, flash irradiation has been performed at the time of freezing. When, for example, the child image plane is displaying a kinetic image at this time, the AGC reacts with the flash irradiation. Therefore, an unsightly image such as hunting is displayed.

Although the AGC acts to maintain the signal level at a predetermined level in response to light reflected by a subject, it encounters the foregoing problems depending upon the state of the diaphragm and/or that of the irradiation light source. The conventional structure has no means adaptable to each of the states of the light source device and a plurality of irradiation modes.

What is worse, the conventional electronic endoscope apparatus cannot properly control the light quantity if a light source having no light quantity adjustment means is connected in place of a light source having a function capable of automatically regulating light. In this case, a normal image cannot be obtained.

In addition, the conventional endoscope apparatus encounters a fact that its diaphragm is opened in a case where trans-illumination takes place in the light source. As a result, the light quantity cannot be controlled and the brightness of the image is undesirably saturated.

As described above, if a variety of countermeasures are not taken to be adaptable to information about the irradiation light generating means such as the type, the operational state or the function of the light source, problems of deterioration in the image quality and efficiency and the like arise.

OBJECTS AND SUMMARY OF THE INVENTION

A first object of the present invention is to provide an electronic endoscope apparatus which is capable of optimally changing a signal process for processing an image signal in accordance with information about an irradiation light generating means.

A second object of the present invention is to provide an electronic endoscope apparatus for performing a proper signal process in accordance with information about an irradiation light generating means so that deterioration in the image quality can be prevented.

A third object of the present invention is to provide an electronic endoscope apparatus which is capable of properly processing a video signal even if the type of an irradiation light generating means is different.

A fourth object of the present invention is to provide an electronic endoscope apparatus which is capable of properly processing an image signal to be adapted to change in the operational state of an irradiation light generating means even if the operational state of the irradiation light generating means has been changed.

A fifth object of the present invention is to provide an electronic endoscope apparatus which is capable of properly changing a signal process for processing an image signal even if the function possessed by an irradiation light generating means is different.

A sixth object of the present invention is to provide an electronic endoscope apparatus which is not considerably affected by secondary reflected light and which exhibits excellent color reproducibility.

A seventh object of the present invention is to provide an electronic endoscope apparatus which is always normal and which exhibits excellent color reproducibility even if the color of emitted light has been changed due to the position of a light quantity adjustment means or due to a deviation occurring between the light quantity adjustment means and the optical axis.

An eighth object of the present invention is to provide an electronic endoscope apparatus which is capable of preventing change in the color reproducibility of an image in a case where a color decomposing rotative filter of in a case where an irradiation light generating means adapted to a plane sequential irradiation .method has been changed or the rotative filter has been changed due to change of the apparatus.

A ninth object of the present invention is to provide an electronic endoscope apparatus which is capable of quickly, assuredly and adaptably setting each apparatus to be adaptable to any one of a plurality of irradiation modes of a light source.

A tenth object of the present invention is to provide an electronic endoscope apparatus which is capable of automatically changing over the method of adjusting the white balance of a signal processing means in a case where the irradiation mode of the light source has been changed over to a plane sequential mode or a simultaneous mode.

An eleventh object of the present invention is to provide an electronic endoscope apparatus which is capable of automatically changing over the wave detection method of an AGC of a signal processing means in a case where the irradiation mode of the light source has been changed over to a plane sequential mode or a simultaneous mode.

A twelfth object of the present invention is to provide an electronic endoscope apparatus which enables a normal image freed from undesired color mixture to be obtained even if the rotational speed of a rotative filter of a light source has been changed.

A thirteenth object of the present invention is to provide an electronic endoscope apparatus which enables a normal image freed from undesired color mixture to be obtained even if the numerical aperture of a rotative filter of a light source has been changed.

A fourteenth object of the present invention is to provide an electronic endoscope apparatus which enables a normal image freed from undesired color mixture to be obtained even if the color configuration or the disposition of a rotative filter of a light source has been changed.

A fifteenth object of the present invention is to provide an electronic endoscope apparatus which is capable of preventing deterioration in the resolution and maintaining the dynamic range in a case where the irradiation mode of the light source has been changed over to a plane sequential mode or a simultaneous mode.

A sixteenth object of the present invention is to provide an electronic endoscope apparatus with which a special light observation can be performed while obtaining an image, which has a color tone that can be easily recognized or which is suitable to a quantitative diagnosis.

A seventeenth object of the present invention is to provide an electronic endoscope apparatus with which an observed image having sufficient brightness and exhibiting excellent color reproducibility to be obtained for performing an observation as well as for removing the endoscope even if change over to an emergency lamp has been performed.

An eighteenth object of the present invention is to provide an electronic endoscope apparatus with which color reproducibility approximating a normal state can be obtained while preventing reddish shade image even if a usual lamp has been burned out and change over to an emergency lamp has been performed.

A nineteenth object of the present invention is to provide an electronic endoscope apparatus which is capable of maintaining stable automatic light regulation characteristics regardless of the light quantity of an irradiation light source.

A twenties object of the present invention is to provide an electronic endoscope apparatus which is capable of automatically correcting change in the color tone even if the generated color has been changed due to a diaphragm operation.

A twenty-first object of the present invention is to provide an electronic endoscope apparatus with which an optimum image quality can be realized even if the light quantity of a lamp has been reduced.

A twenty-second object of the present invention is to provide an electronic endoscope apparatus of a type simultaneously displaying a kinetic image and a still image that enables a kinetic observed image to be obtained even if an irradiation light source has performed a flash irradiation.

A twenty-third object of the present invention is to provide an electronic endoscope apparatus with which a normal image can be obtained even if a light source having no light quantity adjustment means is connected.

A twenty-fourth object of the present invention is to provide an electronic endoscope apparatus in which the brightness of an image is not saturated even at the trans-illumination.

An electronic endoscope apparatus according to the present invention comprises: irradiation light generating means for generating irradiation light for irradiating a subject; signal processing means for signal-processing an image signal obtained by imaging a subject irradiated with irradiation light; information supply means for supplying irradiation light generating means information about the irradiation light generating means; and signal processing operation changing means for changing the signal processing operation to be performed by the signal processing means in accordance with irradiation light generating means information supplied from the information supply means.

Other and further objects, features and advantages of the invention will be appear more fully from the following description.

BRIEF DESCRIPTION OF THE DRAWINGS

FIG. 4 is a block diagram which illustrates a structural example relating transmission of a light source discrimination signal;

FIG. 5 illustrates a waveform relating to the operation to be performed by the structure shown in FIG. 4;

FIG. 6 is a block diagram which illustrates a structural example of a video signal processing circuit;

FIG. 8 is a block diagram which illustrates a white balance circuit;

FIG. 9 is a block diagram which illustrates a white balance circuit which is different from that shown in FIG. 8;

FIG. 11 is an overall structural view which illustrates an electronic endoscope apparatus;

FIG. 12 is a block diagram which illustrates a structural example of a video signal processing circuit;

FIG. 13 is an overall structural view which illustrates an electronic endoscope apparatus;

FIG. 14 is a structural view which illustrates a rotative filter;

FIG. 15 is a block diagram which illustrates a structural example of a video signal processing circuit;

FIG. 16 is an explanatory view of chromaticity conversion;

FIG. 17 is a flow chart relating to change and setting of a matrix coefficient;

FIG. 18 is an overall structural view which illustrates an electronic endoscope apparatus;

FIG. 19 is a block diagram which illustrates a structural example of a video signal processing circuit;

FIG. 20 is an explanatory view of chromaticity conversion;

FIG. 21 is a graph which illustrates the characteristics of a usual lamp and an emergency lamp;

FIG. 22 is a flow chart relating to change and setting of a matrix coefficient;

FIG. 23 is an overall structural view which illustrates an electronic endoscope apparatus;

FIG. 24 is a block diagram which illustrates a structural example of a video signal processing circuit;

FIG. 25 is a block diagram which illustrates another structural example of a video signal processing circuit;

FIG. 26 is a block diagram which illustrates a still another structural example of a video signal processing circuit;

FIG. 27 is an overall structural view which illustrates an electronic endoscope apparatus;

FIG. 28 is a block diagram which illustrates a structural example of a video signal processing circuit;

FIG. 29 is an overall structural view which illustrates an electronic endoscope apparatus;

FIG. 30 is a circuit diagram of a first wave detection circuit adapted to a plane sequential imaging method;

FIG. 31 is a circuit diagram of a second wave detection circuit adapted to a simultaneous method;

FIG. 32 is a circuit diagram of a wave detection circuit adaptable to a plurality of irradiation modes;

FIG. 33 is a block diagram of a first signal processing circuit;

FIG. 34 is a block diagram of a second signal processing circuit;

FIGS. 36 to 38 relate to an eleventh embodiment;

FIG. 36 is a block diagram which illustrates the schematic structure of an electronic endoscope apparatus;

FIG. 37 is a table which shows the relationship between set AGC gain and outline highlighting level;

FIG. 38 is an explanatory view relating to change over of the outline highlighting level; FIGS. 39 to 41 relate to a twelfth embodiment;

FIG. 39 is a block diagram which illustrates the structure of an electronic endoscope apparatus;

FIG. 40 is an explanatory view relating to change over of a color-tone adjustment level;

FIG. 41a and 41b are tables showing the relationship between setting of color tone adjustment and instructed value;

FIG. 42 is a block diagram which illustrates the schematic structure of an electronic endoscope apparatus;

FIG. 43 is a block diagram which illustrates a video signal processing circuit;

FIG. 44 is a block diagram which illustrates a simultaneous signal processing circuit;

FIG. 45 is a block diagram which illustrates a plane sequential signal processing circuit;

FIG. 46 is a block diagram which illustrates the structure of a signal processing portion of an electronic endoscope apparatus;

FIG. 47 is a structural view which illustrates a light source portion;

FIG. 48 is a flow chart relating to white balance adjustment;

FIG. 50 is a block diagram which illustrates a white balance wave detection circuit when single-plate color imaging is performed;

FIG. 51 is a block diagram which illustrates a white balance wave detection circuit when plane sequential imaging is performed;

FIG. 52 is a timing chart for the circuit shown in FIG. 50;

FIG. 53 is a timing chart for the circuit shown in FIG. 51;

FIG. 54 is a structural view which illustrates an optical system of the light source portion;

FIG. 55 is an explanatory view which illustrates the relationship between the shape of a diaphragm blade and the optical axis;

FIG. 56 is a correlative view between the diaphragm aperture and each color with respect to the CCD outputs;

FIG. 57 is a flow chart for timer interruption;

FIG. 58 is a flow chart for obtaining a value for correcting the white balance;

FIG. 59 is a block diagram which illustrates a light source portion;

FIG. 60 is a flow chart for setting the white balance in a special light mode;

FIG. 61 is a block diagram which illustrates the structure of an optical system of the light source portion;

FIG. 62 is a perspective view which illustrates the structure of single-wavelength irradiation;

FIG. 63 is a perspective view which illustrates the structure of three-wavelength irradiation;

FIG. 64 is a schematic structural view which illustrates an electronic endoscope;

FIG. 65 is a structural view which illustrates a monitor image plane;

FIG. 66 illustrates a waveform of a video signal of scanning line A of the image plane shown in FIG. 65;

FIG. 67 is an explanatory view which illustrates AGC wave detection;

FIG. 68 is a circuit diagram which illustrates an example of the structure of a GCA control portion;

FIG. 69 is a circuit diagram which illustrates another example of the structure of the GCA control portion;

FIG. 70 is a schematic structural view which illustrates an electronic endoscope;

FIG. 71 is a timing chart which illustrates the operation of the apparatus shown in FIG. 70;

FIG. 73 is a schematic structural view which illustrates an electronic endoscope apparatus;

FIG. 74 is a block diagram which illustrates an example of the structure of a GCA control portion;

FIGS. 75 to 78 relate to a twenty-third embodiment;

FIG. 75 is a schematic structural view which illustrates an electronic endoscope apparatus;

FIGS. 76a, 76b and 76c are structural views which illustrates the configuration of filters of a rotative filter;

FIG. 77a and 77b are structural views relating to detection of the speed of the rotative filter;

FIGS. 79 to 82 relate to a twenty-fourth embodiment;

FIG. 79 is a schematic structural view which illustrates an electronic endoscope apparatus;

FIGS. 85 to 88 relate to a twenty-seventh embodiment;

FIG. 85 is a schematic structural view which illustrates an electronic endoscope apparatus;

FIG. 86a, 86b and 86d are structural views which illustrates the color configuration in the rotative filter;

FIG. 87a and 87b are structural views relating to detection of the color configuration of the rotative filter;

FIGS. 89 to 92 relate to a twenty-eighth embodiment;

FIG. 89 is a schematic structural view which illustrates an electronic endoscope apparatus having no rotative filter;

FIG. 90 is a schematic structural view which illustrates an electronic endoscope apparatus having the rotative filter;

FIG. 91 is a structural view which illustrates the rotative filter; and

DETAILED DESCRIPTION OF THE PREFERRED EMBODIMENTS

Preferred embodiments of the present invention will now be described with reference to the drawings.

Figure 3:
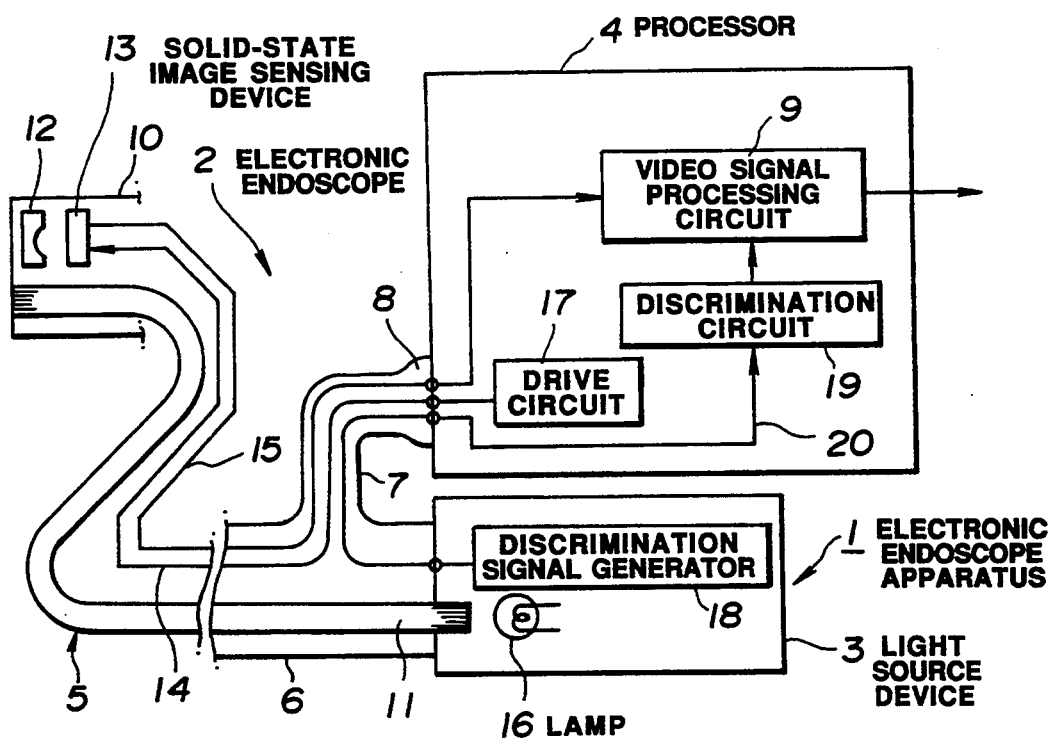
FIGS. 3 to 6 are overall structural views which illustrate an electronic endoscope apparatus according to a first embodiment.

An example of the structure of an electronic endoscope apparatus according to a first embodiment of the present invention is shown in FIG. 3. An electronic endoscope apparatus 1 shown in FIG. 3 comprises an electronic endoscope 2, a light source device 3 serving as an irradiation light generating means, a processor 4 serving as a signal processing means and a monitor (omitted from illustration).

The electronic endoscope 2 has an elongated and, for example, flexible insertion portion 5. Further, a control portion 6 having a large diameter is connected to the trailing end of the insertion portion 5. A flexible cable 7 is extended sidewards from the control portion 6, the cable 7 having a connector 8 in the leading portion thereof. The electronic endoscope 2 is connected to the light source device 3. Further, the electronic endoscope 2 is connected to the video processor 4 which includes a video signal processing circuit 9. The endoscope and the cable shown in FIG. 3 schematically illustrate the foregoing state.

Further, the foregoing monitor is connected to the video signal processing circuit 9 of the processor 4. Also a device for recording images can be connected to the video signal processing circuit 9.

The insertion portion 5 has, in the leading portion thereof, a hard leading portion 10 and a warp-enabled portion (omitted from illustration) which can be warped and which is disposed adjacently to the trailing portion of the leading portion 10. Further, the endoscope 2 has an arrangement that a warp-control-portion knob (omitted from illustration) disposed in the control portion 6 can be rotated so that the warp-enabled portion is warped horizontally or vertically.

As shown in FIG. 3, a light guide 11 for transmitting irradiation light is arranged to penetrate the insertion portion 5 of the electronic endoscope 2. The light incidental end of the light guide 11 is connected to the light source device 3. Further, the leading surface of the light guide 11 is disposed in the leading portion 10 of the insertion portion 5 so that irradiation light can be emitted from the leading portion 10.

The leading portion 10 has an objective lens system 12 fastened thereto. A solid-state image sensing device 13 is disposed at a position at which an image is formed by the objective lens system 12. The solid-state image sensing device 13 has sensitivity in a wide range from the ultraviolet region to the infrared region including a visible region. Signal lines 14 and 15 are connected to the solid-state image sensing device 13, the signal lines 14 and 15 being passed through the insertion portion 5 and the cable 7 as to be connected to the connector 8.

On the other hand, a lamp 16 constituting an irradiation means for emitting light in a wide band zone from ultraviolet rays to infrared rays is disposed in the light source device 3. The lamp 16 may be, for example, an ordinary xenon lamp, a strobe lamp or a halogen lamp. The xenon lamp, the strobe lamp and the halogen lamp are able to emit ultraviolet rays and infrared rays by a large quantity as well as visible rays. The type of the lamp may be selected to meet the way of usage.

The light source device 3 includes a discrimination signal generator 18 serving as an information supply means which emits different light source discrimination signal in accordance with the type of the lamp 16 and the irradiation (imaging) method, for example, the simultaneous method. The discrimination signal generator 18 has an arrangement that, for example, a light sensor (omitted from illustration) is disposed adjacently to the lamp 16 and a light source discrimination signal corresponding to the type of the light source is generated in accordance with a signal obtained by photoelectrical conversion performed by the light sensor.

The discrimination signal generator 18 may be a generator having an arrangement that setting can be performed in accordance with the type of the lamp and the like or a generator having an arrangement that setting is previously so performed as to cause a predetermined light source discrimination signal to be generated for each light source device 3.

The lamp 16 is supplied with electric power from a light source portion (omitted from illustration). Light emitted from the lamp 16 is made incident upon the light-incidental end of the light guide 11 and guided to the leading portion 10 via the light guide 11. As a result, light is emitted from the leading portion 10 so that the portion to be observed is irradiated with light.

Irradiation light is then returned by the portion to be observed, and it is imaged on the solid-state image sensing device 13 by the objective lens system 12 so that returned light is photoelectrically converted. The solid-state image sensing device 13 is, via the signal line 14, applied with drive pulses from a drive circuit 17 disposed in the processor 4 so that reading and transfer are performed in response to the drive pulses. A video signal read from the solid-state image sensing device 13 is, via the signal line 15, supplied to the video signal processing circuit 9. The video signal processing circuit 9 amplifies the video signal and subjects the video signal to signal processes, such as a γ-correction process and a white balance process. As a result, the video signal is transmitted as R, G and B signals or an NTSC composite signal.

The white balance operation is so controlled that, if a white subject is imaged for example, the values of the transmitted R, G and B signals are the same.

The R, G and B signals or the NTSC composite signal is supplied to the color monitor so that the observed portion is color-displayed by the color monitor.

The processor 4 includes a discrimination circuit 19 serving as a signal processing operation changing means for changing over the operation of a signal process to be described later in response to a light source discrimination signal to be transmitted from the discrimination signal generator 18 of the light source device 3. The discrimination signal generator 18 constituting a discrimination instruction means and the discrimination circuit 19 are connected to each other by a signal line 20.

The video signal processing circuit 9 properly changes over the operation for processing the video signal in response to a change-over signal supplied from the discrimination circuit 19 denoting the type of the light source.

In the foregoing structure, light emitted from the lamp 16 included in the light source device 3 is passed through the light guide 11 and is, from the leading portion 10, applied to a portion to be observed. The portion to be observed and irradiated with light from the light guide 11 is imaged on the solid-state image sensing device 13 by the objective lens system 12. The image (light) imaged on the solid-state image sensing device 13 is photoelectrically converted and read out at predetermined timing in response to drive pulses transmitted from the drive circuit 17 through the signal line 14. The video signal, which has been photoelectrically converted, is passed through the signal line 15 and supplied to the video signal processing circuit 9.

On the other hand, in the light source device 3, the discrimination signal generator 18 generates a light source discrimination signal corresponding to the type of the light source. The light source discrimination signal is supplied to the discrimination circuit 19 included in the processor 4 via the signal line 20. The discrimination circuit 19 discriminates the type of the light source. Information about the type of the light source is, as a change-over signal, supplied to the video signal processing circuit 9. The video signal processing circuit 9 changes over the signal processing operation in response to the change-over signal transmitted from the discrimination circuit 19 so that an optimum video signal process is performed.

Then, an example of the structure for transmitting the light source discrimination signal will now be described with reference to FIG. 4. Further, states of signals will now be described with reference to FIG. 5. The example of the structure shown in FIG. 4 has an arrangement that an apparatus having a means for automatically regulating light of the light source includes a light regulation signal line 21 which establishes the connection between the processor 4 and the light source device 3 and which is commonly used as the signal line 20 for transmitting the light source discrimination signal.

Figure 5A:
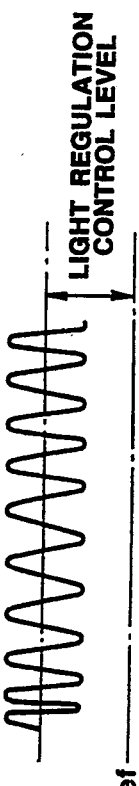
Figure 5B:
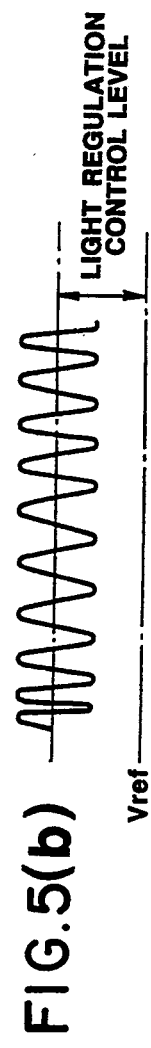
Figure 5C:
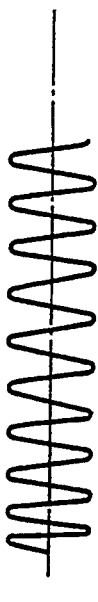

The discrimination signal generator 18 included in the light source device 3 converts light source information into a frequency signal. The discrimination signal generator 18 subjects the information to a so-called frequency modulation. The light source discriminating frequency signal is shown in FIG. 5 (a). The light source discriminating frequency signal denotes the type of the light source with the basic frequency thereof.

The light source discriminating frequency signal is superimposed on a light regulation signal to be described later on the light regulation signal line 21 by a superimposing circuit 22 in the light source portion. FIG. 5 (b) illustrates the foregoing signals.

The light source discriminating frequency signal transmitted through the light regulation signal line 21 of the endoscope 2 is separated from the light regulation signal by a superimposing circuit 23 in the processor portion so that it is made to be a light source discriminating frequency signal shown in FIG. 5 (c). The discrimination circuit 19, which has received the light source discriminating frequency signal, discriminates the type of the light source in accordance with the frequency component and transmits the result of the discrimination to the video signal processing circuit 9 as the change-over signal.

On the other hand, the light regulation signal is generated by a light regulation signal wave detection circuit 24 in the processor 4. The light regulation signal wave detection circuit 24 detects the wave of an output from the solid-image sensing device 13 to generate a light regulation signal. The light regulation signal is passed through the superimposing circuit 23 in the processor portion, the light regulation signal line 21 and the superimposing circuit 22 in the light source portion. Then, the light regulation signal is supplied to a light regulating circuit 25 included in the light source device 3. Since the light regulation signal is a DC signal as shown in FIG. 5 (b), it can easily be separated and synthesized to the light source discriminating frequency signal, which is an AC component. Symbol Vref shown in FIG. 5 (b) represents a standard level for the light regulation signal.

The light regulating circuit 25 automatically controls the brightness of the lamp 16.

By using the light regulation signal line 21 and the superimposing circuits 22 and 23 as described above, the light source discriminating frequency signal can be transmitted.

Figure 4:
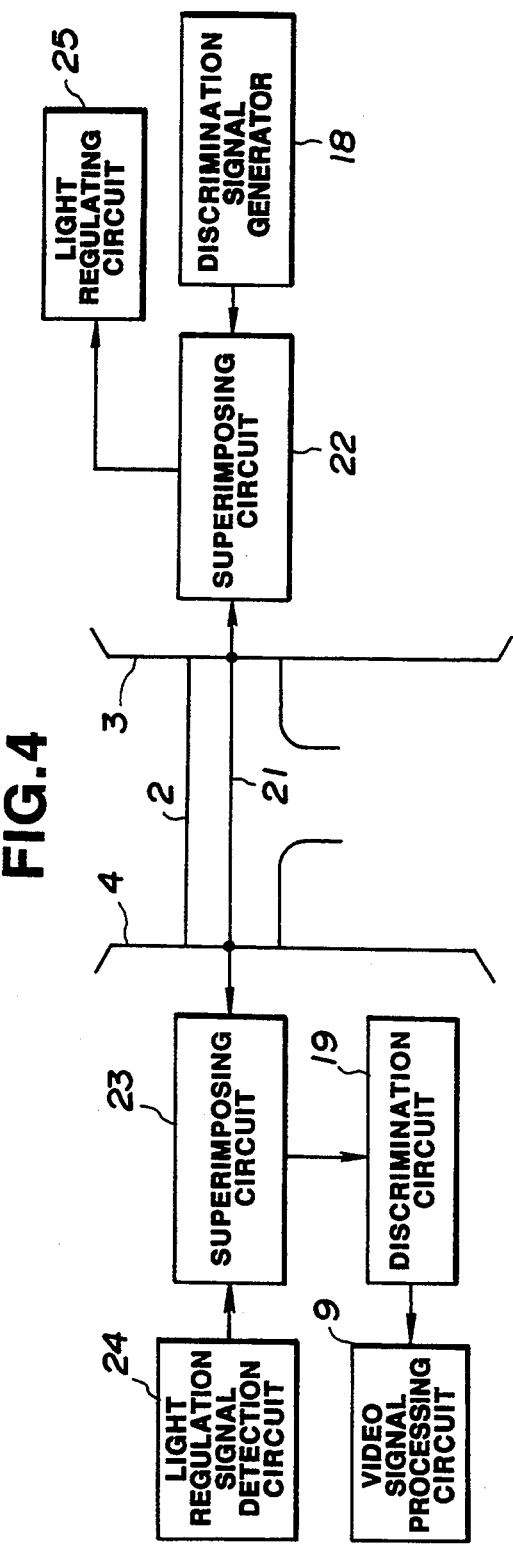

Although the example of the structure, shown in FIG. 4, has the arrangement that the synthesis with the light regulation signal is performed, the discrimination signal may be transmitted through an exclusive transmission line provided for the purpose of transmitting the discrimination signal. In the case where the exclusive line is used, the discrimination signal may be a code signal or a DC signal in place of the frequency signal.

Figure 6:
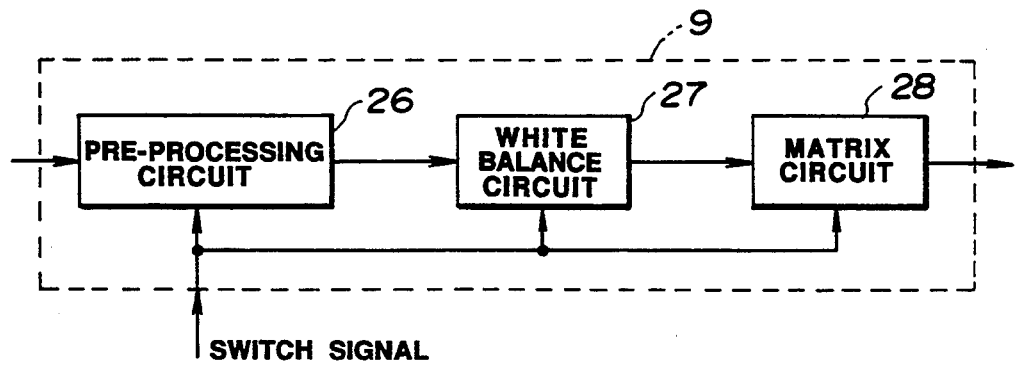

An example of the video signal processing circuit 9 will now be described with reference to FIG. 6. The video signal supplied to the video signal processing circuit 9 is supplied to a pre-processing circuit 26. The pre-processing circuit 26 performs a plane sequential process or a simultaneous process in accordance with the method of irradiation.

The change over of the pre-processing circuit 26 is performed in response to the change-over signal transmitted from the discrimination circuit 19. The change-over signal is generated in accordance with the type of the light source. The change-over signal includes information whether the light source is a plane sequential light source or a simultaneous light source and acts as a signal for instructing to perform proper change over. The change-over signal also changes over the method of generating a signal for regulating light from the light source.

The pre-processing circuit 26 transmits color signals, that is, R, G and B signals, to the white balance circuit 27. In the white balance circuit 27, control is so performed that if white is imaged for example, the levels of the R, G and B signals coincide with one another. The foregoing operation is usually performed in such a manner that white is imaged and the level of the transmitted video signal is detected. However, the foregoing circuit 27 changes its operation in accordance with the type of the light source when a presetting operation is performed or the initial value is intended to be optimized. The foregoing change over of the operation is controlled in response to the change over signal corresponding to the type of the light source.

The R, G and B signals transmitted from the white balance circuit 23 are supplied to a matrix circuit 28. The matrix circuit 28 performed a matrix calculation by using the following equation in order to improve color reproducibility:

$$\begin{pmatrix} R' \\ G' \\ B' \end{pmatrix} = A \begin{pmatrix} R \\ G \\ B \end{pmatrix}$$

where symbol A is a 3×3 matrix. The supplied R, G and B signals are converted into R', G' and B' signals by the matrix A.

In order to optimally reproduce colors, the matrix A must be changed over in accordance with the type of the lamp and the method of irradiation (the plane sequential method or the simultaneous method). Therefore, the matrix circuit 28 changes setting of the matrix A in response to the change-over signal.

As described above, this embodiment has the arrangement that the processing operation performed by the video signal processing circuit 9 is controlled in response to the (different) change-over signals generated in accordance with the type of the lamp and the method of irradiation. As a result, the video signal can be processed optimally and, accordingly, deterioration in the image quality can be prevented. That is, this embodiment enables the image quality, that tends to deteriorate if the processing operation is not changed, to be be improved.

The control of the operation of processing the video signal to be performed in response to the change-over signal is not limited to the foregoing method of application. It can be applied to all of factors that are changed due to the type of the light source, such as a method of driving a solid-state image sensing device or control of a memory.

Figure 7:
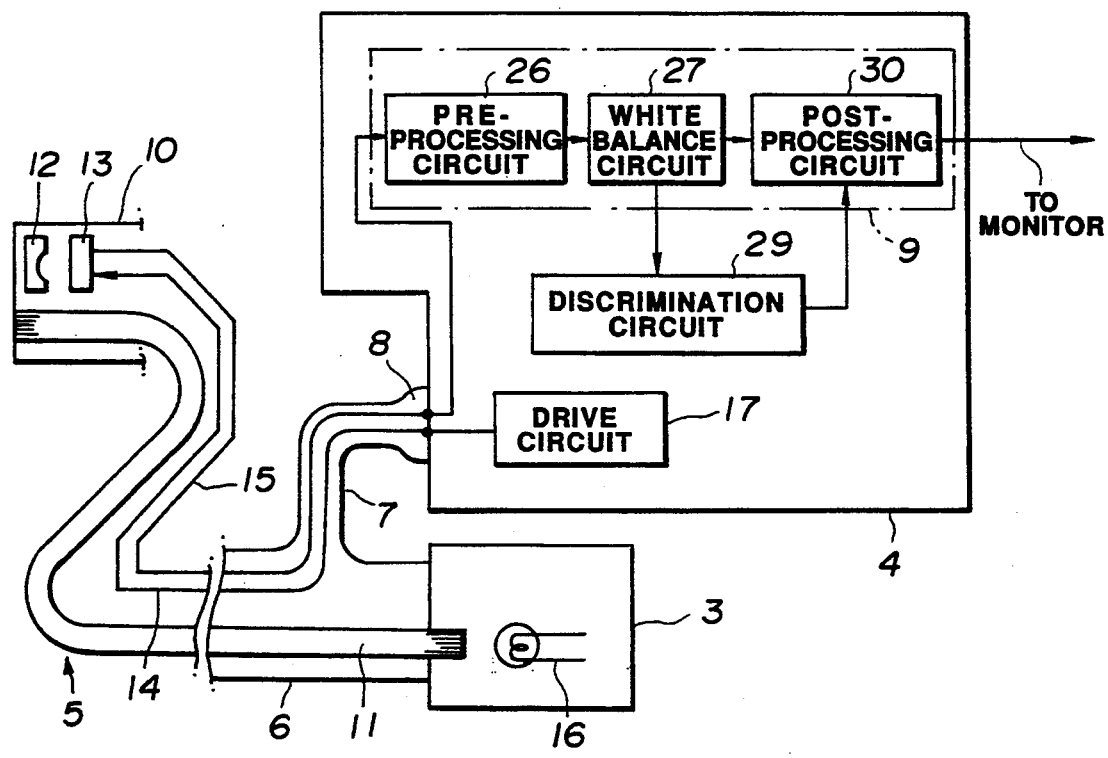
FIGS. 7 to 9 are overall structural views which illustrate an electronic endoscope apparatus according to a second embodiment.
Figure 8:
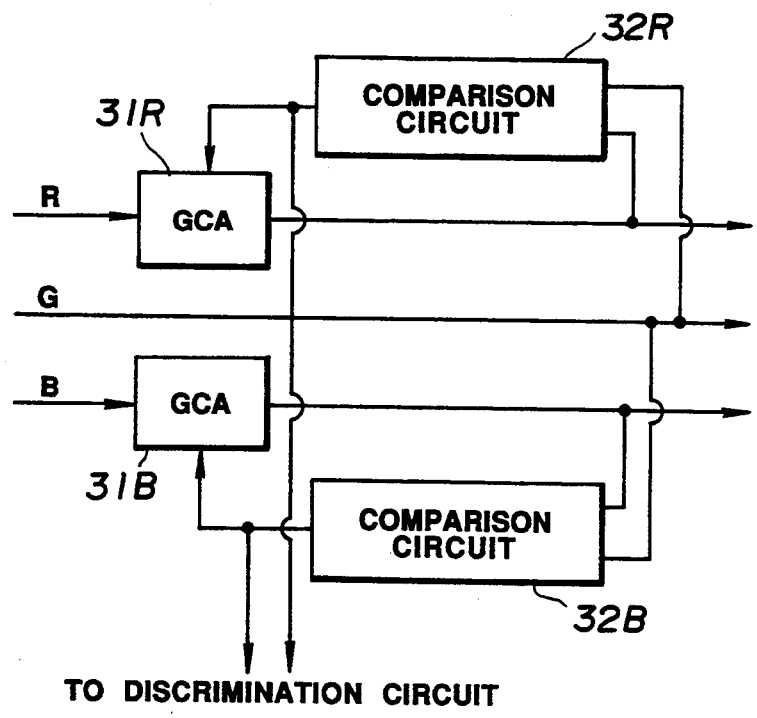
Figure 9:
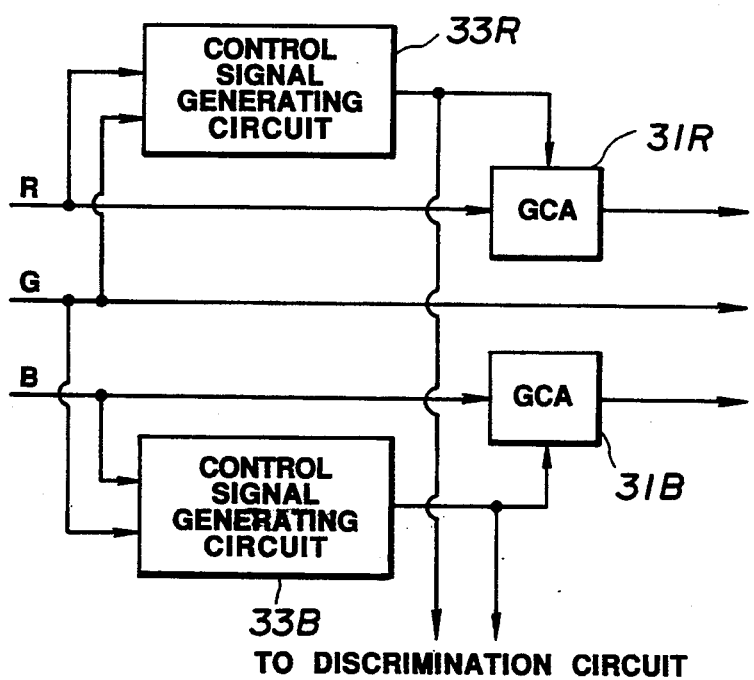

FIGS. 7 to 9 relate to a second embodiment of the present invention. FIG. 7 is an overall structural view which illustrates an electronic endoscope apparatus.

FIG. 8 is a block diagram which illustrates a white balance circuit. FIG. 9 is a block diagram which illustrates a white balance circuit different from that shown in FIG. 8.

The second embodiment has a structure which is different from that of the first embodiment shown in FIG. 3 and in which the discrimination signal generator 18 is omitted and a discrimination circuit 29 is provided, the discrimination circuit 29 being arranged to discriminate the type of the light source in response to an output signal from the video signal processing circuit 9. The structure of the video signal processing circuit 9 has a structure in which a post-processing circuit 30 is provided in place of the matrix circuit 28 shown in FIG. 6. The same structures and operation as those of the first embodiment are given the same reference numerals and their descriptions are omitted here. Then, the description will be made about the different portions from the first embodiment.

The operation to be performed until the video signal is supplied from the solid-state image sensing device 13 to the processor 4 is performed similarly to that of the first embodiment. The video signal in this embodiment is subjected to predetermined processes, such as a color separation process and a simultaneous process in the pre-processing circuit 26 of the video signal processing circuit 9. Then, the video signal is received by the white balance circuit 27. In the white balance circuit 27, control is so performed that the levels of the R, G and B signals coincide with one another when, for example, white is imaged. In order perform the foregoing level adjustment, the white balance circuit 27 uses an output signal from the pre-processing circuit 26 to generate a control signal. Examples of the structure for performing the foregoing control are shown in FIGS. 8 and 9.

A white balance circuit shown in FIG. 8 comprises comparison circuits 32R and 32B for subjecting the levels of R and B signals transmitted from gain control amplifiers (GCA) 31R and 31B at the time of imaging white and a supplied G signal to a comparison. Further, control signals transmitted from the comparison circuits 32R and 32B are used to adjust the gains of the gain control amplifiers 31R and 31B to make the levels of the R, G and B signals coincide with one another. The foregoing control signals are also transmitted to the discrimination circuit 29.

A white balance circuit shown in FIG. 9 comprises control signal generating circuits 33R and 33B which transmit control signals in accordance with the difference between the levels of the supplied R and B signals and the level of the supplied G signal at the time of imaging white so that the levels of the R and B signals transmitted from the gain control amplifiers 31R and 31B coincide with the level of the supplied G signal. The foregoing control signals are transmitted to the gain control amplifiers 31R and 31B. The foregoing control signals are also transmitted to the discrimination circuit 29.

The control signal for arranging the white balance varies depending upon the type of the light source.

If a consideration is made while making a xenon lamp to be a standard, the color temperature of the light source is raised in a case where the lamp has been changed to a halogen lamp. Therefore, energy of long wavelength component of light is enlarged, causing the R signal to be supplied to the white balance circuit 27 is further enlarged and the B signal is made further small.

As a result, the control signals to be supplied to the gain control amplifiers 31R and 31B are made such that the control signal for the R signal is made smaller and that for the B signal is enlarged as compared with the control signals for use with the xenon lamp. The foregoing control signals are received by the discrimination circuit 29 to discriminate the type of the light source. The discrimination circuit 29 transmits the result of the discrimination to the post-processing circuit 30 as a change-over signal.

By using the foregoing change-over signal, the post-processing circuit 30 changes over the values such as the matrix constant similarly to the first embodiment.

As described above, the second embodiment has the arrangement that the control signals for the white balance process are used to discriminate the type of the light source and the result of the discrimination is used to change over the video signal process. Therefore, this embodiments is able to eliminate a necessity of transmitting the discrimination signal from the light source. As a result, the system can be simplified as compared with the system according to the first embodiment.

Although the foregoing explanation is made about the arrangement that the process to be performed by the post-processing circuit 30 is simply changed over, a portion of the operations to be performed by the pre-processing circuit 20, that does not relate to the light source discrimination, may be changed over.

Figure 10:
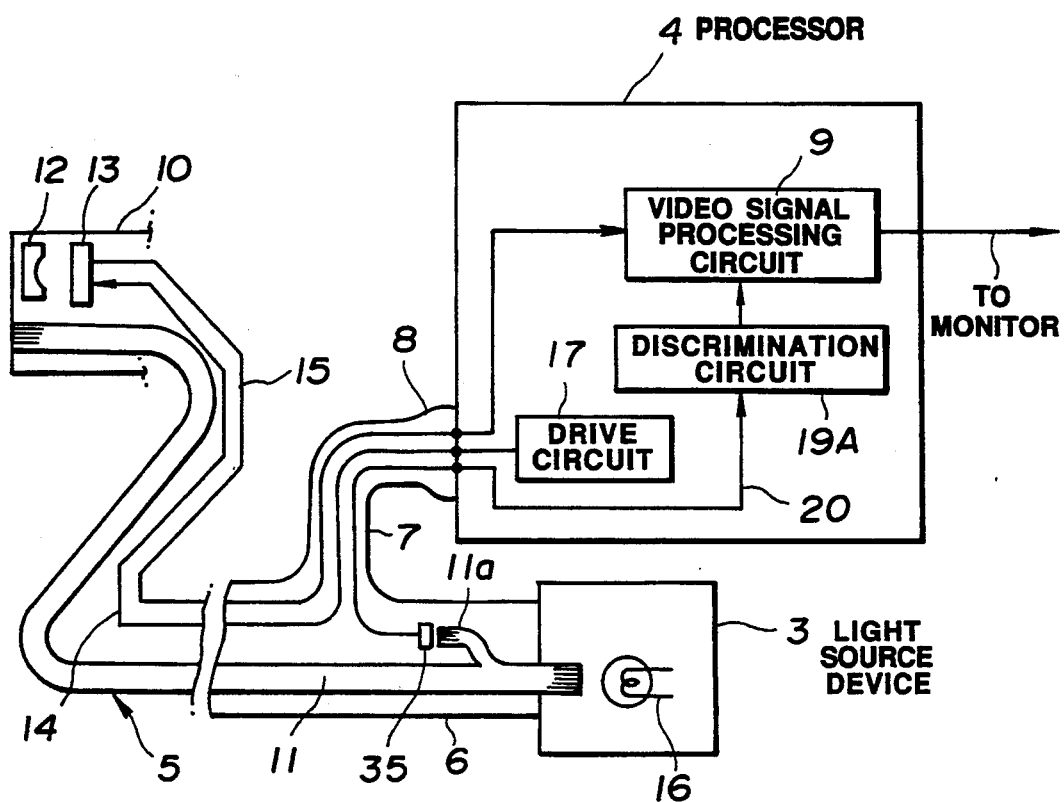
FIG. 10 is an overall structural view which illustrates an electronic endoscope apparatus according to a third embodiment.

FIG. 10 is an overall structural view which illustrates an electronic endoscope apparatus according to a third embodiment of the present invention.

The third embodiment has a structure constituted such that a light sensor disposed at a branching terminal of the line guide 11 is disposed in place of the discrimination signal generator 18 according to the first embodiment shown in FIG. 3. Further, the foregoing light sensor and the discrimination circuit act to discriminate the type of the light source. The same structures and operations as those according to the first embodiment are given the same reference numerals and their descriptions are omitted here.

In the third embodiment, the video signal is read out from the solid-state image sensing device 13 and processed by the processor 4 similarly to the first embodiment.

As shown in FIG. 10, the light guide 11 is branched into two portions in a direction from the light incidental end toward the light emission end. The light guide 11 guides light emitted from the light source to either of the light emission ends of the leading portion 10. Further, a portion of light emitted from the light source is picked up from the end surface of a branched portion 11a. A sensor 35 for detecting emitted light is disposed adjacently to the end portion of the branched portion 11a. The sensor 35 senses the color temperature of light transmitted from the light source and a spectrum energy distribution. Data about the result of the sensing operation is discriminated by a discrimination circuit 19A of the processor 4. The result of the discrimination is transmitted as a change-over signal to the video signal processing circuit 9. Since the operation to be performed by the video signal processing circuit 9 in response to the change-over signal is the same as that according to the first embodiment, its description is omitted here.

The sensor 35 may use light branched at any portion of the light guide 11 and may be disposed arbitrarily if it is irradiated with light emitted from the light source.

Although the explained white balance process and the signal process to be performed in each of the foregoing embodiments are arranged to use the R, G and B signals, the foregoing processes may be applied to a case where a brightness (Y) signal or color difference signals (R-Y, B-Y and the like) are used. Although emitted from illustration, the lamp 16 of the light source device 3 time-sequentially emits a plurality of light beams having different wavelength regions in a case of the plane sequential method. The foregoing structure is realized by interposing a rotative filter between the light-incidental end of the light guide 11 and the lamp 16.

Figure 11:
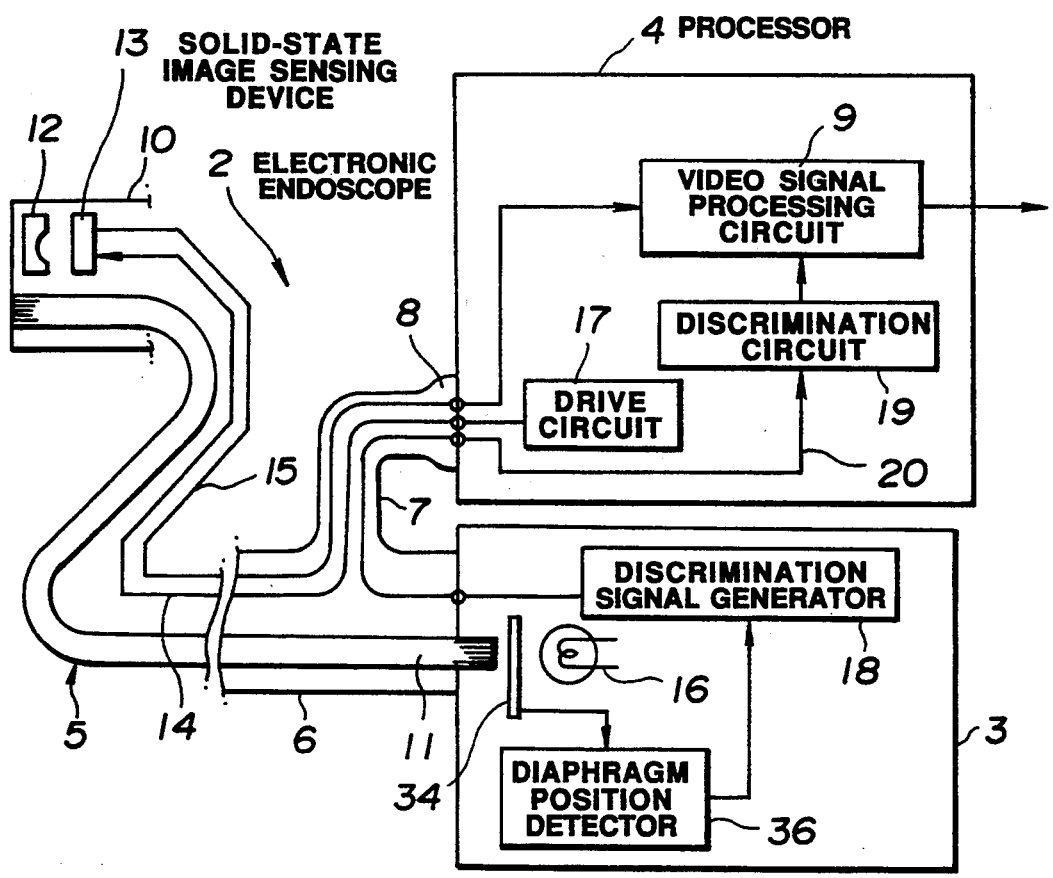
FIGS. 11 and 12 relate to a fourth embodiment.
Figure 12:
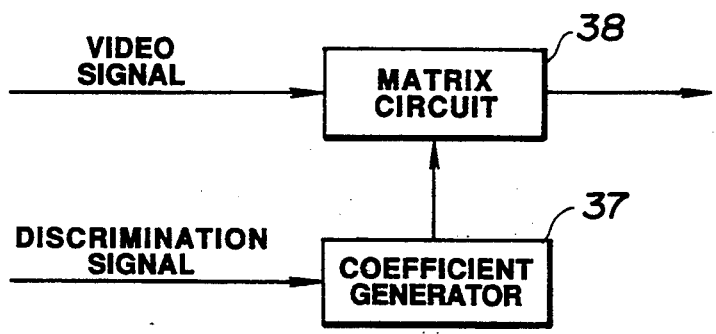

FIGS. 11 and 12 relate to a fourth embodiment of the present invention. FIG. 11 is an overall structural view of an electronic endoscope apparatus. FIG. 12 is a block diagram which illustrates an example of the structure of a video signal processing circuit.

This embodiment has an arrangement that a diaphragm 34 for adjusting the quantity of irradiation light emitted from the lamp 16 is provided for the light source device 3 according to the first embodiment. The diaphragm 34 controls the quantity of light to be made incident upon the light guide 11 from the lamp 16 is controlled so that an optimum video signal level is obtained. At this time, the shape of the diaphragm and the positional relationship between the diaphragm and the optical axis sometimes change the color of light emitted though the light guide 11. The main reason for this is that the diffraction effect of light is particularly enhanced if the quantity of diaphragm is large.

This embodiment has an arrangement that the color reproducibility of the subject is improved in the foregoing state by detecting a diaphragm position and the like to change the process to which the video signal is subjected. Accordingly, the light source device 3 includes a diaphragm position detector 36 for detecting the diaphragm position, that is, the diaphragm quantity. A detection signal transmitted from the diaphragm position detector 36 is supplied to the discrimination signal generator 18. A discrimination signal transmitted from the discrimination signal generator 18 is transmitted to the discrimination circuit 19 of the processor 4. The same structures as those according to the first embodiment are given the same reference numerals and their descriptions are omitted here.

In the foregoing structure, the main lamp 16 of the light source device 3 usually emits irradiation light. Light emitted from the main lamp 16 is passed through the light guide 11, followed by irradiation of the subject with light through the leading portion of the endoscope. The image of the subject is imaged on the solid-state image sensing device 13 by the objective lens 12. The subject image is converted into an electric signal by the solid-state image sensing device 13, and then it is transmitted to the processor 4. As a result, the image is processed by the video signal processing circuit 9.

The position of the diaphragm 34 is detected by the diaphragm position detector 36, and information about the diaphragm position is transmitted to the discrimination signal generator 18. The discrimination signal generator 18 previously stores, for example, information about change in the color taken place depending upon the position of the diagram 34. Therefore, the discrimination signal generator 18 transmits a discrimination signal corresponding to information about the color change. The discrimination circuit 19 in the portion including the processor 4 converts the signal supplied from the discrimination signal generator 18 into a color conversion signal. Then, the color conversion signal is transmitted to the video signal processing circuit 9.

FIG. 12 illustrates an example of the structure of the video signal processing circuit 9. The video signal processing circuit 9 receives the signal supplied from the discrimination circuit 19 by a coefficient generator 37 thereof to generate a matrix constant corresponding to a color conversion signal transmitted from the discrimination circuit 19. Color conversion setting of the matrix circuit 38 serving as a color conversion means is changed so that the color of the transmitted image is changed to be adaptable to the diaphragm position.

This embodiment enables an image exhibiting normal color reproducibility to be always obtained regardless of the change in the color of emitted (irradiation) light caused by the diaphragm.

Although this embodiment comprises the matrix circuit serving as the color conversion means, another color conversion means, for example, a structure which converts color in a color space conforming to classification A7-1593 or A7-1594 may be employed. The color conversion means may be structured in such a manner that a programmable device, such as an LCA, is used and it is again programmed in accordance with an instruction issued from the discrimination circuit 19.

Figure 13:
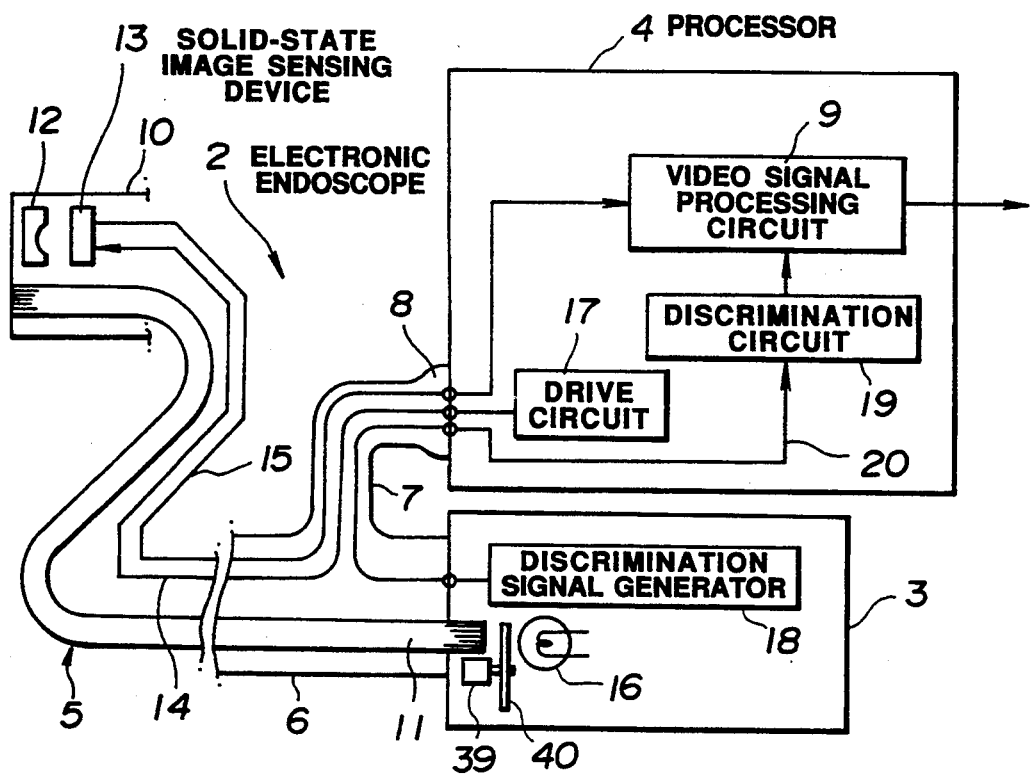
FIGS. 13 to 17 relate to a fifth embodiment.
Figure 14:
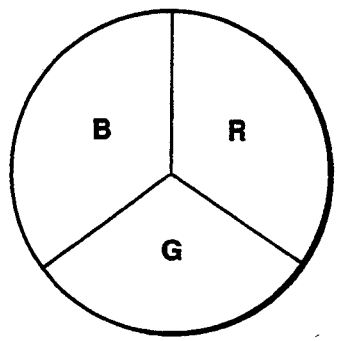
Figure 15:
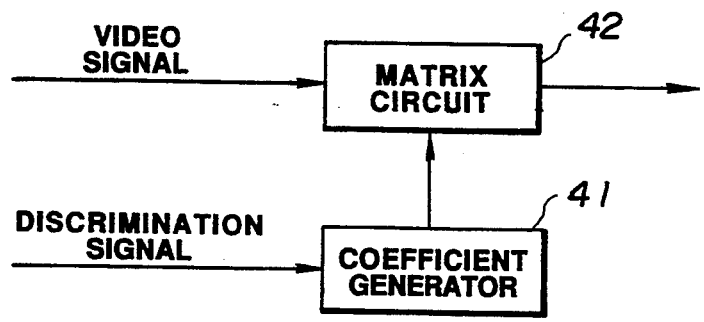
Figure 16:
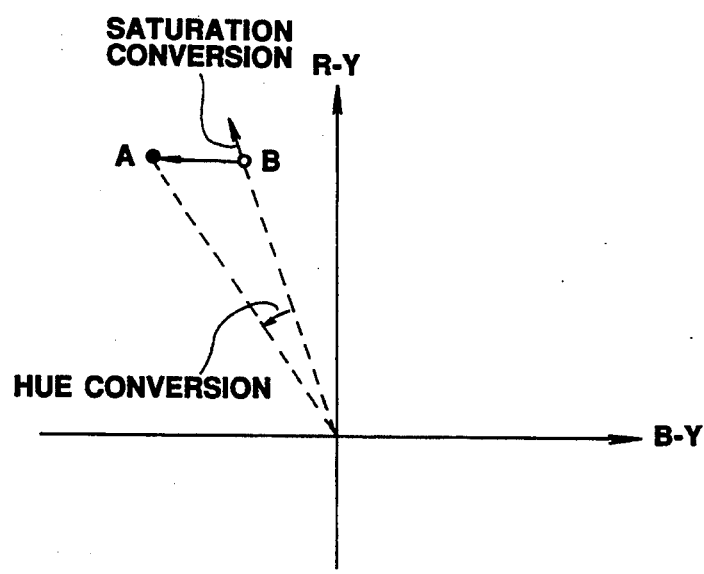
Figure 17:
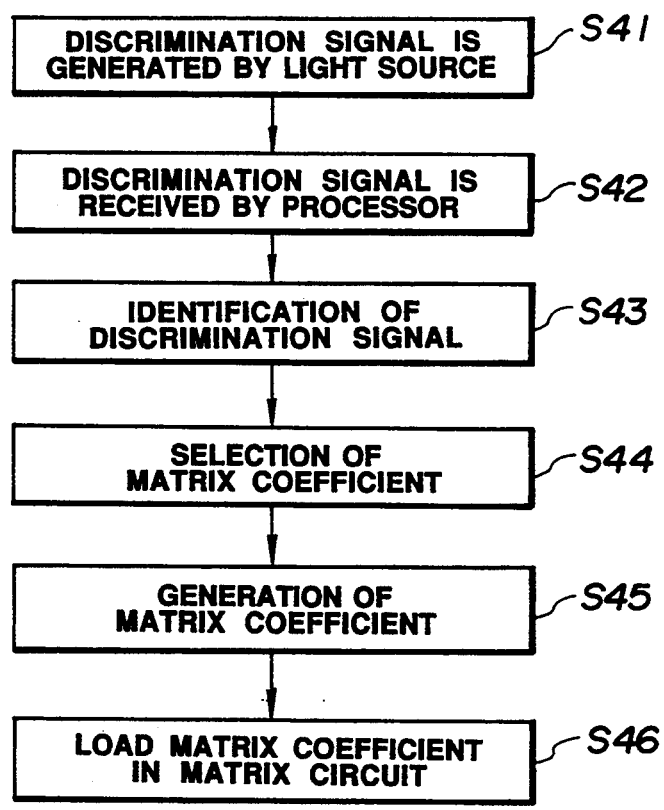

FIGS. 13 to 17 relate to a fifth embodiment of the present invention. FIG. 13 is an overall structural view which illustrates a electronic endoscope apparatus. FIG. 14 is a structural view which illustrates a rotative filter. FIG. 15 is a block diagram which illustrates an example of the structure of a video signal processing circuit. FIG. 16 is an explanatory view of color conversion. FIG. 17 is a flow chart relating to change and setting of a matrix coefficient.

A light source device 3 according to this embodiment has a structure to irradiate plane sequential irradiation light. Further, a rotative filter 40 to be rotated by a motor 39 is disposed on the optical path through which irradiation light passes. That is, a color decomposing rotative filter 40 including R (red), G (green) and B (blue) filters as shown in FIG. 14 is inserted between the lamp 16 and the light guide 11. The processor 4 shown in FIG. 13 is so structured as to be supplied with a correction signal for the rotative filter 40 from the light source device 3 at the discrimination signal generator 18 thereof. In response to the correction signal, the operation of the color conversion means of the video signal processing circuit 9 is changed. The same structures and operations as those according to the first embodiment are given the same reference numerals and their descriptions are omitted here.

In the foregoing structure, the main lamp 16 of the light source device 3 usually emits irradiation light. Since the rotative filter 40 is being rotated by the motor 39, irradiation light is made in synchronization with the signal reading cycle of the solid-state image sensing device so that signals corresponding to the R, G and B filters are made incident upon the light guide 11. Light decomposed into a plurality of wavelength band by each filter is passed through the light guide 11. Then, light is time-sequentially applied to the subject from the leading portion of the endoscope. The subject is imaged on the solid-state image sensing device 13 by the objective lens 12. The solid-state image sensing device 13 time-sequentially transmits electric signals corresponding to the color filters. The electric signals are made to be simultaneous signals by the video signal processing circuit 9, and then the simultaneous signals are subjected to a color process before they are transmitted.

The rotative filter 40 comprises R, G and B filters which have different filter spectrum characteristics. Therefore, the difference of the filter causes the electric signals transmitted from the solid-state image sensing device 13 and corresponding to the colors to be made different. As a result, the color reproducibility of the video signal is made different.

Since the filter is different for each light source, this embodiment has an arrangement that the operation of the color conversion means of the video signal processing circuit 9 is changed in accordance with the light source. FIG. 15 illustrates an example of the structure of the color conversion means of the video signal processing circuit 9. The processing circuit 9 comprises a coefficient generator 41 and a matrix circuit 42.

The discrimination signal generator 18 of the light source device 3 previously stores data for varying setting of the signal process to be performed by the processor 4 in accordance with the spectrum characteristics of the rotative filter 40 and the like.

The operation will now be described with reference to the flow chart shown in FIG. 17. When the light source device 3 and the processor 4 are first electrically connected to each other, data corresponding to the rotative filter 40 included in the light source is, in steps S41 and S42, transmitted to the processor 4 by the discrimination signal generator 18 included in the light source. In step S43, the discrimination circuit 19 of the processor 4 identifies transmitted data.

In steps S44 and S46, the coefficient generator 41 of the video signal processing circuit 9 selects and generates a matrix coefficient, which correspond to the employed rotative filter 40, in response to a discrimination signal transmitted from the discrimination circuit 19. The generated matrix coefficient is loaded into the matrix circuit 46. As a result, the operation of the matrix circuit 42 is changed.

A method of changing the matrix coefficient will now be described.

Important colors for reproducing color with the endoscope are generally red shades. For example, if red serving as the standard color is imaged, an assumption is made that the position of a color signal corresponding to red must be, on a vector scope, at position A shown in FIG. 16.

Even if the white balance adjustment is performed, the position on the vector scope corresponding to the standard red cannot be made predetermined position A due to scatter in the spectrum characteristics of the rotative filter 40 of the light source device as described above. If the position of the color signal on the vector scope is, for example, position B shown in FIG. 16, a matrix constant for converting the saturation and the hue of the signal corresponding to the standard red is set in the matrix circuit 42 and conversion is so made that the position is made the position A on the vector scope.

Although the foregoing explanation is made solely about red shades, a plurality of colors are considered in actual and the matrix constant is so determined that totally optimum color reproduction is realized.

If the matrix circuit 42 comprises an SRAM or the like, the constant change is easily enabled.

This embodiment is able to maintain satisfactory color reproducibility without the change in the color even if a different rotative filter of the light source is used.

Although the color conversion means is the matrix circuit in this embodiment, another color conversion means, for example, a structure for performing conversion in a color space conforming to classification A7-1593 or A7-1594 may be employed. The color conversion means may be structured in such a manner that a programmable device, such as an LCA, is used and it is again programmed in accordance with an instruction issued from the discrimination circuit 19.

Figure 18:
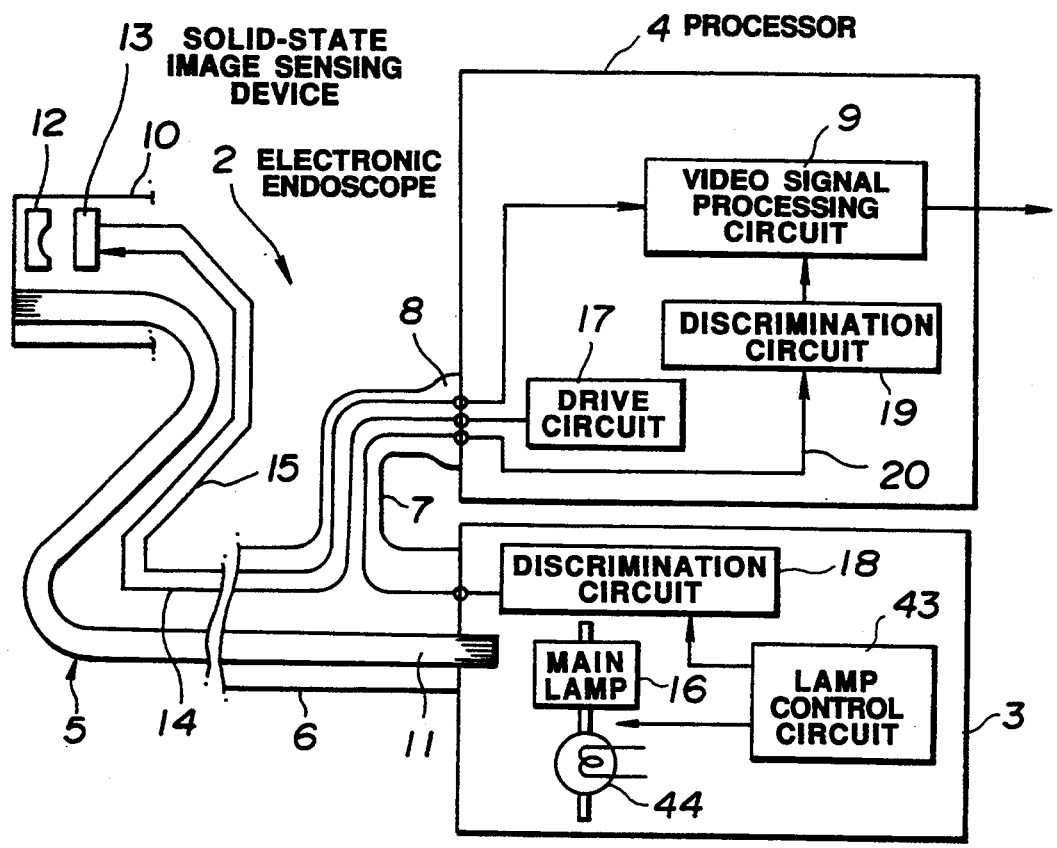
FIGS. 18 to 22 relate to a sixth embodiment.
Figure 19:
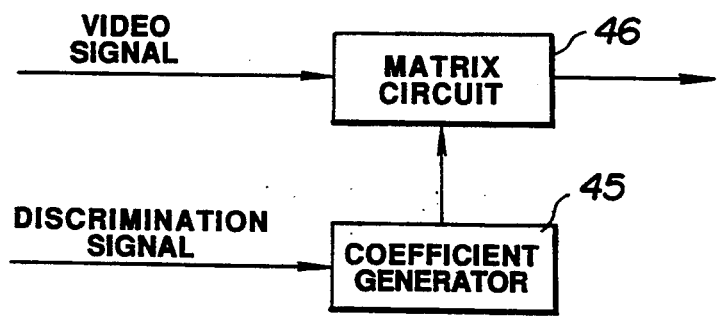
Figure 20:
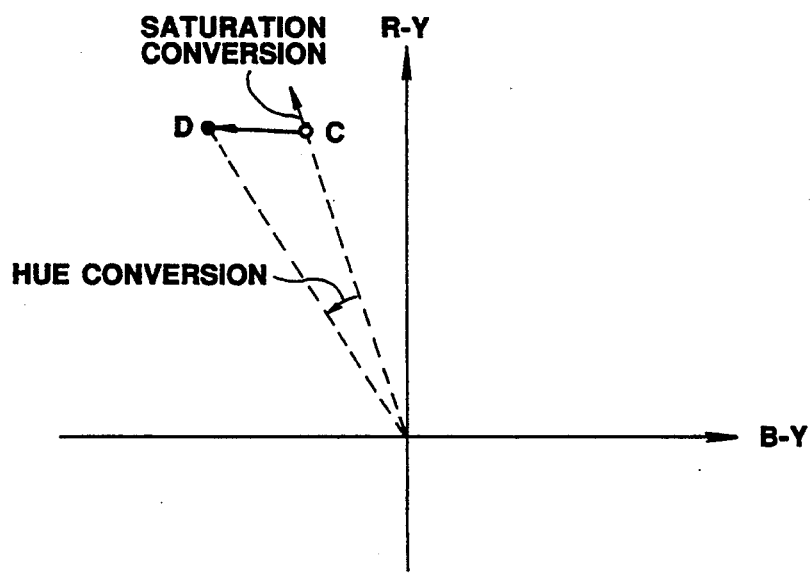
Figure 21:
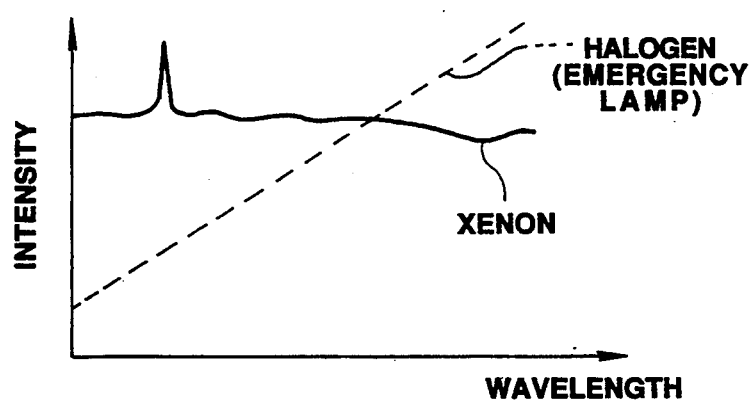
Figure 22:
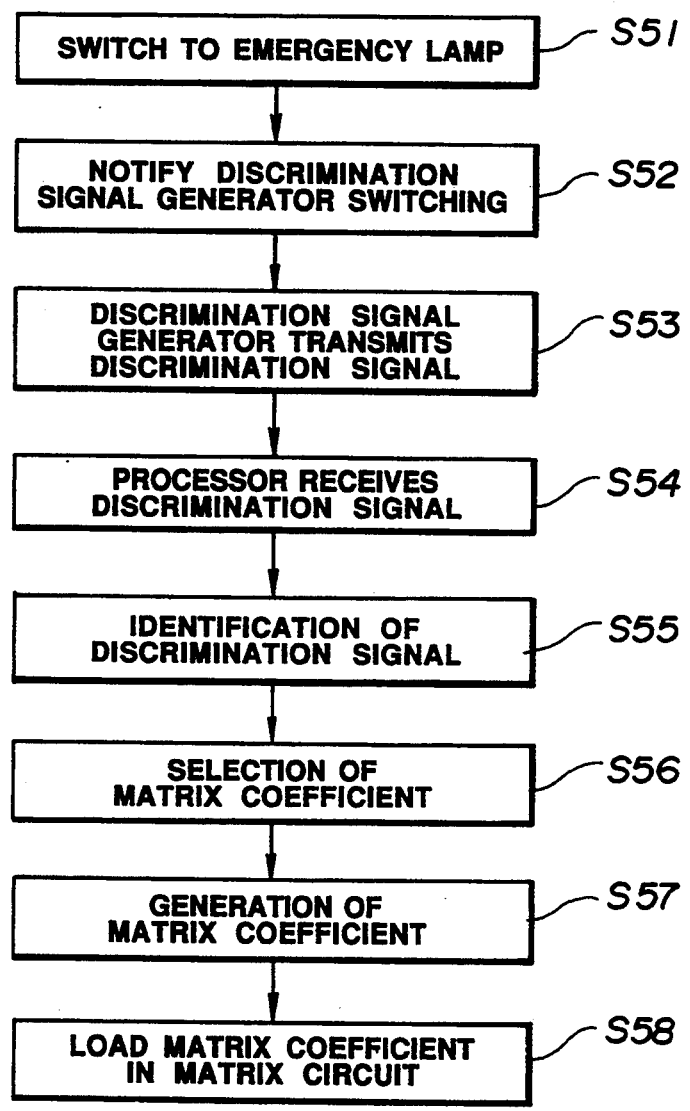

FIGS. 18 to 22 relate to a sixth embodiment of the present invention. FIG. 18 is an overall structural view which illustrates an electronic endoscope apparatus. FIG. 19 is a block diagram which illustrates an example of a video signal processing circuit. FIG. 20 is an explanatory view of chromaticity conversion. FIG. 21 is a graph of the characteristics of a usual lamp and an emergency lamp. FIG. 22 is a flow chart relating to change and setting of the matrix coefficient.

The light source device according to this embodiment is so structured that changing over to the emergency lamp is performed if the usual lamp is burned down. Therefore, the structure is arranged so that, if the light source has been changed over to the emergency lamp, the process to be performed by the processor, for example, the operation of the color conversion means is changed to be adaptable to the light quantity and the spectrum characteristics of the emergency lamp.

In this embodiment, the main lamp 16, which is the usual lamp of the light source device 3 shown in FIG. 18 is, for example, a xenon lamp. If the main lamp 16 cannot be lit for to some reason during the inspection, a lamp control circuit 43 causes an emergency lamp 44 to irradiate the subject, the emergency lamp 44 being a halogen lamp for example.

The lamp control circuit 43 notifies the discrimination signal generator 18 whether or not the lamp, which is being used, has been changed over to the emergency lamp. The discrimination circuit 19 of the processor 4 shown in FIG. 18 changes over the process operation to be performed by the video signal processing circuit 9 in response to a discrimination signal supplied from the discrimination signal generator 18. The same structures and operations as those according to the first embodiment are given the same reference numerals and their descriptions are omitted here.

In the foregoing structure, the main lamp 16 of the light source device 3 usually irradiates light. Irradiation light emitted from the main lamp 16 is passed through the light guide 11 and applied to a subject through the leading portion of the endoscope. The subject is imaged on the solid-state image sensing device 13 by the objective lens 12 and converted into an electric signal by the solid-state image sensing device 13. The electric signal is transmitted to the processor 4 and processed by the video signal processing circuit 9.

The operation will now be described with reference to the flow chart shown in FIG. 22.

If the main lamp 16 cannot be lit for some reason during an inspection, changing over is performed by the lamp controller 43 in step S51 so that the irradiation by the emergency lamp 44 is performed. Since the emergency lamp 44 is the halogen lamp, the irradiation is performed at a color temperature which is lower than that realized with the xenon lamp as shown in FIG. 21. If the video signal is, at this time, processed by the video signal processing circuit 9 which has been set up to be adaptable to the xenon lamp exhibiting a high color temperature, the color becomes different from the actual color. Therefore, the inspection cannot be continued properly.

Accordingly, the lamp controller 43 changes over the main lamp 16 to the emergency lamp 44 and as well as notifies, in step S52, the discrimination signal generator 18 that the lamp has been changed over. In step S53, the discrimination signal generator 18 transmits, to the processor 4, a discrimination signal for notifying that the change over to the emergency lamp has been performed. In steps S54 and S55, the discrimination circuit 19 of the processor 4 recognizes that the lamp has been changed over. In steps ensuing step S56, the contents of processes to be performed by the video signal processing circuit 9 are changed.

Figure 1:
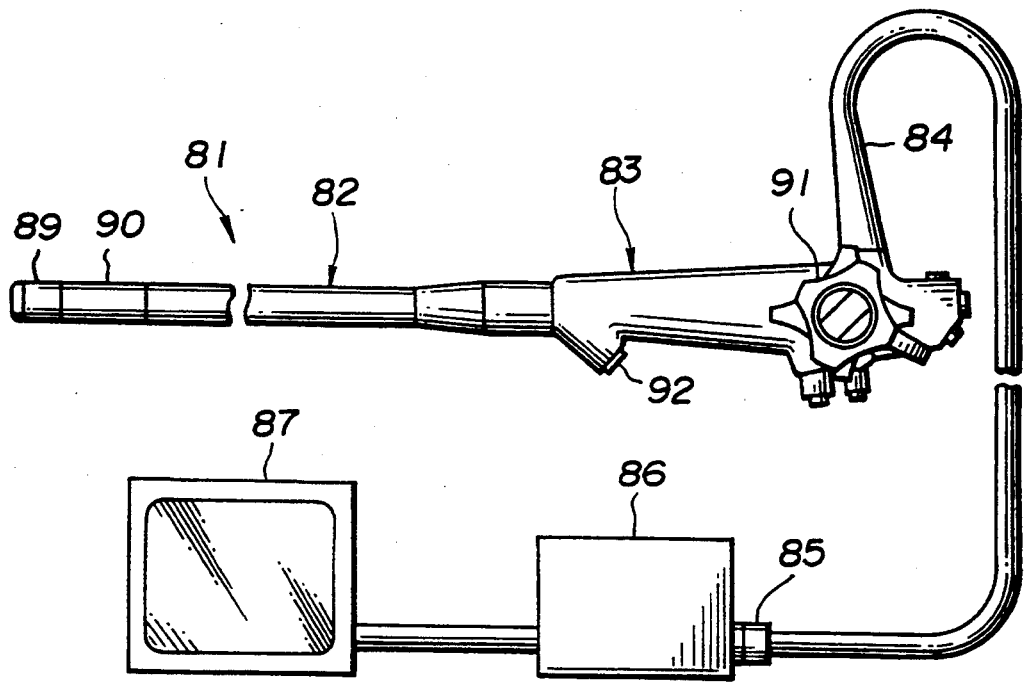
FIG. 1 is an overall structural view which illustrates an electronic endoscope apparatus according to a prior art.
Figure 2:
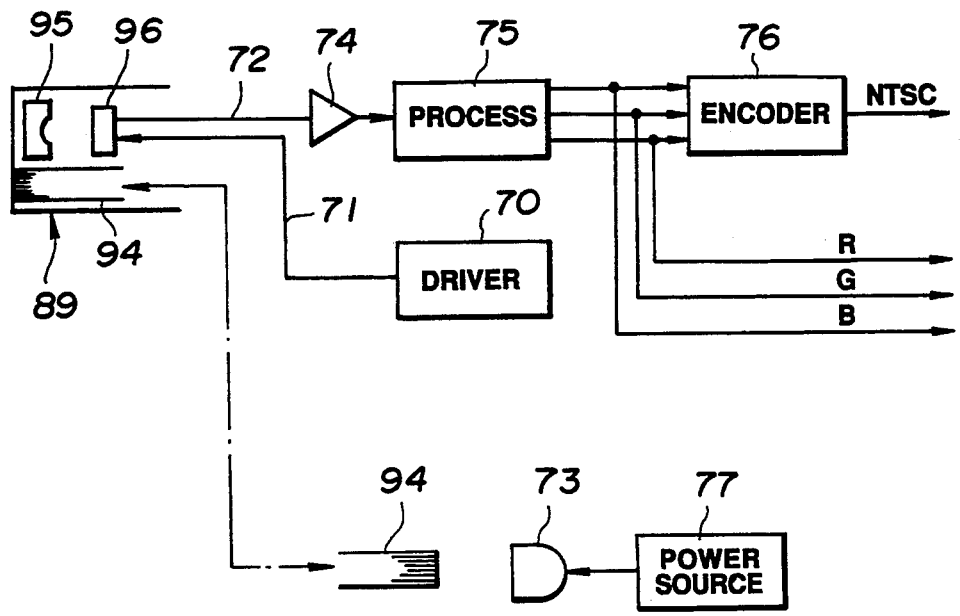
FIG. 2 is a block diagram which relates to a light source and a signal process to be performed by the apparatus according to the prior art.

An example of the structure of the color conversion means of the video signal processing circuit 9 is shown in FIG. 2. When a lamp change-over signal has been supplied from the discrimination circuit 19 to the video signal processing circuit 9, its coefficient generator 45 transmits a matrix coefficient adaptable to the changed over emergency lamp to the matrix circuit 46.

Then, a method of changing the matrix constant will now be described.

Important colors for reproducing color with the endoscope are generally red shades. For example, if red serving as a standard is imaged, an assumption is made that the position of a color signal corresponding to red must be, on a vector scope, at position D shown in FIG. 20.

As shown in FIG. 21, the xenon lamp and the halogen lamp have different light emission characteristics. Therefore, even if the white balance adjustment is performed, the position on the vector scope corresponding to the standard red cannot be made predetermined position D. If the position is, for example, position C shown in FIG. 21, the matrix circuit 46 selects and sets a matrix constant for converting the saturation and the hue of the signal corresponding to the standard red. Then, the coefficient causing the position to be at position D on the vector scope is loaded, and then the conversion is performed.

If the matrix circuit 46 comprises an SRAM or the like, the constant change is easily enabled.

Although the foregoing explanation is made solely about red shades, a plurality of colors are considered in actual and the matrix constant is so determined that totally optimum color reproduction is realized.

Although the color conversion circuit is the matrix circuit in this embodiment, another color conversion means, for example, a structure for performing conversion in a color space conforming to classification A7-1593 or A7-1594 may be employed. The color conversion means may be structured in such a manner that a programmable device, such as an LCA, is used and it is again programmed in accordance with an instruction issued from the discrimination circuit 19.

This embodiment is able to prevent change in the image, and more particularly change in the color even if the light source has been changed over from the usual lamp to the emergency lamp.

Figure 23:
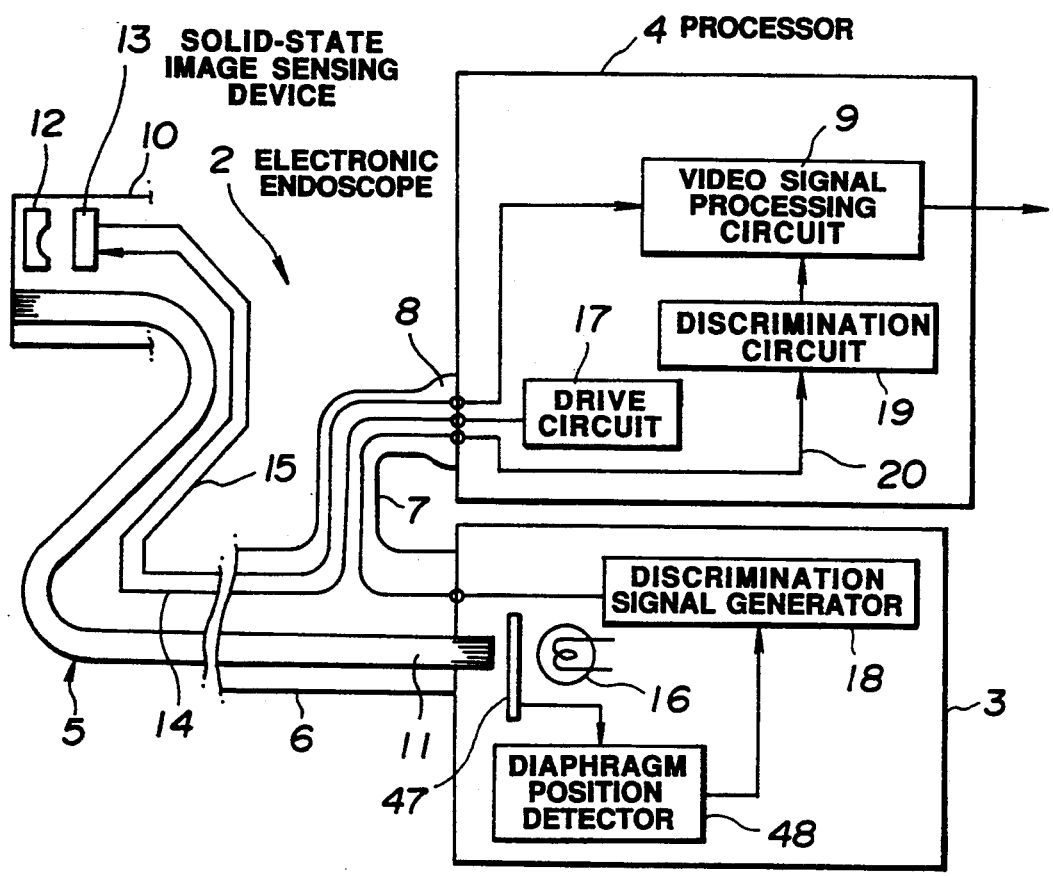
FIGS. 23 to 26 relate to a seventh embodiment.
Figure 24:
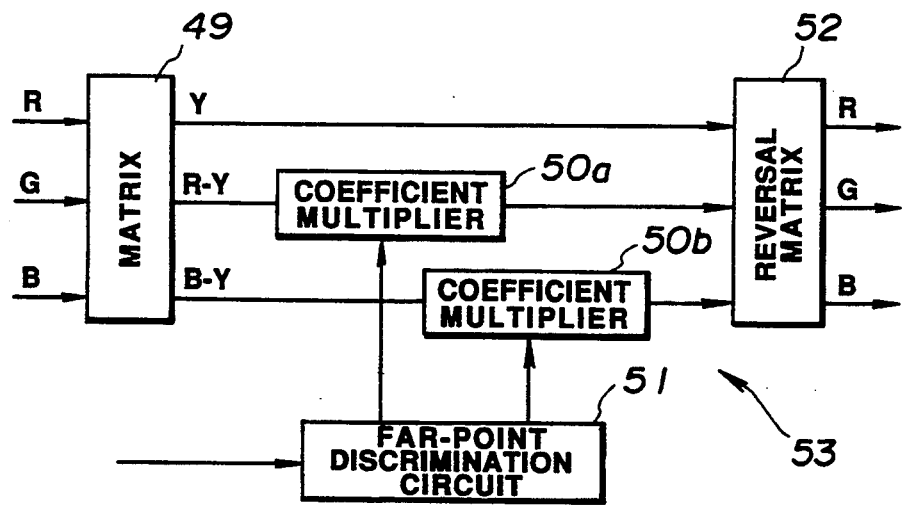
Figure 25:
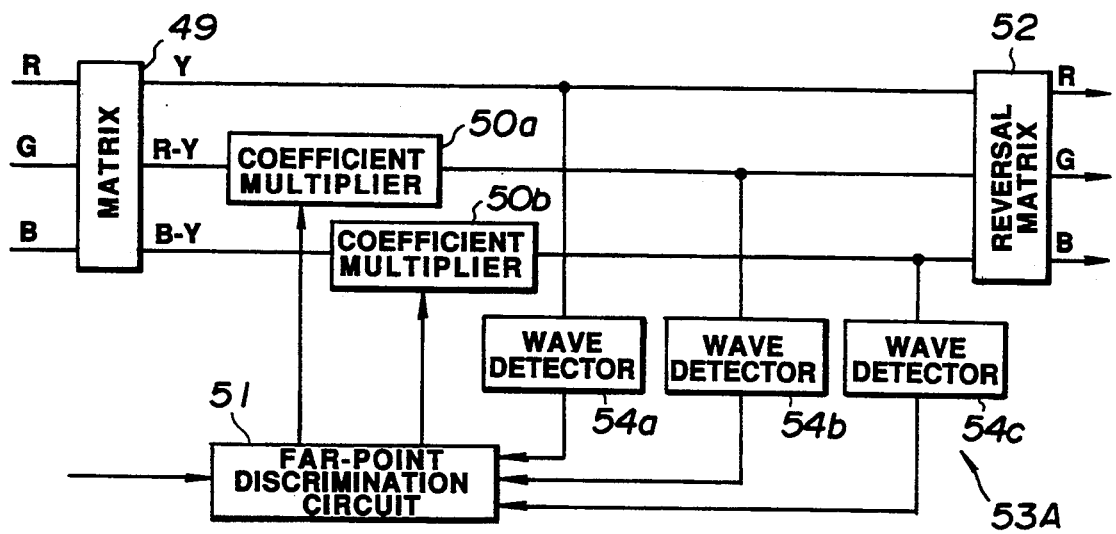
Figure 26:
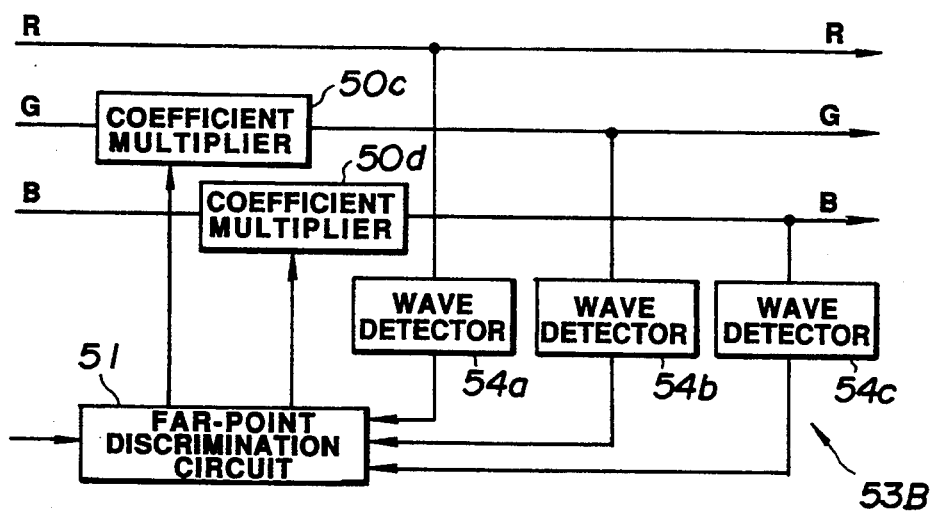

FIGS. 23 to 26 relate to a seventh embodiment of the present invention. FIG. 23 is an overall structural view which illustrates an electronic endoscope apparatus. FIG. 24 is a block diaphragm which illustrates an example of the structure of a video signal processing circuit. FIG. 25 is a block diagram which illustrates another example of the structure of the video signal processing circuit. FIG. 26 is a block diagram which illustrates another example of the structure of the video signal processing circuit.

This embodiment has an arrangement that a diaphragm 47 for adjusting the quantity of irradiation light emitted from the lamp 16 is provided for the light source device 3 according to the first embodiment. The diaphragm 47 controls the quantity of light to be made incident upon the light guide 11 so as to obtain an optimum video signal level.

This embodiment is constituted such that information about the position of the diaphragm 47 is used to detect the distance from the subject to the leading portion of the endoscope. In accordance with the result of the detection, the operation of the color signal processing means of the video signal processing circuit 9 is changed.

As shown in FIG. 23, the position of the diaphragm 47 is detected by a diaphragm position detector 48 and the result of the detection is transmitted to the discrimination signal generator 18. The discrimination signal generator 18 previously stores information about the color change corresponding to the diaphragm position for example. The discrimination signal generator 18 transmits a discrimination signal corresponding to information about the color change. The discrimination circuit 19 in the processor 4 converts a signal supplied from the discrimination signal generator 18 into a color conversion signal and transmits the color conversion signal to the video signal processing circuit 9. The same structures and operations as those according to the first embodiment are given the same reference numerals and their descriptions are omitted here.

In the foregoing structure, the main lamp 16 of the light source device 3 usually emits irradiation light. Irradiation light emitted from the main lamp 16 is passed through the light guide 11, followed by irradiation of the subject with light through the leading portion of the endoscope. The subject is imaged on the solid-state image sensing device 13 by the objective lens 12. The subject image is converted into an electric signal by the solid-state image sensing device 13, and then it is transmitted to the processor 4. As a result, the image is processed by the video signal processing circuit 9.

The position of the diaphragm 47 is detected by the diaphragm position detector 48, and information about the diaphragm position is transmitted to the discrimination signal generator 18. The discrimination signal generator 18 transmits a discrimination signal denoting the result of the discrimination of the color change corresponding to the position of the diaphragm 47. In the processor 4 which has received the discrimination signal, the discrimination circuit 19 converts the signal supplied from the discrimination signal generator 18 into a color conversion signal and transmits the color conversion signal to the video-signal processing circuit 9.

The video signal processing circuit 9 includes a color correction circuit 53 to correct the color in response to an output signal from the discrimination circuit 19.

FIG. 2 illustrates a first example of the color correction circuit 53. For example, R, G and B signals received by the color correction circuit 53 are converted into Y, R-Y and B-Y signals by a matrix circuit 49. Then, the signals are multiplied by coefficients by coefficient multipliers 50a and 50b so that the levels of the signals are converted.

The discrimination circuit 19 discriminates the distance from the subject and supplies a discrimination signal about the distance to a far-point discrimination circuit 51. The far-point discrimination circuit 51 sets the coefficients for the coefficient multipliers 50a and 50b in accordance with the result of the discrimination made by the discrimination signal generator 19.

With the electronic endoscope, the observation is performed by irradiating a subject with light emitted through the light emission end of the light guide 11 in the leading portion of the endoscope. Therefore, in a case where the leading portion of the endoscope is positioned adjacently to a subject, a picked-up image is brightened up. Therefore, the diaphragm 47 is adjusted by a light regulation circuit (omitted from illustration) so that light regulation control is performed in such a manner that light emitted from the light source is diaphragmed. If the leading portion of the endoscope is positioned distant from the subject, the image is darkened. Accordingly, light regulation control is so performed that the quantity of light emitted from the light source is enlarged (the diaphragm of the light source is opened). By using diaphragm position information detected by the diaphragm position detector 48, the distance from the subject to the leading portion can be detected. It should be noted that the detection of the diaphragm position may be performed by using a light regulation control signal transmitted from the light regulation circuit to the diaphragm 47.

In accordance with the diaphragm position information, the far-point discrimination circuit 51 detects the distance from the subject to discriminate whether or not the subject is at a far point. The far-point discrimination circuit 51 transmits control signals to the coefficient multipliers 50a and 50b so that the coefficients for the coefficient multipliers 50a and 50b are set.

The influence of secondary reflected light due to the wall of the internal organ is in proportion to the distance from the subject to the leading portion of the endoscope, causing the color of the subject to be darkened due to the influence of the color of the wall of the internal organ. Therefore, control is performed in this embodiment in such a manner that the levels of the color difference signals R-Y and B-Y are reduced by the coefficient multipliers 50a and 50b in inverse proportion to the distance from the subject to the leading portion of the endoscope. The foregoing control is adaptably performed in a linear or a non-linear manner in accordance with the level of diaphragm position information. As a result, the saturation is corrected when a far-point observation is performed.

The brightness signal Y, color difference signals R-Y and B-Y transmitted from the coefficient multipliers 50a and 50b are again converted into R, G and B signals by a reversal matrix circuit 52. The R, G and B signals are transmitted as output signals from the color correction circuit 53.

As described above, this embodiment is able to reduce the influence of secondary reflected light due to the wall of the internal organ when a far point is observed by performing the color correction by the color correction circuit 53. Therefore, the color level can always optimally be corrected regardless of the distance.

FIG. 25 illustrates a color correction circuit 53A according to a second structural example.

The second structural example is arranged in such a manner that wave detectors are respectively provided for lines for Y, R-Y and B-Y signals in addition to the elements of the first structural example.

R, G and B signals received by the color correction circuit 53A are converted into Y, R-Y and B-Y signals by the matrix circuit 49. Then, the levels are converted by the coefficient multipliers 50a and 50b. Further, a discrimination signal corresponding to the diaphragm position supplied from the discrimination signal generator 19 is supplied to the far-point discrimination circuit 51 similarly to the first structural example.

The wave levels of the Y signal and the R-Y and B-Y signals, which are transmitted from the coefficient multipliers 50a and 50b, are detected (for example, average value is calculated) by wave detectors 54a, 54b and 54c to be supplied to the far-point discrimination circuit 51.

Similarly to the first structural example, the far-point discrimination circuit 51 detects the distance from the subject to the leading portion of the endoscope in accordance with an output signal from the discrimination circuit 19 which corresponds to the diaphragm position signal.

If the distance from the subject to the leading portion is short, the influence of secondary reflected light is not significant and, therefore, the color balance does not deteriorate. Therefore, the output values from the wave detectors 54a, 54b and 54c are held in the far-point discrimination circuit 51 in a case where the distance from the subject to the leading portion is included in a predetermined short range. Even if the distance from the subject to the leading portion is long, the coefficient multipliers 50a and 50b are so controlled that the ratio of the wave detectors 54a, 54b and 54c is the same as the ratio of the held outputs from the wave detectors 54a, 54b and 54c.

As a result of the foregoing control, the ratio of the Y, R-Y and B-Y signals can be maintained regardless of the distance from the subject similarly to the case where the distance from the subject to the leading portion is short. Therefore, the influence of secondary reflected light can be reduced. Hence, the color level can always optimally be corrected regardless of the distance.

The brightness signal Y and the color difference signals R-Y and B-Y transmitted from the coefficient multipliers 50a and 50b are converted into R, G and B signals by the reversal matrix circuit 52 to be transmitted as output signals from the color correction circuit 53A.

Although the first and second structural examples of the color correction circuit has an arrangement that the reversal matrix circuit 52 generates the R, G and B signals from the Y, R-Y and B-Y signals, an arrangement may be employed in which the matrix circuit 49 performs conversions to the G, R-Y and B-Y signals and the reversal matrix circuit 52 synthesizes the R, G and B signals from the G, R-Y and B-Y signals.

FIG. 26 illustrates a color correction circuit 53B according to a third structural example.

The third structural example is structured so that no matrix circuit is provided. The R and B signals among the R, G and B signals received by the color correction circuit 53B are then received by the coefficient multipliers 50c and 50d so that their levels are converted. Similarly to the first structural example, the output signal from the discrimination circuit 19 is received by the far-point discrimination circuit 51. The levels of the G signal and the R and B signals, which are the outputs from the coefficient multipliers 50c and 50d, respectively are wave-detected by the wave detectors 54a, 54b and 54c (for example, the average value is calculated) to be supplied to the far-point discrimination circuit 51A.

The far-point discrimination circuit 51 detects the distance from the subject to the leading portion of the endoscope in accordance with the result of the discrimination of the diaphragm position similarly to the first structural example. Similarly to the second structural example, the far-point discrimination circuit 51 holds the output values from the wave detectors 54a, 54b and 54c if the distance from the subject to the leading portion is included in a predetermined short range. Even if the distance from the subject to the leading portion of the endoscope is elongated, the coefficient multipliers 50c and 50d are controlled so that the ratio of the wave detectors 54a, 54b and 54c is the same as the ratio of the held outputs from the wave detectors 54a, 54b and 54c.

As a result of the foregoing control, the ratio of the G, R and B signals can be maintained similarly to the case where the distance from the subject to the leading portion is short regardless of the distance from the subject. Therefore, the influence of secondary reflected light can be reduced. Hence, the color level can always optimally be corrected regardless of the distance.

Since the third structural example enables the R, G and B signals to be processed as it is, the matrix circuit, which is required for a processing method of a type performing the conversion to the color difference signal, can be omitted. Therefore, an advantage can be realized in that the circuit structure can be simplified. Since the ratio of the R, G and B signals is controlled, a further precise correction can be performed as compared with a method in which the saturation is simply controlled.

Although the third structural example has the arrangement that only the levels of the R and B signals are controlled, an arrangement may be employed in which a coefficient multiplier is also provided for the G signal and the levels of the R, G and B signals are controlled.

Although the second and the third structural examples have the arrangement that the signal levels are controlled to make the ratio to be the same as the ratio of the signals in the case where the subject is positioned nearby, control may be so performed that the ratio of the colors is changed in accordance with the distance.

Figure 27:
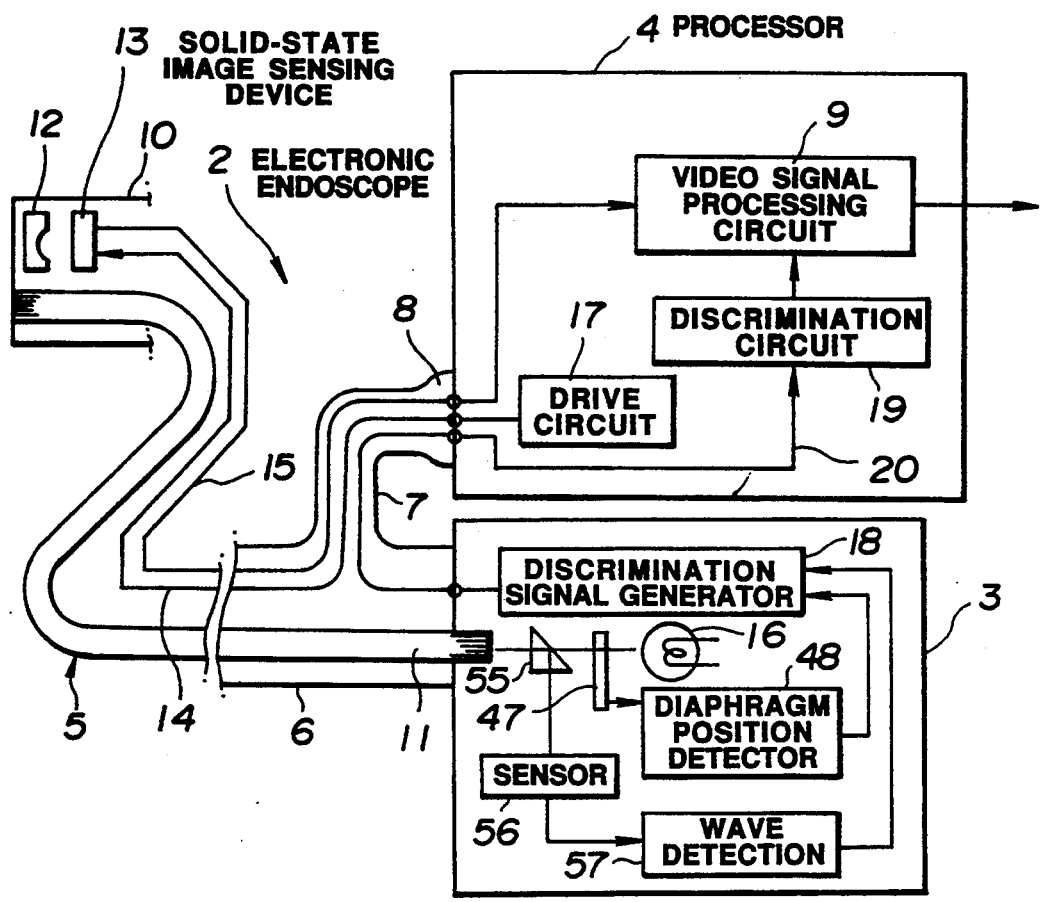
FIGS. 27 and 28 relate to an eighth embodiment.
Figure 28:
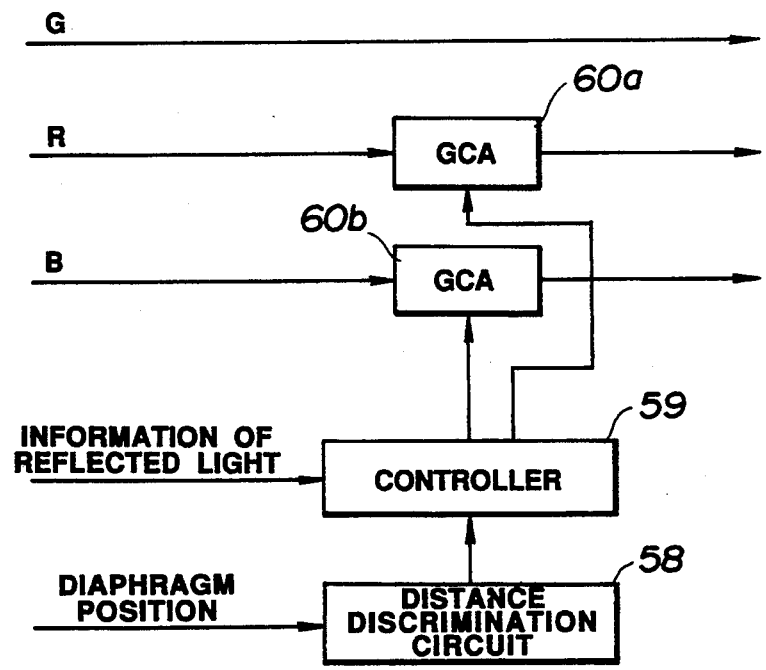

FIGS. 27 and 28 relate to an eighth embodiment of the present invention. FIG. 27 is an overall structure view which illustrates an electronic endoscope apparatus. FIG. 28 is a block diagram which illustrates an example of the structure of a video signal processing circuit.

The apparatus according to this example is structured so that light reflected from a subject and returned from the leading portion of the endoscope through the light guide is separated in the light source portion, the color of the subject, for example, the inner wall of an internal organ is detected, and the result of the detection is color-corrected as a secondary reflected light component.

The same structures and operations as those according to the seventh embodiment are given the same reference numerals and their descriptions are omitted here.

Irradiation light emitted from the main lamp 16 is passed through the diaphragm 47, a beam splitter 55 and the light guide 11 and applied to a subject through the leading portion of the endoscope. The subject is imaged on the solid-state image sensing device 13 by the objective lens 12 and converted into an electric signal by the solid-state image sensing device 13 to be transmitted to the processor 4. The electric signal is processed by the video signal processing circuit 9 of the processor 4. The position of the diaphragm 47 is detected by the diaphragm position detector 48 and the result of the detection is supplied to the discrimination signal generator 18.

Light emitted from the leading end of the endoscope is applied to the subject and reflected. Reflected light is again passed through the light guide 11 to be returned to the light source device 3. Returned light is separated by the beam splitter 55 and detected by the sensor 56.

A signal detected by the sensor 56 is subjected to a detection for obtaining component ratio of R, G and B by the wave detection circuit 57. The result of the component detection is supplied to the discrimination signal generator 18. The detected signal is obtained by averaging reflected light emitted through the light guide 11. Therefore, it can be said that the signal denotes the color of the overall wall of the internal organ in a case of a medical endoscope.

The discrimination signal generator 18 shown in FIG. 27 synthesizes diaphragm position information and reflected light information to transmit the result of the synthesis to the processor 4. The discrimination circuit 19 of the processor 4 again separates the signal transmitted from the light source into the diaphragm position information and reflected light information to transmit the separated information to the video signal processing circuit 9.

FIG. 28 is a block diagram relating to an example of the structure of a color correction circuit of the video signal processing circuit 9. The color correction circuit shown in FIG. 28 supplies the separated diaphragm position information to a distance discrimination circuit 58. The distance discrimination circuit 58 estimates the distance from the leading portion of the endoscope to a subject in accordance with the diaphragm position. The distance information and information about reflected light returned through the light guide 11 are used by the controller 59 to control the gains of a GCA (Gain Control Amplifier) 60a and a GCA 60b.

A method of controlling the gain will now be described.

Assuming that the RGB ratio of the reflected light information is R:G:B=r:g:b, the gains GR and GB of the GCA 60a and GCA 60b are as follows:

$$GR = k\ (g/r)$$

$$GB = l\ (g/b)$$

where k is a parameter which is (r/g) when the distance information is zero and which approaches "1" when the distance is elongated, and l is a parameter which is (b/g) when the distance information is zero and which approaches "1" when the distance is elongated. The change ratios of k and l corresponding to the distance are determined in accordance with the characteristics of the subject for the inspection and conditions of the endoscope.

That is, GR and GB are set to approach "1" and the quantity of the correction is reduced if the distance is short (if the influence of secondary reflected light is not significant). If the distance is long (if the influence of secondary reflected light is significant), the correction is performed considerably in accordance with the reflected light information.

This embodiment is able to reduce the influence of secondary reflected light from a subject.

Figure 29:
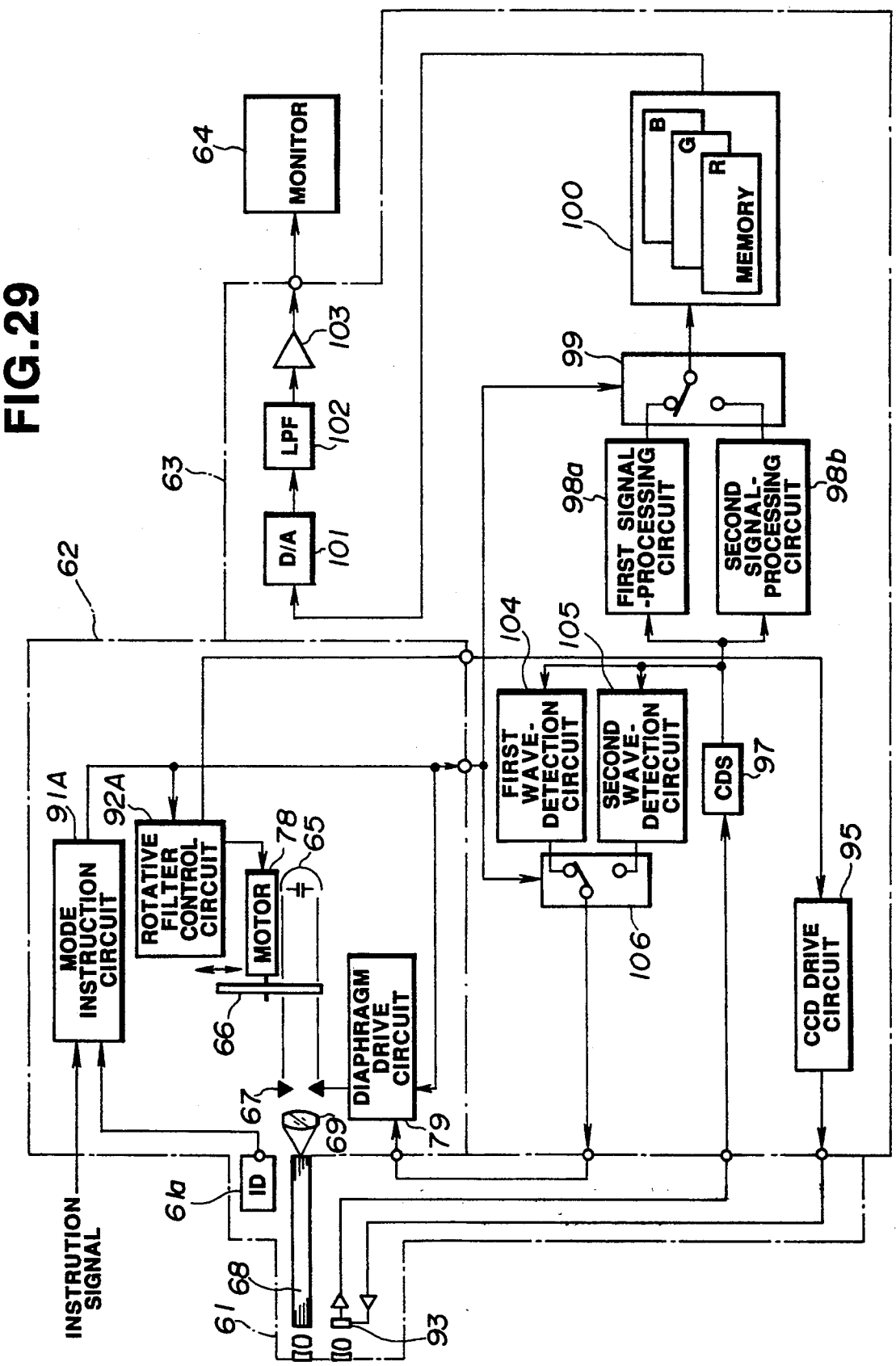
FIGS. 29 to 34 relate to a ninth embodiment.
Figure 30:
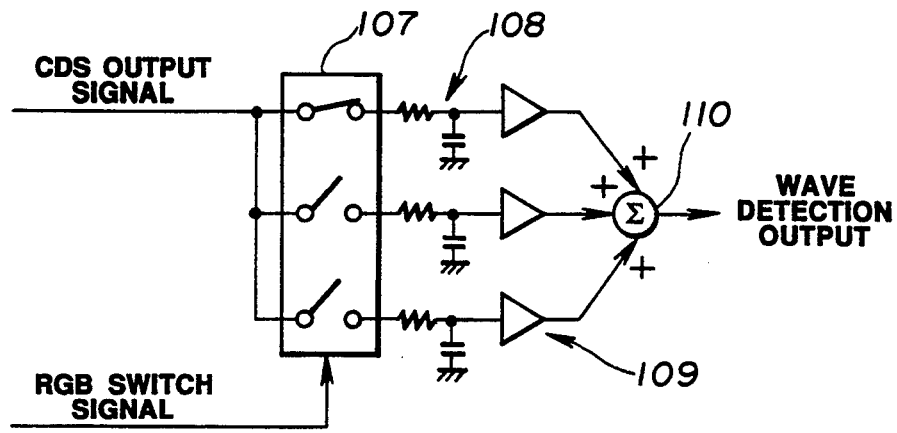
Figure 31:
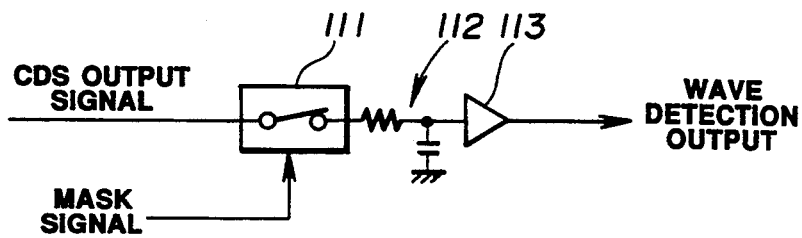
Figure 32:
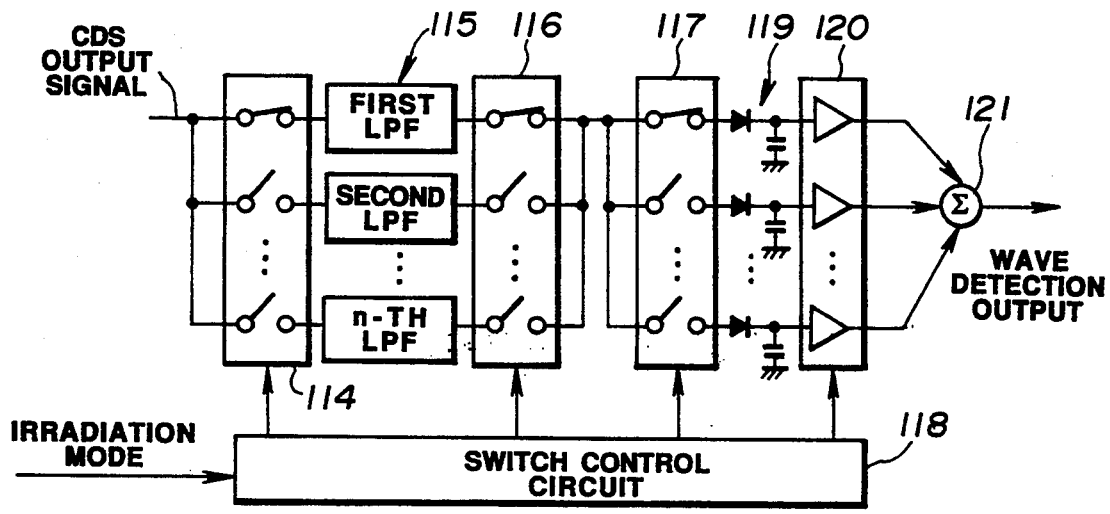
Figure 33:
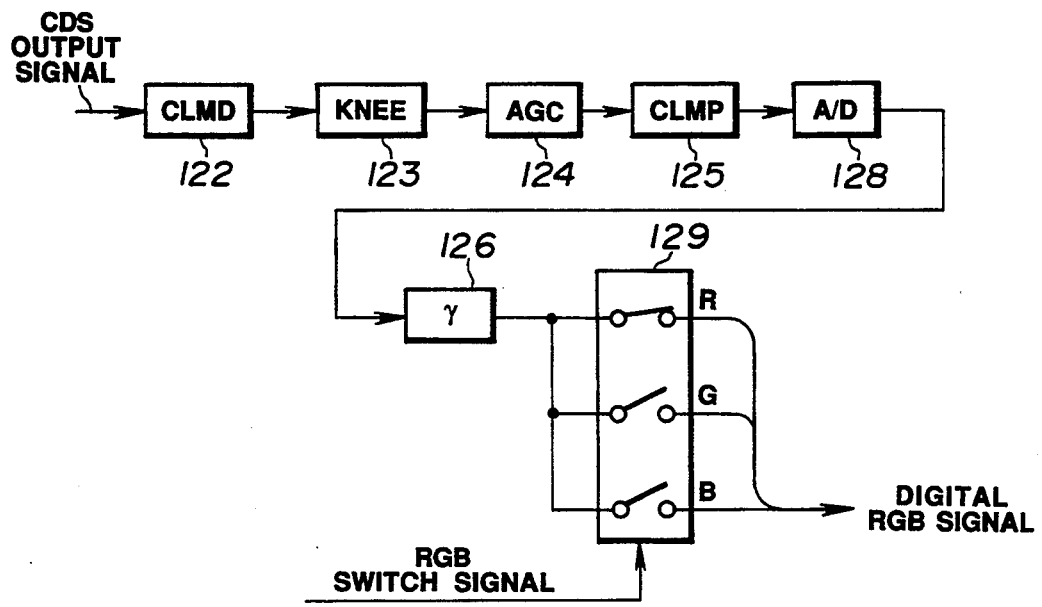
Figure 34:
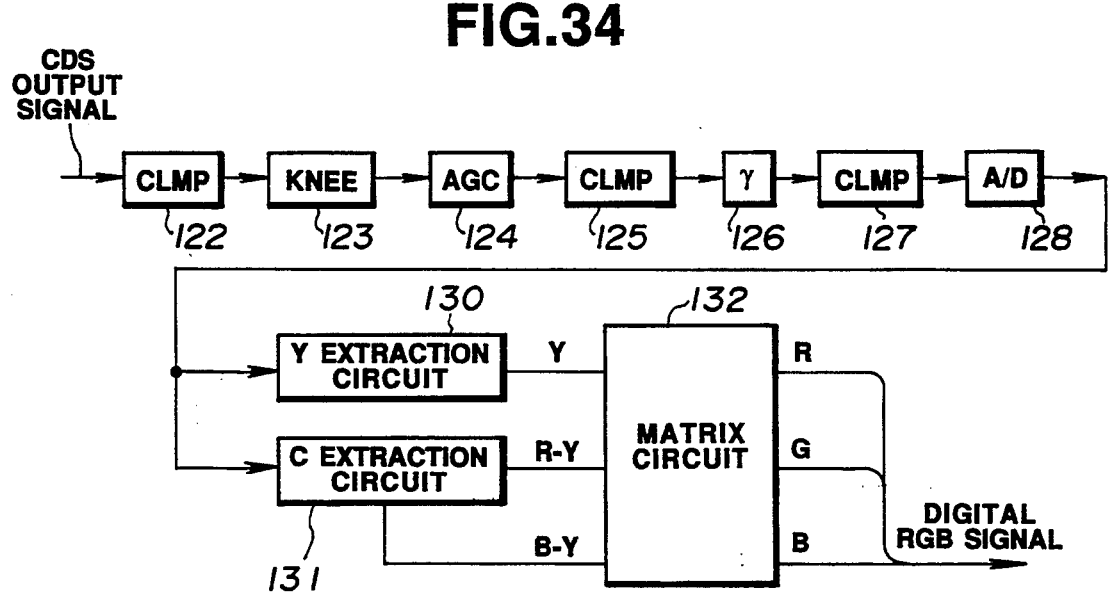

FIGS. 29 to 34 relate to a ninth embodiment of the present invention. FIG. 29 is an overall structural view of an electronic endoscope apparatus. FIG. 30 is a circuit diagram which illustrates a first wave-detection circuit adaptable to the plane sequential imaging method. FIG. 31 is a circuit diagram which illustrates a second wave-detection circuit adaptable to the simultaneous method. FIG. 32 is a circuit diagram which illustrates a wave detection circuit adaptable to a plurality of irradiation modes. FIG. 33 is a block diagram which illustrates a first signal processing circuit. FIG. 34 is a block diagram which illustrates a second signal processing circuit.

The electronic endoscope apparatus shown in FIG. 29 comprises an endoscope 61, a light source device 62, a processor 63 and a monitor 65.

The light source device 62 converts white light emitted from a light source lamp 65 into RGB sequential irradiation light by its RGB rotative filter 66, and converges light onto the end surface of the light guide 68 of the endoscope 61 by a light converging lens 69 via a diaphragm 67 which regulates light in response to a light regulation signal supplied from the processor 63. The rotative filter 66 is rotated by a motor 78. The quantity of the diaphragm realized by the diaphragm 67 is controlled by a diaphragm drive circuit 79.

The light source device 62 comprises an irradiation mode instruction circuit 91A for transmitting an instruction signal in response to an ID signal supplied from an ID generating portion 61a of the endoscope 61 or in accordance with the operation of an instruction switch (omitted from illustration) of a light source control panel. The light source device 62 further comprises a rotative filter control circuit 92A for controlling the rotative filter 66 in response to the instruction signal.

In response to the instruction signal supplied from the irradiation mode instruction circuit 91A, the rotative filter control circuit 92A inserts/removes a rotative filter 78 to and from the optical path. The diaphragm drive circuit 79 changes the gain and the frequency characteristics and so forth. Simultaneously, the irradiation mode instruction circuit 91A transmits, to the processor 63, an instruction signal denoting the irradiation mode.

If the plane sequential irradiation mode is selected by using the control panel of the light source device 62, the rotative filter 66 is rotated at a predetermined speed and inserted into a predetermined position in the optical path so that the plane sequential irradiation is realized. If the simultaneous (a single-plate method) irradiation mode is selected, the rotative filter 66 is removed from the optical path so that a continuous white light source is realized.

Usually, the light source irradiation mode is made to be the plane sequential mode or the simultaneous mode by inserting/removing a filter array of a solid-state image sensing device mounted on the endoscope apparatus. Therefore, the endoscope apparatus is automatically set to a desired mode in response to a signal supplied from the ID generating portion 61a provided for the endoscope 61. That is, the endoscope can be attached/detached to and from the light source device and the processor. Therefore, any electronic endoscope may be-changed and used regardless of the fact that the electronic endoscope is adapted to the plane sequential imaging method or the simultaneous imaging method.

A special case can be considered that change over to the plane sequential irradiation is performed in accordance with an instruction issued by using the control panel during a usual observation performed with an endoscope adapted to the simultaneous method, and the RGB component ratio of a specific portion of the image is obtained to extract the characteristics of the portion to be observed. In this case, the transparent characteristics of the filter array with respect to each of R, G and B component light generates a fringe pattern in the picked-up image. However, the level of the generated pattern does not obstruct the practical observation.

The processor 63 comprises a CCD drive circuit 95 for driving a solid-state image sensing device (for example, a CCD) 93 of an endoscope 62 and a CDS (Correlative Double Sampling) circuit 97 for suppressing 1/f noise of an electric signal transmitted from the solid-state image sensing device 93. The processor 63 comprises first and second signal processing circuits 98a and 98b and a switch circuit 99 for processing the output from the CDS circuit 97 to correspond to a plurality of irradiation modes, that is, the imaging modes and capable of switching the output. Further, the processor 63 comprises an RGB memory circuit 100 for storing the output selected by the switch circuit 99, a D/A conversion circuit 101, a low-pass filter (LPF) circuit 102 and a video buffer circuit 103 to transmit the signal denoting the endoscope image to the monitor 64.

The processor 63 comprises first and second wave detection circuits 104 and 105 and a switch circuit 106, the first and second wave detection circuits 104 and 105 being so provided as to be changed over to correspond to the irradiation mode of the light source and adapted to different methods.

An image signal supplied from the solid-state image sensing device 93 is converted into a base band signal by the CDS circuit 97 to be received by the first and second wave detection circuits 104 and 105 and the first and second signal processing circuits 98a and 98b. In response to the irradiation mode signal supplied from the light source device 62, the first wave detection circuit 104 or the second wave detection circuit 105 is selected to transmit a light regulation signal to the diaphragm drive circuit 79 of the light source. In response to the foregoing irradiation mode signal, the first signal processing circuit 98a or the second signal processing circuit 98b is selected to subject the image signal converted into the base band to a predetermined process. Then, the image signal is stored in the RGB memory 100. Image data items stored in the memory 100 are simultaneously read out in synchronization with a standard TV signal to be D/A-converted. Then, the band of the D/A-converted signal is limited by the low-pass filter 102 to be transmitted to an external monitor 64 via the video buffer 103.

FIG. 30 illustrates a structural example of the first wave detection circuit 104 adapted to the plane sequential imaging method. The CDS output signals are signals for R, G and B image periods and are, by the switch circuit 107, distributed to a plurality of LPF/hold circuits 108 each comprising a resistor and a capacitor. The LPF/hold circuits 108 hold the average values of R, G and B images. The average values of RGB images are respectively multiplied by coefficients by a plurality of coefficient multipliers/buffers 109. Then, they are added by an adder 110 to be transmitted. By making the ratio of R, G and B to be about 1:2:1 at this time, the first wave detection circuit 104 is able to make its output as a wave detection signal denoting brightness component Y of the image.

FIG. 31 illustrates a structural example of the second wave detection circuit 105 adapted to the simultaneous method. The second wave detection circuit 105 shown in FIG. 31 integrates and holds the signals for the image periods of the CDS output by its LPF/hold circuit 112 comprising a resistor and a capacitor to generate a detection signal denoting brightness component Y. The detection signal is transmitted via a buffer 113. The switch circuit 111 which is opened/closed in response to a mask signal is switched off in the periods except for the foregoing image period.

FIG. 32 illustrates an example of the structure of a circuit which enables the first and second wave detection circuits 104 and 105 to be changed over to be adaptable to two or more irradiation modes.

The circuit shown in FIG. 32 comprises n different LPF circuits 115 so provided as to be changed over to be adaptable to the irradiation mode of the light source, n peak hold circuits 119 so provided as to be changed over in response to plane sequential image signals such as R, G and B signals, n coefficient multipliers/buffers 120 and an adder 121 for adding n outputs from the coefficient multipliers/buffers 120.

The circuit shown in FIG. 32 has switch circuits 114 and 116 each comprising n switches and connected to positions across the LPF circuit 115. Further, a switch circuit 117 comprising n switches is connected to a position in the rear of the peak hold circuit 119.

The switch circuits 114, 116 and 117 and coefficient multipliers/buffers 120 are controlled to be opened/closed in response to the irradiation mode signal by the switch control circuit 118.

The foregoing structure enables the light regulation wave detection method of the processor 63 to be properly selected to be adaptable to the combination of the light source device 62 and the endoscope 61.

In a case where an endoscope comprising a solid-state image sensing device having a small number of pixels is used, the LPF of the wave detection circuit having a small time constant is selected. In a case where an endoscope having a large number of pixels is used, the LPF having a large time constant is selected.

In a case where the gain of the diaphragm drive circuit 79 must be set to a different value to be adaptable to the different irradiation mode of the light source, the degree of amplification of the coefficient multiplier/buffer is changed in response to the irradiation mode signal.

FIGS. 33 and 34 illustrate examples of the structure of the first and second signal processing circuits 98a and 98b. In the circuits 98a and 98b, CLMP (clamp) circuits 122, 125 and 127 are circuits for DC-reproducing the CDS output signals or the like. A KNEE circuit is a 1-broken-line-type non-linear circuit for lowering the degree of amplification if the supplied signal has a level higher than a predetermined level. An AGC circuit is a circuit for automatically controlling the gain.

Reference numeral $\gamma 126$ represents a gamma correction circuit. The gamma correction circuit $\gamma 126$ shown in FIG. 33 can be realized by a digital circuit using a look-up table ROM. A circuit 126 shown in FIG. 34 can be realized by an analog-type composite gamma correction circuit for changing the gain in accordance with the level of the brightness component contained in the signal.

In the circuit shown in FIG. 33, a plane sequential signal subjected to the $\gamma$-correction is distributed and transmitted to each of R, G and B data bus by the switch circuit 129. In the circuit shown in FIG. 34, Y-extraction circuits 130 and 131 extract the brightness component and the color difference component from the CCD image signal which has been A/D-converted, and then a matrix circuit 132 performs conversion to R, G and B signals to transmit them.

This embodiment enable the wave detection method for the automatic light regulation to be automatically and properly changed over to be adaptable to the irradiation mode of the light source. Further, this embodiment enables the wave detection method for the automatic light regulation to be set by using the control panel. Therefore, even if the change over to an endoscope adapted to a different imaging method or irradiation method is performed, this embodiment enables each component apparatus to be quickly and properly set.

Further, this embodiment enables a simultaneous endoscope to perform a plane sequential observation.

Figure 35:
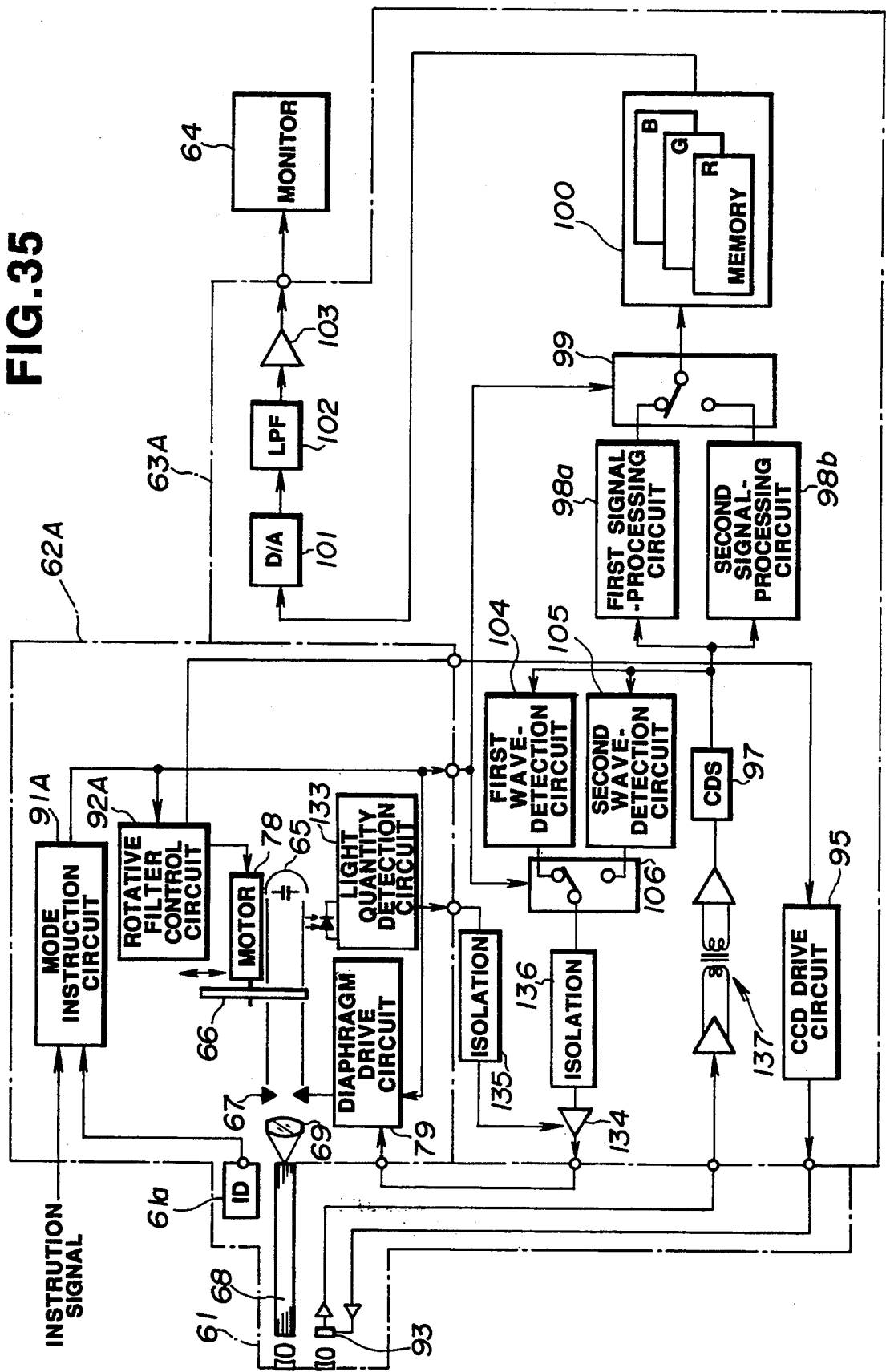
FIG. 35 is an overall structural view which illustrates an electronic endoscope apparatus according to a tenth embodiment.

FIG. 35 is an overall structural view which illustrates an electronic endoscope apparatus according to a tenth embodiment of the present invention.

A light source device 62A according to this embodiment comprises a light quantity detection circuit 133 in addition to the elements of the light source device 62 according to the ninth embodiment. In addition to the elements of the processor 63A according to the ninth embodiment, a processor 63A according to this embodiment comprises a GCA (Gain Control Amplifier) 134 for varying the gain of each of wave detection outputs from the first and second wave detection circuits 104 and 105. The light quantity detection circuit 133 detects the light quantity by using a portion of light emitted from the lamp 65 to control the gain of the GCA 134 via an isolation 135.

The wave detection outputs are supplied to the GCA 134 via an isolation 136. The output from the solid-state image sensing device 93 is supplied to the CDS circuit 97 via an isolation portion 137. The same structures and operations as those according to the ninth embodiment are given the same reference numerals and their descriptions are omitted here.

In the foregoing structure, a rotative filter control circuit 92A of the light source device 62A determines the operational mode in accordance with the ID of the connected endoscope and with an instruction issued through the control panel so that insertion/removal of the rotative filter 66 to and from the optical path and the rotational speed and the phase of the rotative filter 66 are controlled. Simultaneously, the irradiation mode signal is supplied to the diaphragm drive circuit 79 for adjusting the quantity of light to be emitted, the irradiation mode signal being also supplied to the processor 63A. The switch circuits 99 and 106 select the wave detection circuit and the signal processing circuit in response to the irradiation mode signal.

The rotative filter control circuit 92A transmits information about the phase, the speed, and insertion/removal of the rotative filter to a CCD drive circuit 95. The CCD drive circuit 95 adaptably drives the solid-state image sensing device 93 in accordance with the information about the phase, the speed, and insertion/removal of the rotative filter.

In accordance with the irradiation mode of the light source, the wave detection circuits generate light regulation control signals and vary the degree of amplification of a light regulation control signal in accordance with information about the light quantity of the light source.

Since this embodiment has the arrangement that the light quantity of the light source lamp is detected and the degree of amplification of the light regulation control signal is adaptably changed in accordance with the detected value, light from a new lamp emitting a large light quantity and that from a lamp emitting a halved light quantity due to substantial completion of its life can be regulated satisfactorily without hunting and response delay.

FIGS. 36 to 38 relate to an eleventh embodiment of the present invention. FIG. 36 is a block diagram which illustrates the schematic structure of an electronic endoscope apparatus. FIG. 37 is a table which illustrates the relationship between set AGC gains and outline highlighting levels in the electronic endoscope apparatus. FIG. 38 is an explanatory view relating to change over of the outline highlighting level.

The electronic endoscope apparatus according to this embodiment is so structured that, if the detected light quantity of the lamp is larger than a predetermined quantity, a plurality of factors, such as setting of the processor, the AGC and the outline highlighting level, are simultaneously changed.

The electronic endoscope apparatus shown in FIG. 36 comprises an endoscope 140 having a CCD 141 serving as an imaging means and a light guide 142 for suppling irradiation light, a light source device 143 for supplying irradiation light to the endoscope 140 and a processor 144 for generating a video signal by processing the image signal supplied from the CCD 141.

In FIG. 36, an image signal of a subject read from the CCD 141 is received by the processor 144. The processor 144 demodulates an output signal from the CCD 141 by a pre-processing circuit 145 thereof, and then transmits it as a video signal via an AGC circuit 146, an outline highlighting circuit 147 and a video buffer 148.

The AGC circuit 146 has a maximum-gain setting circuit 149 for limiting its gain range. The maximum-gain setting circuit 149 enables two or more types of gain ranges of the AGC circuit 146 to be set. The change over of the gain range is performed in response to a switch signal supplied from a CPU 15. The AGC circuit of the foregoing type is a known circuit.

The outline highlighting circuit 147 is able to change over the outline highlighting level via the CPU 150 in accordance with an instruction issued from, for example, a switch 152 disposed on a panel 151 arranged as shown in FIG. 38 for example. The foregoing technology is also a known technology.

The outline highlighting level is sequentially and repeatedly changed over as L (low)/M (middle)/H (high) as shown in FIG. 38 whenever the switch 152 is depressed.

Light beams generated by a lamp 153 in the light source device 144 are converged by a converging lens 1602 and transmitted to the leading end of the endoscope 140 through the light guide 142. As a result, a subject to be imaged is irradiated with the light beams. A diaphragm blade 154 is interposed into the optical path between the lamp 153 and the light guide 142. The diaphragm blade 154 is controlled by a diaphragm control circuit 156 for receiving the image signal to detect the light quantity of irradiation light so that the quantity of diaphragm of the diaphragm blade 154 is automatically adjusted. The automatic adjustment enables the irradiation light quantity to be controlled optimally.

The irradiation light beams are supplied to a light quantity detection device 157 via, for example, a half mirror 158. The output from the light quantity detection device 157 is supplied to a discrimination circuit 159. The discrimination circuit 159 notifies the CPU 150 a fact that the detected light quantity is smaller than a predetermined value.

The relationship between the AGC circuit 146 and the outline highlighting circuit 147 in the electronic endoscope apparatus constituted as described above will now be described with reference to FIG. 37.

If a usual light quantity is obtained from the lamp, the operational gain range of the AGC circuit 146 is set to a low value, for example, 9 dB. As for the outline highlighting circuit 147, a highlighting level can be selected from, for example, 3/6/9 dB in accordance with the panel setting "L"/"M"/"H" made by a user.

If the lamp has deteriorated or if the main lamp has been changed over to an emergency lamp (omitted from illustration), the detected light quantity is reduced and the output from the discrimination circuit 159 is made active. In this case, the CPU 150 changes the maximum gain of the AGC to, for example, 18 dB to correct the lack of the light quantity. At this time, the outline highlighting level is set to, for example, 0/3/6 dB to correspond to the instructed setting "L"/"M"/"H".

Since this embodiment has the arrangement that the reduction in the quantity of light emitted from the lamp is detected to simultaneously control the AGC gain the outline highlighting level, increase in noise occurring due to the increase in the AGC can be prevented. Therefore, an image can be observed while maintaining excellent image quality.

Since this embodiment has the arrangement that the light quantity of the lamp is directly detected by the light quantity detection device, the influence of the image of the subject can be eliminated. Therefore, if the distance from the subject is changed, the gain range is changed over so that a problem of the change of the image quality and the like can be prevented.

Figure 39:
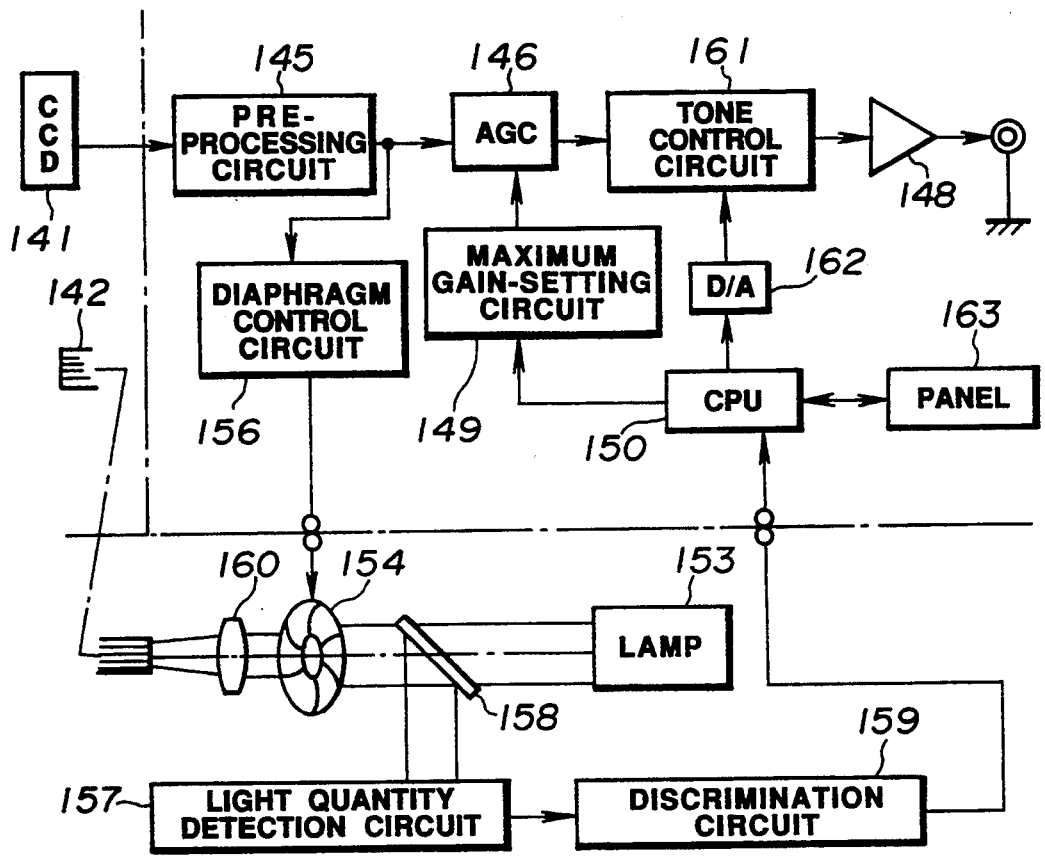
Figure 40:
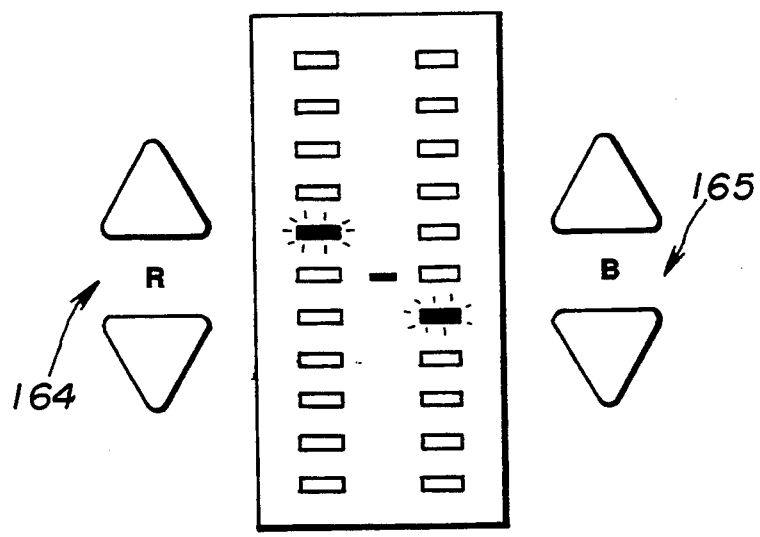

FIGS. 39 to 41 relate to a twelfth embodiment of the present invention. FIG. 39 is a block diagram which illustrates a structure of an electronic endoscope apparatus. FIG. 40 is an explanatory view for explaining change over of the color tone adjustment level. FIG. 41 is a table for showing the relationship between set values of the color tone adjustment and instructed values.

In this embodiment, a color tone adjustment circuit 161 is provided in place of the outline highlighting circuit 147 according to the eleventh embodiment. The same structures and operations as those according to the eleventh embodiment are given the same reference numerals and their descriptions are omitted here. Therefore, the description will be made about only different portions.

The color tone adjustment circuit 161 is able to vary the degree of amplification of, for example, two color signals (R/B) to adjust the color of the output image. Since the foregoing technology is a known technology, its detailed description is omitted. The degree of amplification (instructed value) of the color tone adjustment circuit 161 is supplied from the CPU 150 via a D/A converter 162.

For example as shown in FIG. 40, switches 164 and 165 for instructing the color tone are disposed on the panel 163 so that a user is able to adjust the color tone by operating the switches 164 and 16. The switch 164 corresponds to the color signal R, while the switch 165 corresponds to the color signal B.

At least two combinations of the instruction issued by using the panel 163 and data to be actually transmitted to the D/A converter 162 are stored in the CPU 150. Examples of the foregoing data are shown in tables, FIGS. 41a and 41b. According to this example, the color adjustment can be set by using the panel 163 to steps from +5 to -5 via 0. Each step is provided with an instructed value (a degree of amplification) for each of the color signals R and B.

In this embodiment, the threshold value of the discrimination circuit 159 is set to a lower value than that set in the eleventh embodiment. The reason for this is that lighting of the emergency lamp is solely detected.

The light source for the endoscope is usually arranged so that a xenon lamp is used as the main lamp and a halogen lamp is used as the emergency lamp. Since the emergency lamp is dark as compared with the main lamp, lighting of the emergency lamp can be detected by detecting the light quantity as described above.

In the electronic endoscope apparatus according to this embodiment, the operational gain range of the AGC is set to a low range of, for example, 9 dB when the main lamp is lit as a usual mode.

The actual instructed value of the color tone to be given to the D/A converter 162 with respect to the value of the color tone set by using the panel 163 is set in accordance with, for example, a table shown in FIG. 41a. When a user has instructed a combination, for example, (R, B)=(+1, −1), voltage corresponding to "20" is given to R signal 41a and voltage corresponding to "16" is given to B signal 41b as color tone instruction signals.

If the main lamp is changed over to the emergency lamp due to a failure, the CPU 150 changes the maximum gain of the AGC to, for example, 18 dB so that the lack of the light quantity is corrected. Simultaneously, the color tone instructed value in a table shown in FIG. 41b is used. That is, voltage corresponding to "14" is transmitted to R signal and voltage corresponding to "20" is transmitted to B signal when a combination (R, B)=(+1, −1) is instructed so that the color temperature change of the lamp is corrected.

Since this embodiment has the arrangement that the change over to the emergency lamp is detected to simultaneously control the gain of the AGC and the color tone, a fact that the change in the color taken place due to the change of the color temperature of the light source becomes conspicuous due to the rise in the gain of the AGC can be prevented. As a result, an image can be observed while maintaining an excellent image quality.

Since the light quantity of the lamp is directly detected by the light quantity detection device, the influence of the image of the subject can be eliminated. Therefore, a problem of the change in the color tone or the like can be prevented in a case where, for example, the distance from the subject has been changed.

Figure 42:
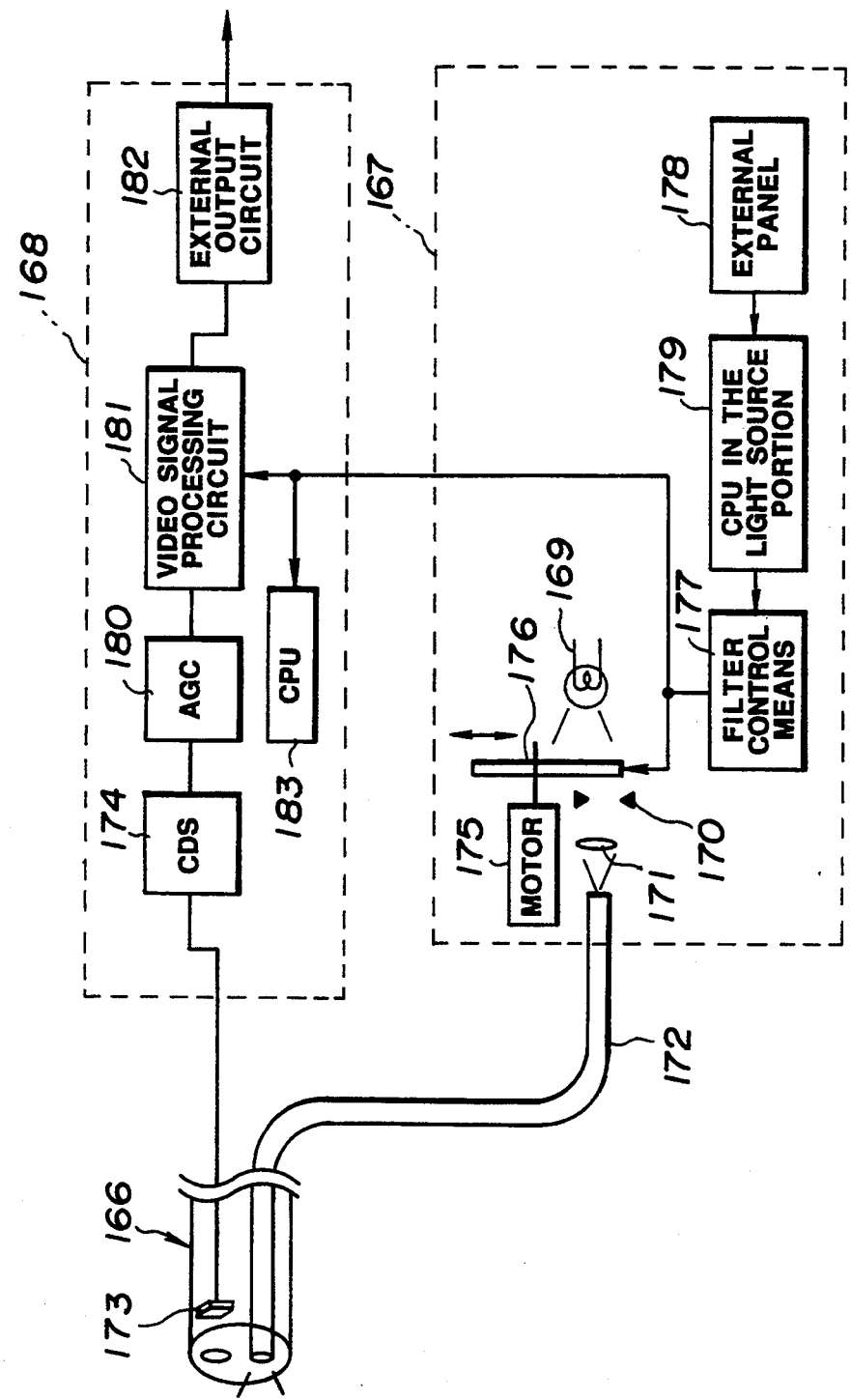
FIGS. 42 to 45 relate to a thirteenth embodiment.
Figure 43:
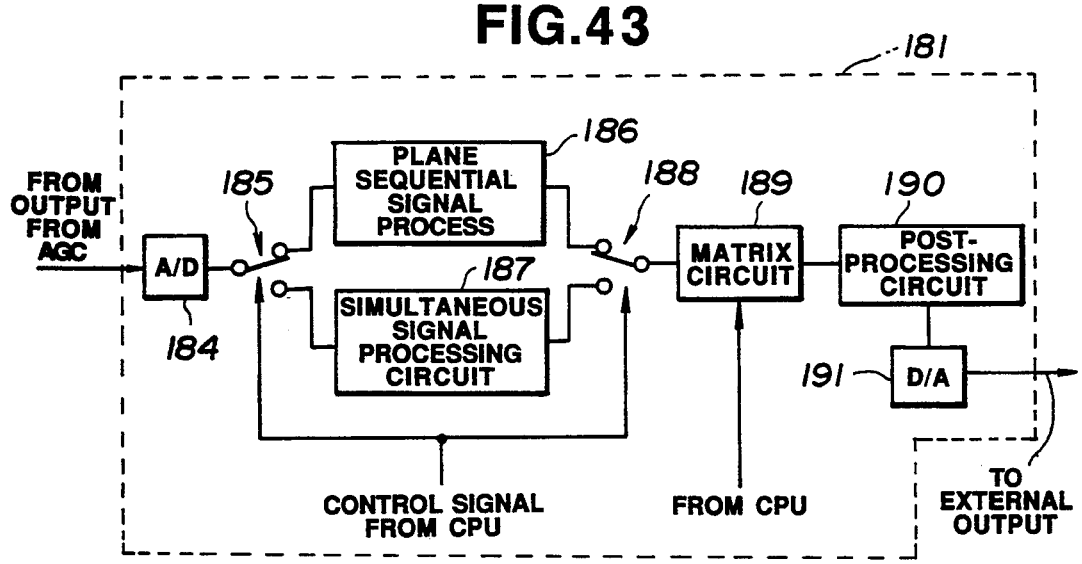
Figure 44:
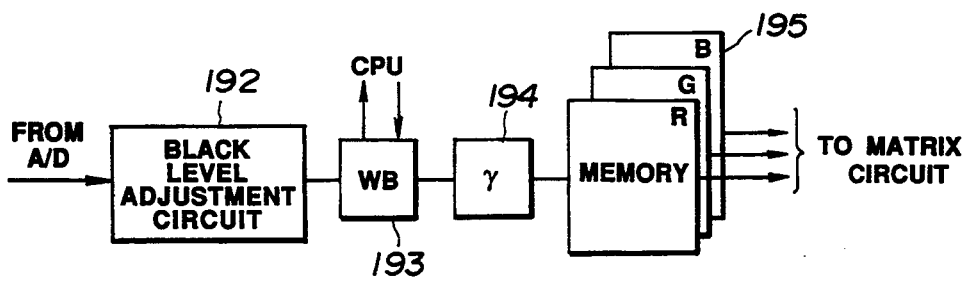
Figure 45:
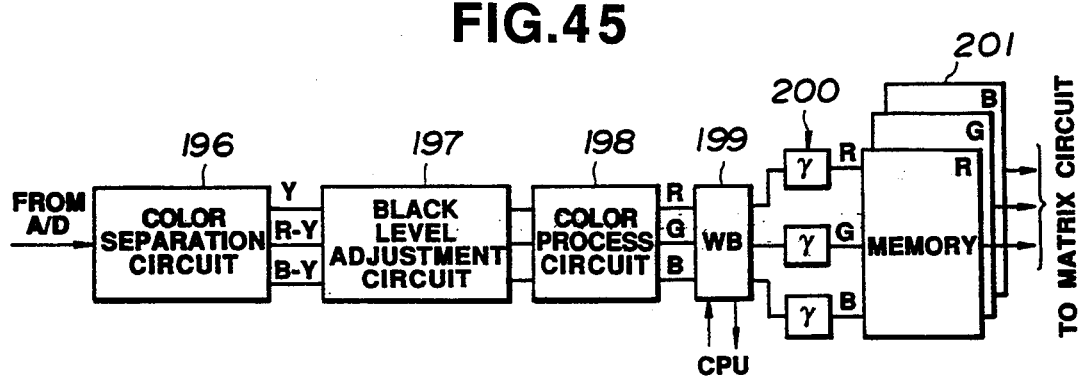

FIGS. 42 to 45 relate to a thirteenth embodiment of the present invention. FIG. 42 is a block diagram which illustrates the schematic structure of an electronic endoscope apparatus. FIG. 43 is a block diagram which illustrates a video signal processing circuit. FIG. 44 is a block diagram which illustrates a simultaneous signal processing circuit. FIG. 45 is a block diagram which illustrates a plane sequentially signal processing circuit.

The electronic endoscope apparatus according to this embodiment is structured so that the signal process performed by the processor is automatically changed over to the plane sequential method or the simultaneous method in accordance with the set mode of the light source device.

An electronic endoscope apparatus shown in FIG. 42 comprises an endoscope 166, a light source unit 167 and a processor unit 168.

Irradiation light generated by a lamp 169 disposed in the light source unit 167 is made incident upon a light guide 172 via a diaphragm 170 and a converging lens 171, each of which is disposed on its optical path. Irradiation light transmitted to the leading portion of the endoscope 166 through the light guide 172 is applied to a subject. The image of the subject irradiated with light is converted into an electric signal by a CCD 173 disposed at the leading portion of the endoscope 166. The electric signal is introduced into a CDS circuit 174 of the processor unit 168 and then transmitted as a video signal via an AGC circuit 180, a video signal processing circuit 181 and an external output circuit 182.

The light source unit 167 includes a rotative filter 176 which is inserted/removed to and from the optical path and which is rotated by a motor 175. The insertion/removal of the rotative filter 176 is controlled by a filter control means 177. That is, the light source unit 167 has two irradiation modes, that is, the plane sequential mode and the simultaneous mode which can be changed over. The irradiation mode is set by using a button (omitted from illustration) of an external panel 178. A CPU 179 disposed in the light source portion transmits, to the filter control means 177, a control signal corresponding to the selected mode to control whether or not the rotative filter 176 is inserted into a position in front of the lamp 169. Further, the CPU 179 in the light source portion transmits, to a CPU 183 in the processor unit 168, a discrimination signal notifying whether or not the rotative filter 176 is present.

The CPU 183 in the processor portion that has received information about the irradiation mode from the light source unit 167 controls the video signal processing circuit 181 to perform a signal processing operation adapted to the irradiation mode. That is, the signal process is performed by either of the plane sequential method or the simultaneous method.

FIG. 181 is a block diagram which illustrates the video signal processing circuit 181. The video signal processing circuit 181 is so structured as to select the plane sequential signal process or the simultaneous signal process in response to the discrimination signal supplied from the light source unit 167.

The video signal processing circuit 181 comprises an A/D converter 184 for receiving the output from the AGC 180, a switch 185, a plane sequential signal processing circuit 186, a simultaneous signal processing circuit 187, a switch 188, a matrix circuit 189, a D/A converter 190 and a post-processing circuit 191.

The plane sequential signal processing circuit 186 and the simultaneous signal processing circuit 187 are disposed in parallel. In front and in the rear of the plane sequential signal processing circuit 186 and the simultaneous signal processing circuit 187, switches 185 and 188 are interposed. The switches 185 and 188 can be changed over in response to a control signal which corresponds to the irradiation mode.

At the time of changing over the mode between the plane sequential mode and the simultaneous mode, the endoscope is usually changed. The endoscope for imaging a subject by the simultaneous method has a color mosaic filter disposed in front of the CCD thereof. The endoscope for imaging a subject by the plane sequential method has no color mosaic filter.

The CPU 183 in the processor portion transmits, to a matrix circuit 189, a coefficient for correcting the difference in the color characteristics between the plane sequential rotative filter 176 and the color mosaic filter of the CCD in the simultaneous mode.

FIG. 44 illustrates an example of the structure of the plane sequential signal processing circuit 186.

In the plane sequential mode, R, G and B sequential signals are supplied to the plane sequential signal processing circuit 186 in a time sequential manner. First, the black level is adjusted by a black level adjustment circuit 192. Then, a white balance (hereinafter abbreviated to W.B) circuit 193 performs a white balance adjustment. The signal subjected to the white balance adjustment is subjected to $\gamma$-correction in a $\gamma$-correction circuit 194 so that R/G/B signals formed by making R, G and B sequential signals to be simultaneous signals in a memory 195 are generated.

FIG. 44 illustrates an example of the structure of the simultaneous signal processing circuit 187.

The circuit 187 is supplied with a color difference sequential signal which is then converted into a brightness signal and a color difference signal in a color separation circuit 196. The brightness signal and the color difference signal are subjected to a black level adjustment in a black level adjustment circuit 197 and converted into R, G and B signals in a color processing circuit 199. The signals converted into R/G/B signals are subjected to the white balance adjustment by a W.B circuit 199. Each of the adjusted signals is subjected to the $\gamma$-correction by a $\gamma$-correction circuit 200 to be transmitted to the matrix circuit 189 via a memory 201.

This embodiment is able to be adapted to two methods, that is, the plane sequential method and the simultaneous method. Further, change over and setting of the method can be performed automatically and easily.

Further, this embodiment has the arrangement that the coefficient of the matrix circuit 189 is changed to be adaptable to the plane sequential/simultaneous mode. As a result, this embodiment is able to be adaptable to the difference in the characteristics between the rotative filter and the color mosaic filter. That is, the color reproducibility can be equally maintained even if the mode is different so that an image which can easily be observed can be provided.

Figure 46:
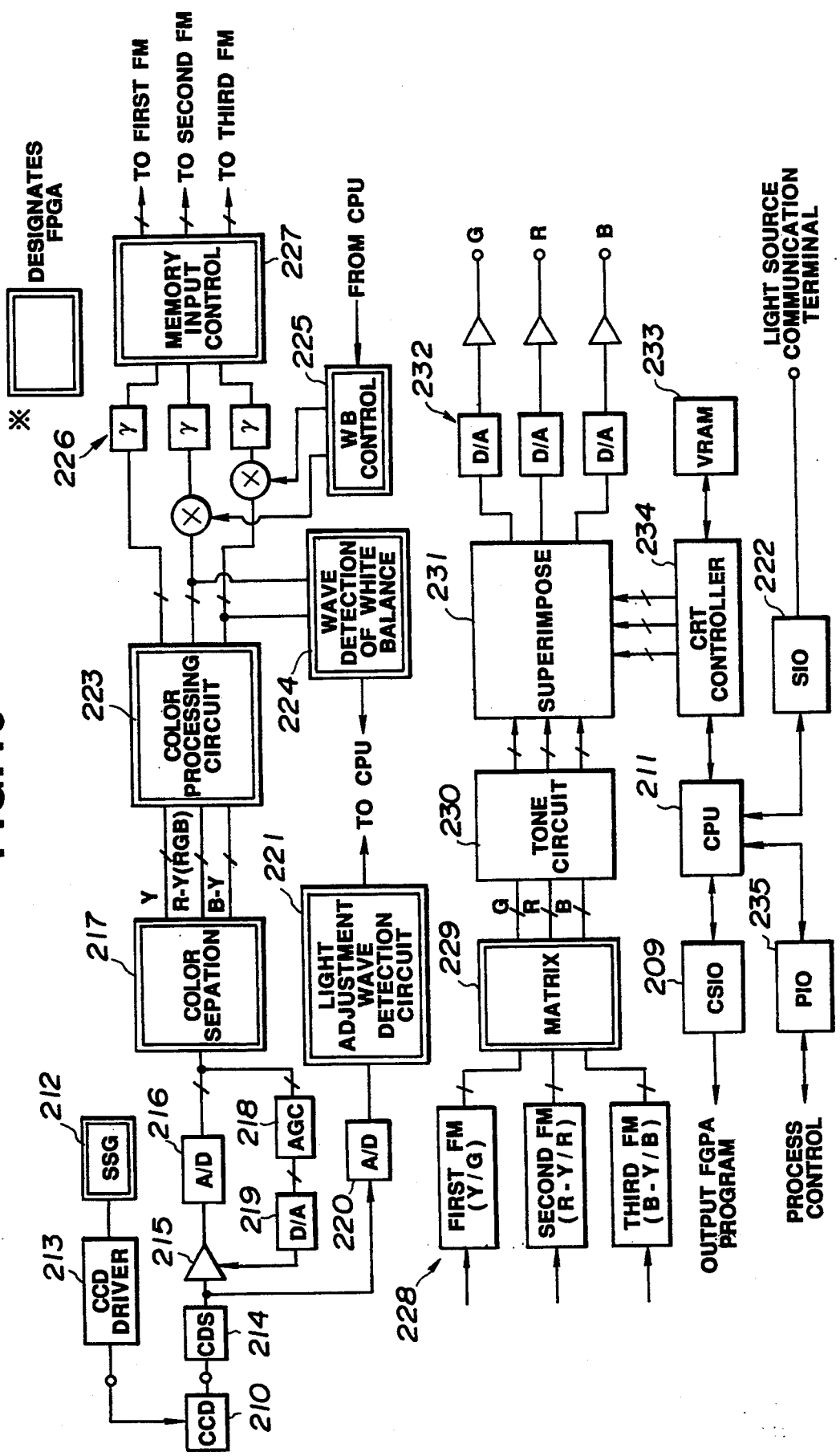
FIGS. 46 to 48 relate to a fourteenth embodiment.
Figure 47:
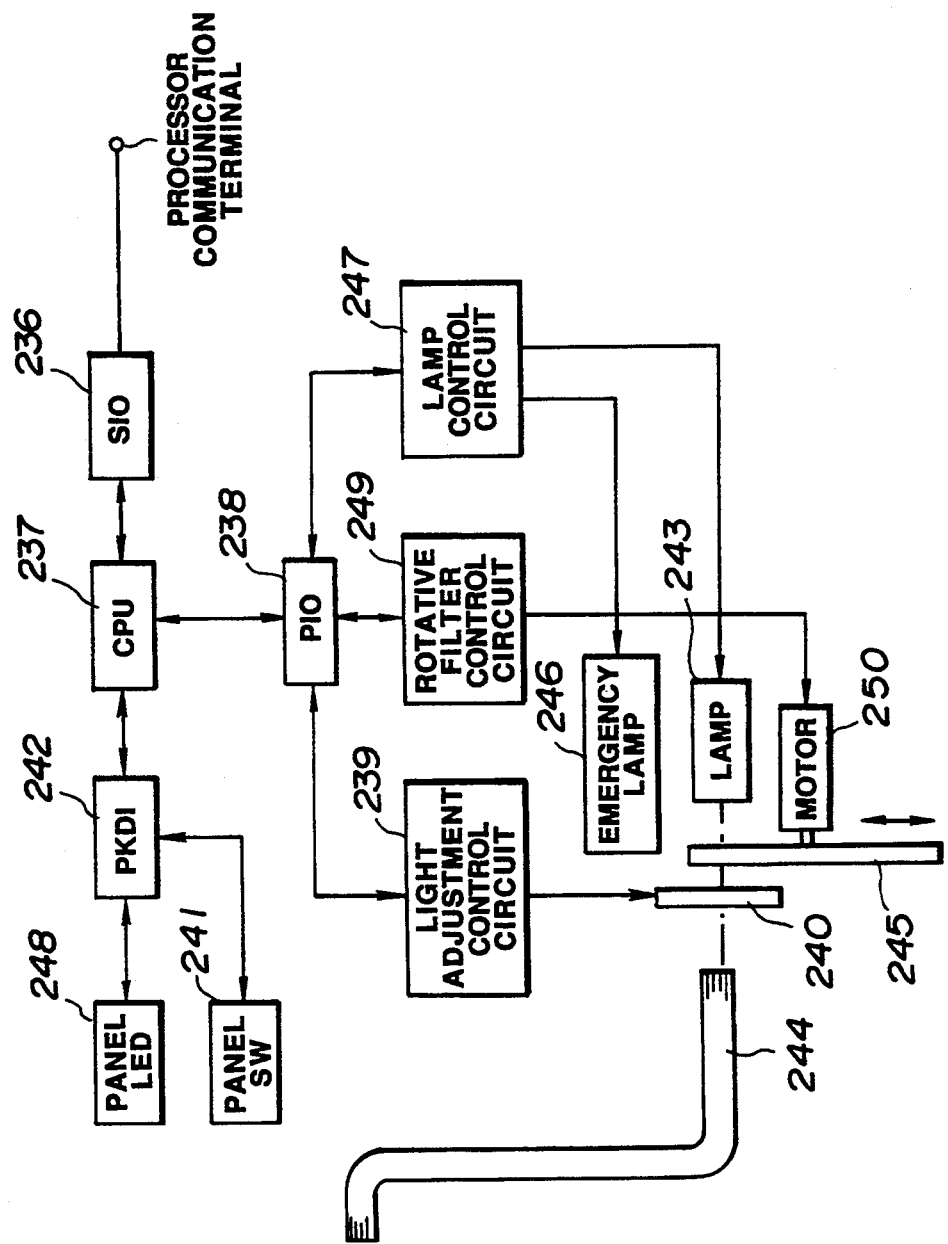
Figure 48:
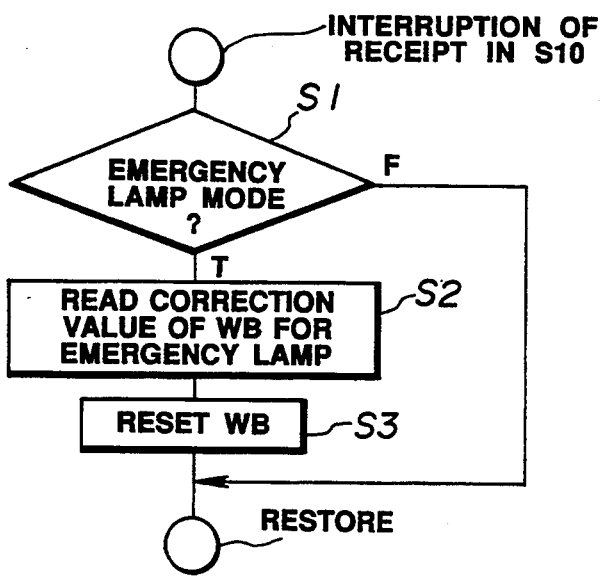

FIGS. 46 to 48 relate to a fourteenth embodiment of the present invention. FIG. 46 is a block diagram which illustrates the structure of a signal processing portion of an electronic endoscope apparatus. FIG. 47 is a structural view which illustrates a light source portion. FIG. 48 is a flow chart relating to a white balance adjustment.

The electronic endoscope apparatus according to this embodiment is an apparatus capable of processing both signal of a single-plate color (a simultaneous) imaging method and a plane sequential imaging method. A light source portion shown in FIG. 47 is connected to a signal processing portion shown in FIG. 46. The electronic endoscope apparatus is structured so that switching to the emergency lamp due to a failure of the light source portion is detected and the operation of the white balance operation to be performed by the signal processing portion is changed.

In the signal processing portion shown in FIG. 46, the circuit which must be operated in different manners between the single-plate color imaging mode and the plane sequential imaging mode is constituted by an FPGA (Field Programmable Gate Array). As a result, circuit information (an FPGA program) loaded down from a CPU 211 is changed at the time of the power supply so that signal processes adaptable to the foregoing two methods can be performed. The FPGA program is supplied through a CSIO 209. The procedure and the like of the process to be performed by the circuit constituted by the FPGA is controlled in accordance with a process control supplied via a parallel I/O controller (PIO) 235. It should be noted that circuits constituted by FPGAs are expressed by double-boarders.

The structure and operation of the electronic endoscope apparatus will now be described.

A CCD 210 serving as the imaging means is disposed in, for example, the endoscope.

The CCD 210 picks up an image under irradiation light emitted from the light source portion and adapted to the imaging method to transmit an imaging signal. The imaging signal transmitted from the CCD 210 is supplied to the signal processing portion to be processed by a processing operation adapted to the imaging method. As a result, for example, R, G and B video signals are transmitted.

First, a signal process for the single-plate color imaging will be described.

Referring to FIG. 46, a drive signal generated by an SSG (synchronous Signal Generator) 212 is converted to have a predetermined voltage by a CCD driver 213 to be transmitted. The CCD 210 has a color mosaic filter (omitted from illustration) on the imaging surface thereof. The CCD 210 is driven by a CCD drive signal transmitted from the CCD driver 213. The SSG 212 generates a drive signal for single-plate color imaging.

A reading signal supplied from the CCD 210 is demodulated by a CDS (Correlate Double Sampling) circuit 214 and converted into a digital signal by an A/D converter 216 via an AGC amplifier 215. The signal immediately after it has been A/D-converted is supplied to a color separation circuit 217 and an AGC wave detection circuit 218. The AGC wave detection circuit 218 generates an AGC control signal to feed back it to the AGC amplifier 215 via a D/A converter 219. In this structure, the AGC is operated so that sufficient brightness can be obtained even if a dark subject is imaged.

The output from the CDS circuit 214 is A/D-converted by an A/D converter 220 in order to adjust the quantity of light emitted from the light source portion before it is received by a light regulation wave detection circuit 221.

The light regulation wave detection circuit 220 calculates the average level and the brightness distribution of the image and transmits the result of the calculations to a CPU 211. The CPU 211 regulates and calculates light and transmits the results to the light source portion via a serial I/O controller (SIO) 222. The video signal which has been AGC-adjusted is separated into brightness (Y) signal and color difference (R-Y and B-Y) signals by the color separation circuit 217. In a color processing circuit 223, color processes peculiar to a variety of endoscope images are performed. Each signal after it has been color-processed is supplied to a white balance wave detection circuit 224 to supply color balance information to the CPU 211.

The CPU 211 calculates a color correction value in accordance with the result of the wave detection at the time of setting the white balance and transmits it to a white balance (WB) control circuit 225. The correction value is used to multiply each color difference signal so that correct color balance is obtained.

The video signal, which has been subjected to the color correction calculation, is γ-corrected by a γ-correction circuit 226. Then, the video signal is stored in three field-memories (FM) 228 by a memory input control circuit 227. Each of video signals read from each memory 228 and denoting the brightness and the color difference is converted into R, G and B signals in a matrix circuit 229. Then, data supplied from the CPU 211 is superimposed on the video signal due to color tone correction performed by a color tone circuit 230 and a superimpose 231. The signal on which required characters are superimposed is D/A-converted by three D/A converters 232 and transmitted to the outside as R, G and B video signals.

The characters to be superimposed are stored in a VRAM 233 and the superimposing timing is controlled by a CRT controller 234.

The signal processing operation to be performed at the time of imaging a subject by the plane sequential method will now be described.

A CCD 210 has no color mosaic filter on the imaging surface in this case. Further, the circuits each of which is constituted by the FPGA are supplied with an FPGA program for plane sequential imaging.

R, G and B plane sequential signals read from the CCD 210 are subjected to CDS and AGC processes similarly to the case where a subject is imaged by the single-plate color imaging method and supplied to the color separation circuit 217. Since the color separation process does not need to be performed at the time of imaging a subject by the plane sequential imaging method, the foregoing circuit 217 simply acts as a bypass, circuit. Then, the signal subjected to the color process and the white balance process is received by a memory input control circuit 227 in which control is performed so that the video signal supplied as R, G and B sequential signals is distributed to three frame memories 228.

Since the matrix operation in the ensuing process does not need to be performed similarly to the color separation, the R, G and B signal made to be simultaneous signals in the memory 228 are also bypassed in the matrix circuit 229 before they are received by the ensuing color tone circuit 230. The following video signal processes are the same as those to be performed when the single-plate color imaging method is employed.

In the light source portion shown in FIG. 47, the light regulation signal transmitted from the signal processing portion is received by a CPU 237 via an SIO 236. The CPU 237 controls a light regulation control circuit 239 via a parallel I/O controller (PIO) 238 in accordance with the light regulation signal to drive the diaphragm blade 240 for adjusting the light regulation light quantity.

An instruction issued by using a panel switch 241 is read by a PKDI (Programmable Key/Display Interface) 242 to perform control of LED display, lamp control and rotative filter control and the like. For example, insertion/removal of the rotative filter 245 to and from the optical path of the irradiation light source and a light guide 244 is changed over in accordance with an instruction made by using the panel switch 241 to select the single-plate color imaging mode or the plane sequential imaging mode. Further, the change of the mode is communicated to the CPU 211 in the signal processing portion via SIOs 236 and 222. It should be noted that reference numeral 248 represents a panel LED. The rotative filter 245 is rotated by a motor 250 controlled by a rotative filter control circuit 249.

The light source portion of the endoscope apparatus is provided with an emergency lamp 246 comprising, for example, a halogen lamp in order to secure a visual field even if a main irradiation lamp 243 (a xenon lamp is usually used) develops a failure during an observation. If the main lamp 243 has been turned off, the CPU 237 in the light source portion detects it to turn on the emergency lamp and notifies this to the CPU 211 in the signal processing portion via the SIOs 236 and 222. The lamp control circuit 247 controls the change over of the lamp.

FIG. 48 is a flow chart of an interruption process to be performed by the CPU in the signal processing portion.

When the SIO 222 receives data from the light source portion, interruption takes place. As a result, a processing task shown in FIG. 48 is commenced. If a discrimination is made in step S1 that the received data is a code corresponding to the change (detection of the emergency lamp) of the light source, the CPU 211 reads out a WB correction value for a halogen lamp stored previously in step S2. The CPU 211 supplies the correction value to the WB balance control circuit 225. In step S3, the WB control circuit 225 multiplies the correction value corresponding to each color difference signal (in the single-plate color imaging mode) or each of R, G and B signals (in the plane sequential imaging mode). As a result, standard color reproduction for the halogen lamp irradiation is obtained.

Since this embodiment has the arrangement that, if the main lamp of the light source portion develops a failure and it is therefore turned off, the main lamp is changed over to the emergency lamp and the white balance corresponding to the lamp is again set, rapid change in the color reproduction, which can be taken place at the time of turning on the emergency lamp, can be prevented. As a result, even if the lamp has been changed over, an observed image exhibiting excellent color reproducibility can be obtained.

Figure 49:
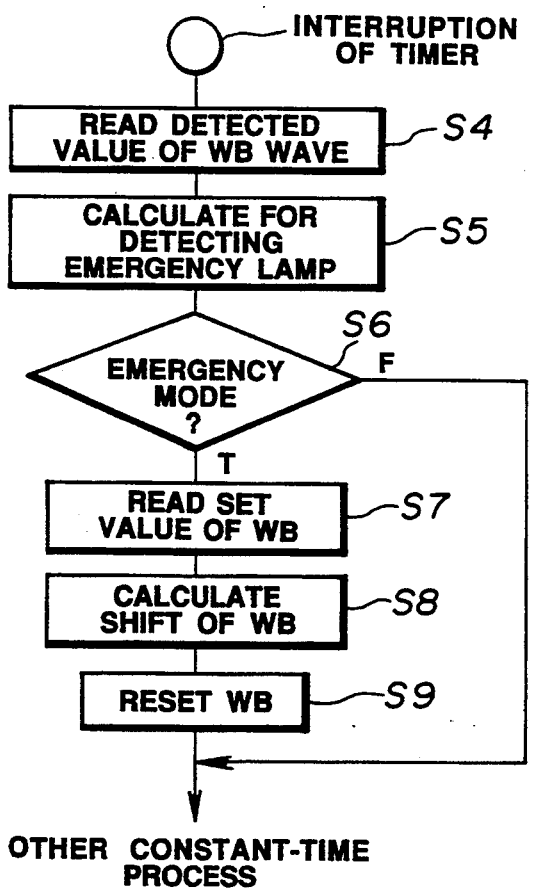
FIG. 49 is a flow chart relating to the white balance adjustment according to a fifteenth embodiment.

FIG. 49 is a flow chart relating to a white balance adjustment to be performed in a fifteenth embodiment of the present invention.

Since the hardware structure of an electronic endoscope apparatus according to this embodiment is the same as that according to the fourteenth embodiment, its description is omitted here.

The flow chart shown in FIG. 49 shows a portion of a timer interruption process to be performed by a CPU in the signal processing portion. The foregoing task illustrates operations to be performed at predetermined cycles of time, for example, an operation for reading a switching instruction made by using the panel or an operation for controlling lighting of the LED. As one of the foregoing processes, a process is performed in which rapid color change of an imaging signal is detected. That is, data is read from the white balance wave detection circuit 224 in steps S4 and S5 to subject the data to a comparison with past color data. In the case where the lamp in the light source portion has been changed from the xenon lamp for the usual irradiation to the halogen lamp for the emergency irradiation in step S6, the image is rapidly changed in a direction in which the color temperature is lowered if the subject is the same. Therefore, the change of the lamp can be detected in accordance with the image signal.

If the change over to the emergency lamp has been detected, the CPU 211 performs the following color correction operation. That is, the present set value of the white balance is read and a correction calculation is performed to correspond to the color temperature change taken place in the lamp in steps S7 and S8. In step S9, the result of the calculation is written on the WB control circuit 225 to again set the white balance.

Since this embodiment has the arrangement that the color information extracted from the image signal is used to detect the change of the lamp in the light source portion and the shift of the white balance is performed, the color correction can automatically be performed when the emergency lamp has been lit on even if a connection is established with a light source portion which does not communicate the emergency lamp detection signal. Since this embodiment has the arrangement that the color correction operation is performed by performing a correction calculation with a color correction value with respect to the present set value, further precise color correction can be performed as compared with the fourteenth embodiment.

Figure 50:
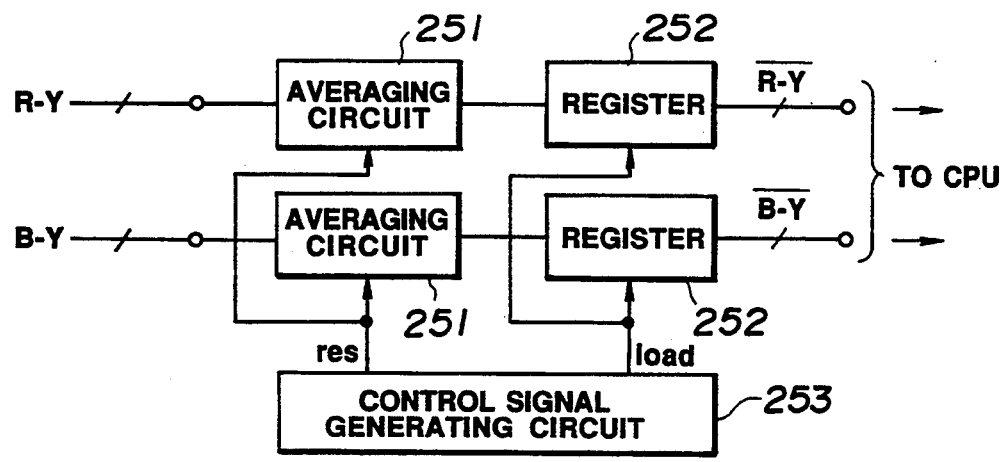
FIGS. 50 to 53 relate to a sixteenth embodiment.
Figure 51:
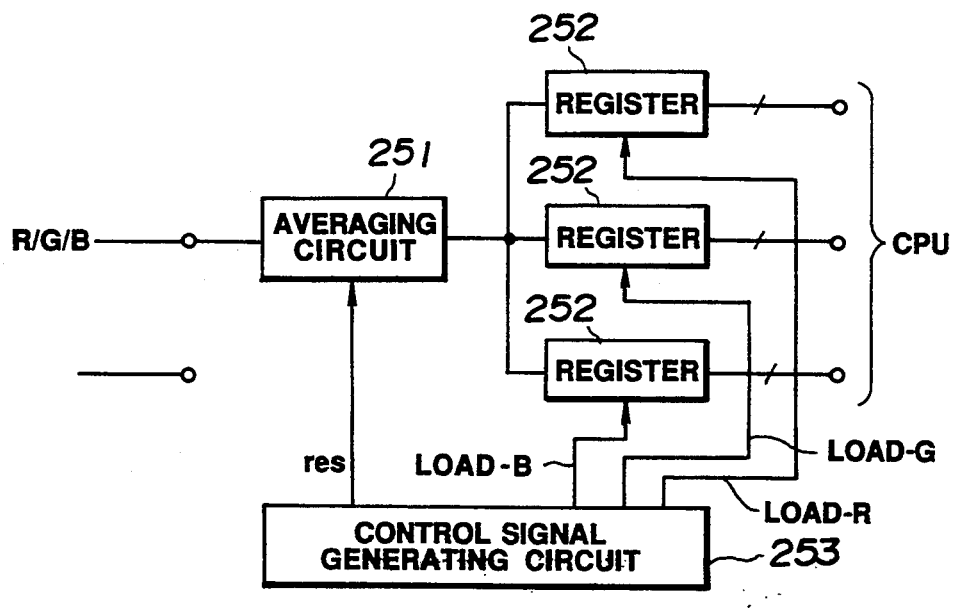
Figure 52:
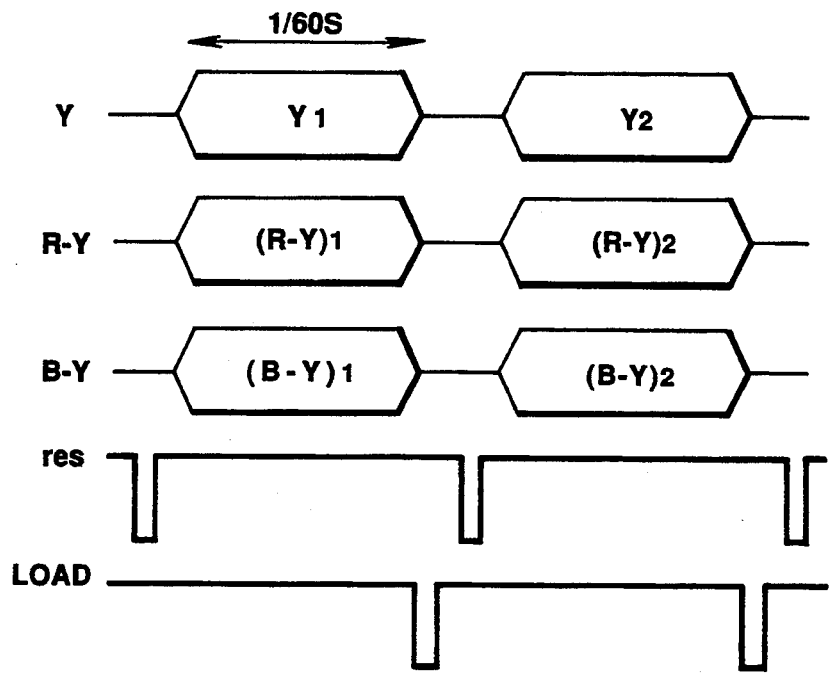
Figure 53:
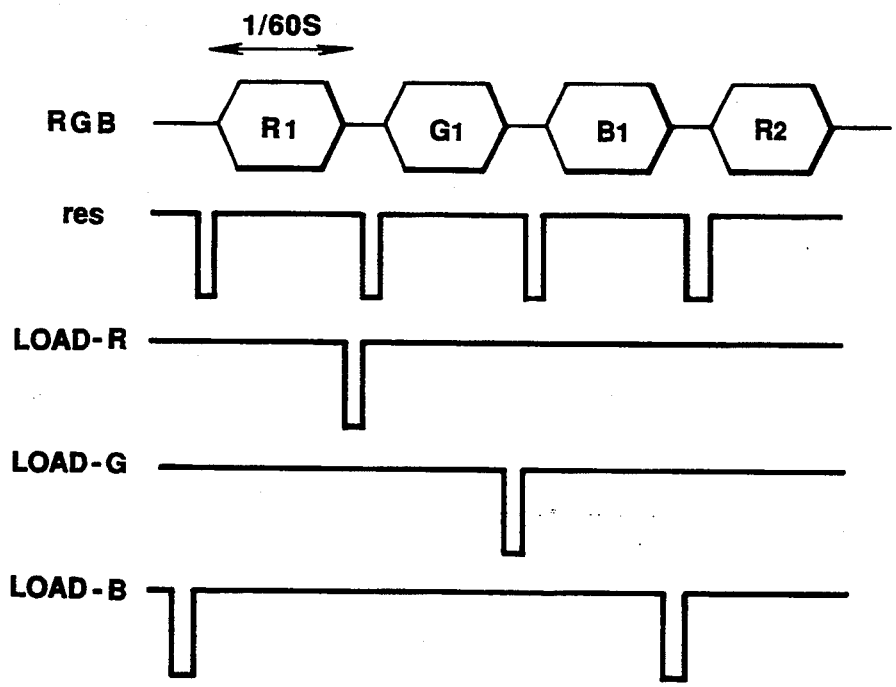

FIGS. 50 to 53 relate to a sixteenth embodiment of the present invention. FIG. 50 is a block diagram which illustrates a white balance wave detection circuit for use at the time of performing the single-plate color imaging. FIG. 51 is a block diagram which illustrates a white balance wave detection circuit for use at the time of performing the plane sequential imaging. FIG. 52 is a timing chart of the circuit shown in FIG. 50. FIG. 53 is a timing chart of the circuit shown in FIG. 51.

Since the hardware structure of the electronic endoscope apparatus according to this embodiment is the same as that according to the fourteenth embodiment, its description is omitted here.

The change over between the wave detection circuit for the single-plate color imaging shown in FIG. 50 and the wave detection circuit for the plane sequential imaging is performed by re-programming the FPGA as described above.

If a single-plate color imaging mode has been instructed by using the panel 241 of the light source portion, the CPU 237 in the light source portion detects this to remove the rotative filter 245 from the optical path. As a result, the irradiation mode is changed over to a white light irradiation. Simultaneously, the CPU 237 communicates that the imaging mode has been changed to the signal processing portion via the SIOs 236 and 222. The CPU 211 in the signal processing portion receives it to re-program the FPGA of each portion. The WB balance wave detection circuit 244 of the foregoing portions is programmed as shown in FIG. 50.

Two input terminals of the white balance wave detection circuit 224 are supplied with color difference signals (R-Y/B-Y). The white balance wave detection circuit 224 is provided with averaging circuits 251 for integrating their color difference signals and registers 252 for storing the average values. The foregoing elements are controlled by a control signal generating circuit 253.

Since the supplied color difference signals have been made simultaneous by the color separation circuit 217, R-Y and B-Y are supplied simultaneously. Therefore, resetting of each averaging circuit 251 and loading (load) into the registers are common to the two color differences. The timing of this process is loaded whenever one image plane has been completed. Further, resetting (res) is performed after loading has been completed.

In the plane sequential imaging mode, the white balance wave detection circuit 224 is, in a time sequential manner, supplied with the R, G and B sequential signals at the input terminal for R-Y in the single-plate color imaging mode. On the other hand, the other terminals are supplied with no signal. Accordingly, the circuit structure is so arranged that one averaging circuit 251 is provided and its output is distributed to the three registers 252. Further, the average values of the R, G and B image planes are stored in the three registers 252 in response to a control signal generated by the control signal generating circuit 253. That is, the averaging circuits 251 are reset at each of R, G and B image planes as shown in FIG. 53. Further loading (load-R, load-G and load-B) is performed after the planes of the colors corresponding to the registers 252 have been completed.

Since this embodiment structured as described above has the arrangement that the white balance circuits are changed over to be adaptable to the type of the irradiation of the light source, the circuits can be automatically set while eliminating a necessity of changing over them manually. Therefore, imaging can be performed by different imaging method.

Figure 54:
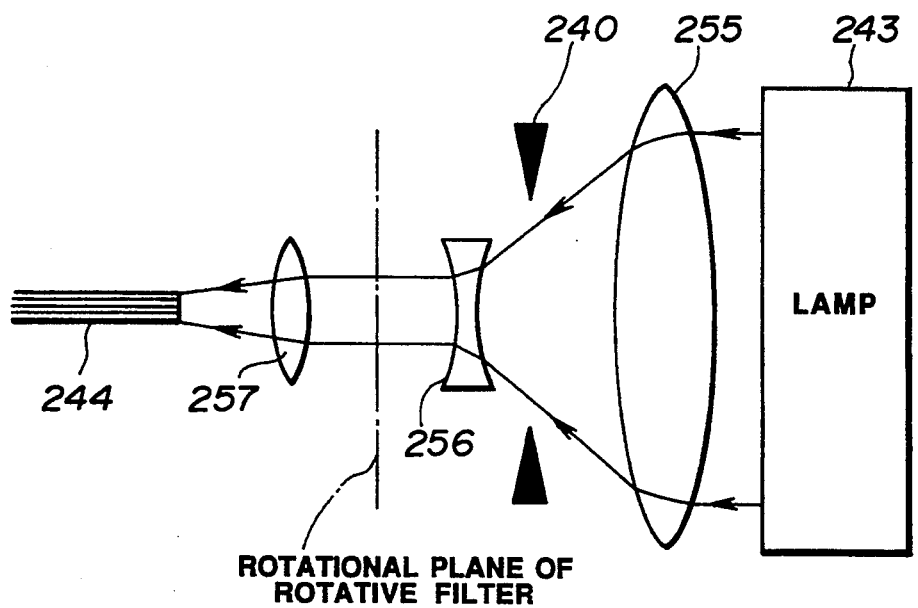
FIGS. 54 to 58 relate to a seventeenth embodiment.
Figure 55:
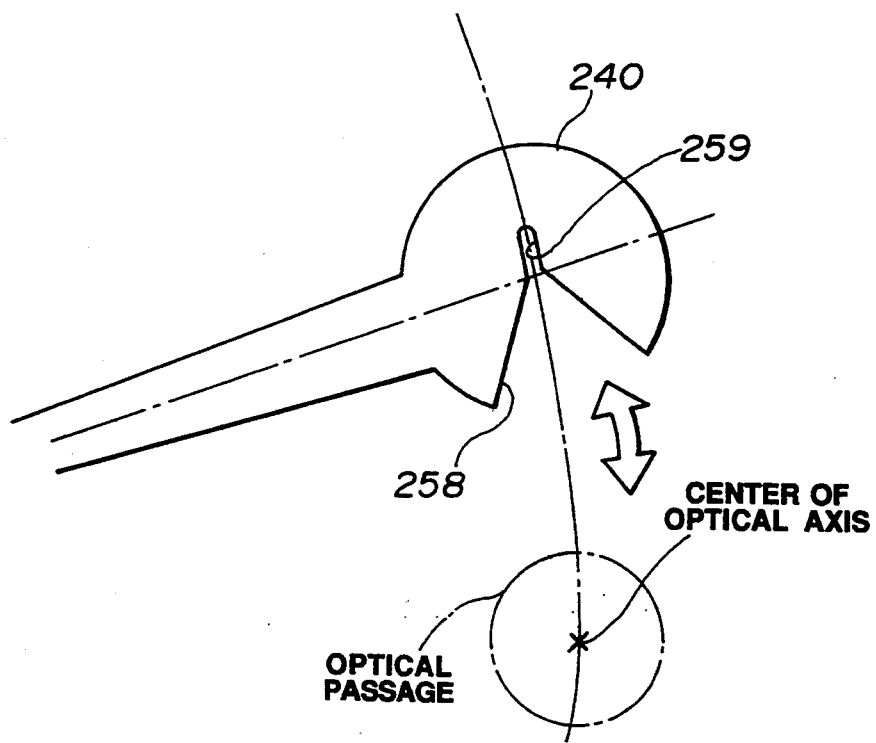
Figure 56:
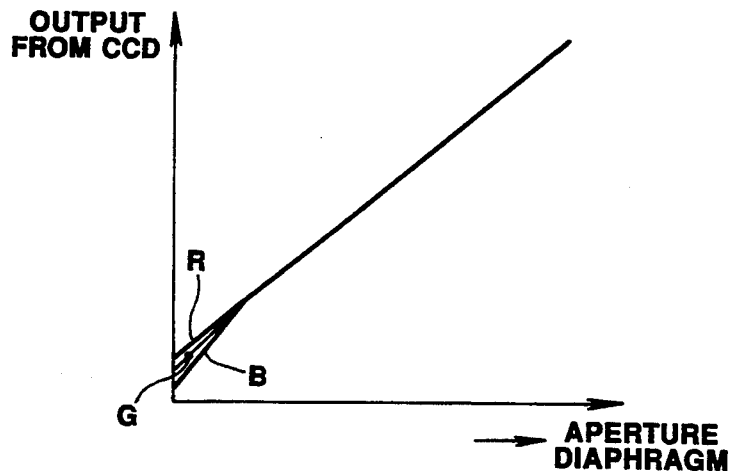
Figure 57:
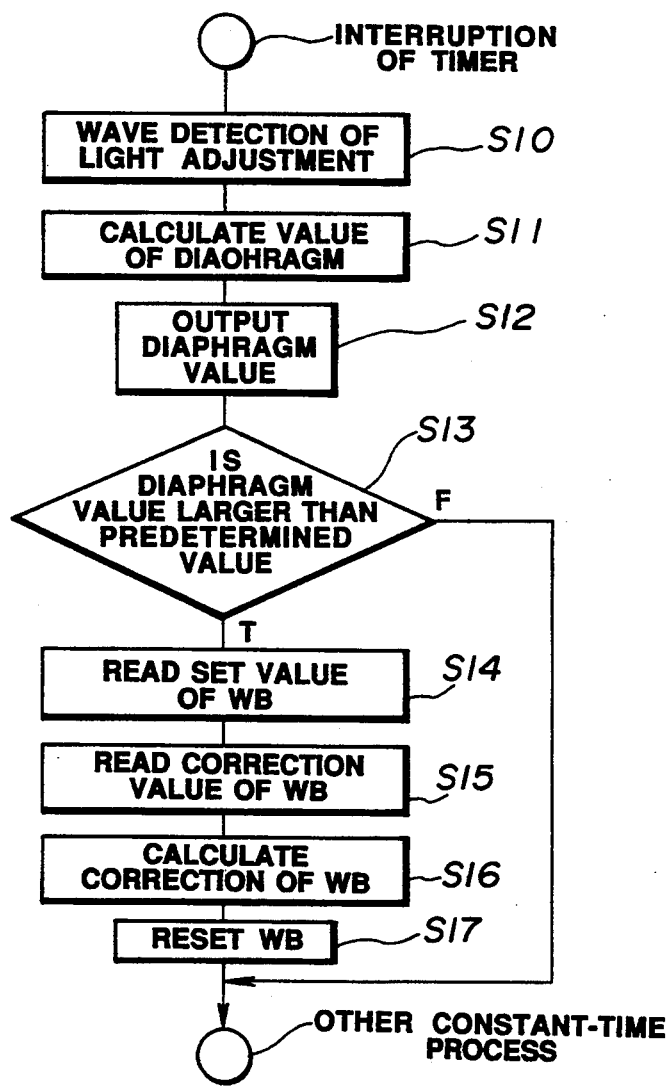
Figure 58:
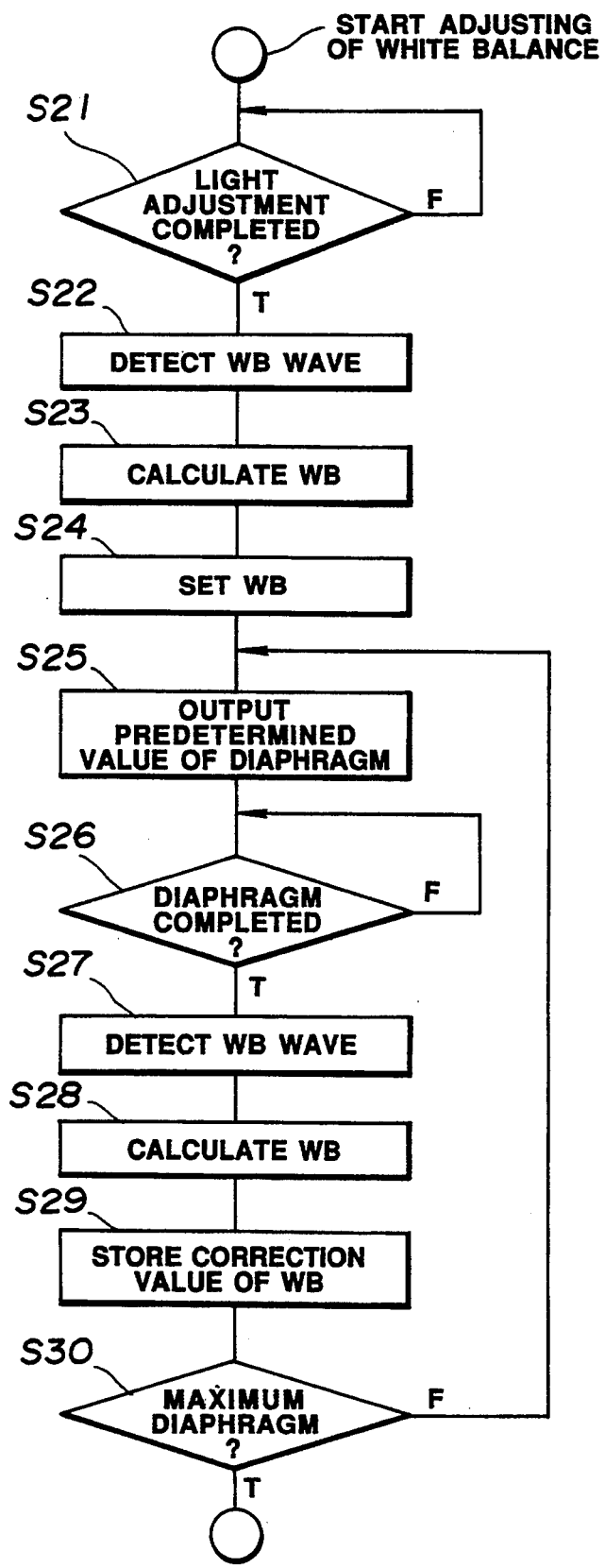

FIGS. 54 to 58 relate to a seventeenth embodiment of the present invention. FIG. 54 is a structural view which illustrates an optical system in the light source portion. FIG. 55 is an explanatory view which illustrates the positional relationship between the shape of a diaphragm blade and the optical axis. FIG. 56 is a correlative view between the diaphragm aperture and each color with respect to the CCD outputs. FIG. 57 is a flow chart of a timer interruption. FIG. 58 is a flow chart for obtaining a correction value of the white balance.

The electronic endoscope apparatus according to this embodiment is structured so that the quantity of diaphragm is detected and the white balance is set to correspond to the detected diaphragm quantity.

Since the hardware structure of the electronic endoscope apparatus according to this embodiment is the same as that according to the fourteenth embodiment, its description is omitted here.

In the optical system in the light source portion shown in FIG. 54, light beams generated in the lamp 243 are converged by a first lens 255. Then, the light quantity is controlled by means of the diaphragm blade 240 and made incident upon a second lens 256. The incidental light is converted into plane sequential irradiation light by the rotative filter 245 in the plane sequential irradiation mode. Then, the plane sequential irradiation light is converged by a third lens 257 and introduced into a light guide 244.

The diaphragm blade 240 shown in FIG. 55 is disposed to traverse the optical axis of irradiation light. As a result, the angle which shields the optical path controls the quantity of transmissive light. The diaphragm blade 240 has a sector shape cut portion 258 and a slit portion 259 for controlling the light quantity. The slit portion 259 enables an effect to be obtained in that the transmissive light quantity is not rapidly changed when the angle of the diaphragm blade 240 is changed during a change from a region in which the diaphragm quantity is small to a region in which the diaphragm quantity is large.

However, it has been known that passing of light beams through the slit portion 259 causes a diffraction effect to take place. Therefore, the color balance of irradiation light is changed, for example, as shown in FIG. 56 in a region in which the diaphragm quantity (the diaphragm aperture) is large. As a result, color can undesirably be changed particularly when a subject is imaged by a conventional endoscope apparatus at a short distance.

FIG. 57 shows a portion of a flow of a timer interruption process to be performed by the CPU in the signal processing portion according to this embodiment. On this task, operations are written for performing a process at predetermined cycles of time, for example, output of a light quantity control signal, reading of a switch state from the panel and control of lighting the LED.

If the timer interruption process has been commenced since a predetermined time has passed, the CPU 211 reads out brightness information from the light regulation wave detection circuit 221, the diaphragm value for obtaining an optimum light quantity is calculated and the result of the calculation is transmitted to the light source portion via the SIOs 222 and 236 in steps S10, S11 and S12. If a discrimination has been made in step S13 that the diaphragm value, which is the result of the calculation, is larger than a predetermined range of values, the CPU 211 simultaneously resets the white balance in steps ensuing step S14. That is, the present set value of the white balance and a color correction value previously stored in the CPU are read out in steps S14 and S15. Then, the CPU 211 performs a calculation to correct the value to the present set value by using the color correction value in step S16 and resets the white balance in step S17.

FIG. 58 is a flow chart for obtaining a correction value of the white balance with respect to the diaphragm quantity.

When the white balance operation has been instructed by using a key switch of the panel 241, the foregoing task is commenced. After the light regulation operation has been completed and proper brightness has been set in step S21, color information is read from the white balance wave detection circuit 224 in step S22. Thus, a color correction value for realizing correct color reproduction is calculated and transmitted in step S23. In next step S24, the white balance is set.

Then, the diaphragm value is sequentially changed to the maximum value (the minimum light quantity) and the correction value of the white balance is obtained by transmitting a predetermined value to the light regulation control circuit 239 in step S25 so that the diaphragm is enlarged. After the diaphragm operation has been completed in step S26, color information is received in steps S27, S28 and S29 to calculate and store the white balance correction value for each diaphragm value. The foregoing operations are repeated until the diaphragm becomes maximum in step S30.

Since this embodiment structured as described above has the arrangement that the white balance is reset in accordance with the detected diaphragm value, the color temperature change occurring due to the change in the quantity of the diaphragm can be corrected to observe the image in proper colors.

Although this embodiment is structured so that the diaphragm value is calculated in the signal processing portion, another structure may be employed in which the calculation is performed in the light source portion and the determined diaphragm quantity is communicated to the signal processing portion. In this case, a similar effect can be obtained.

Figure 59:
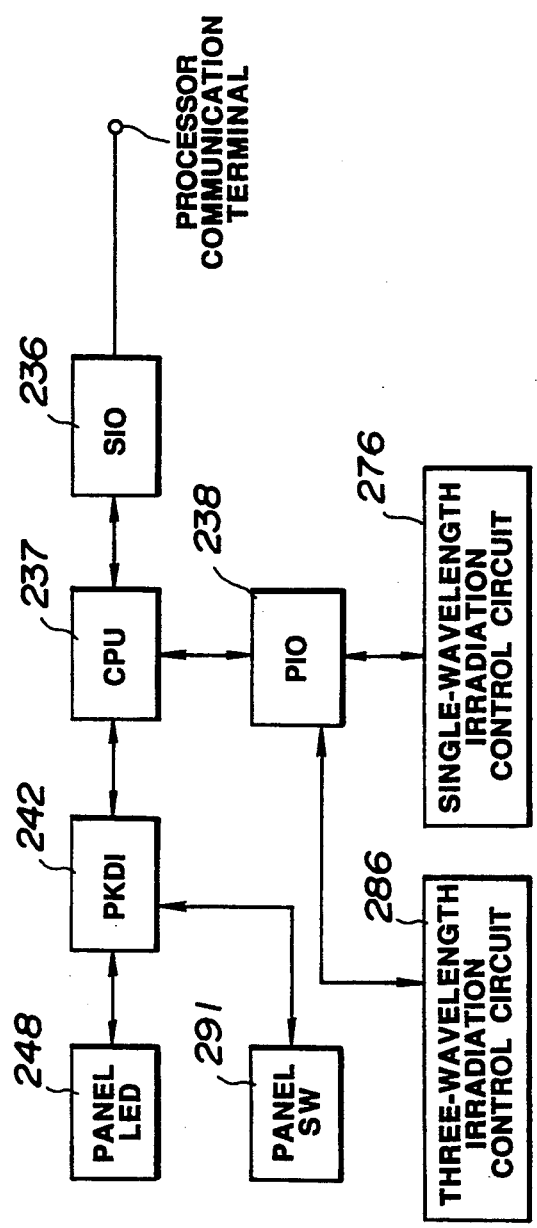
FIGS. 59 to 63 relate to an eighteenth embodiment.
Figure 60:
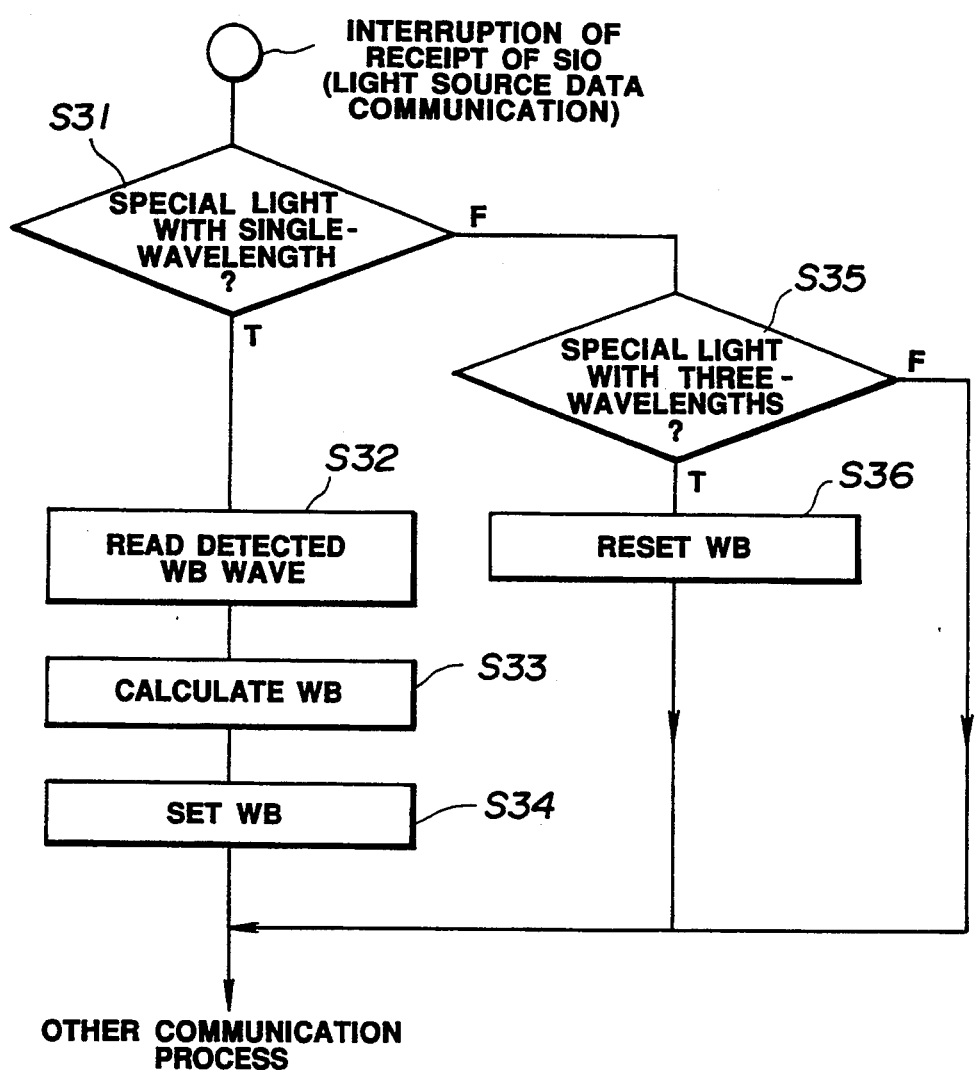
Figure 61:
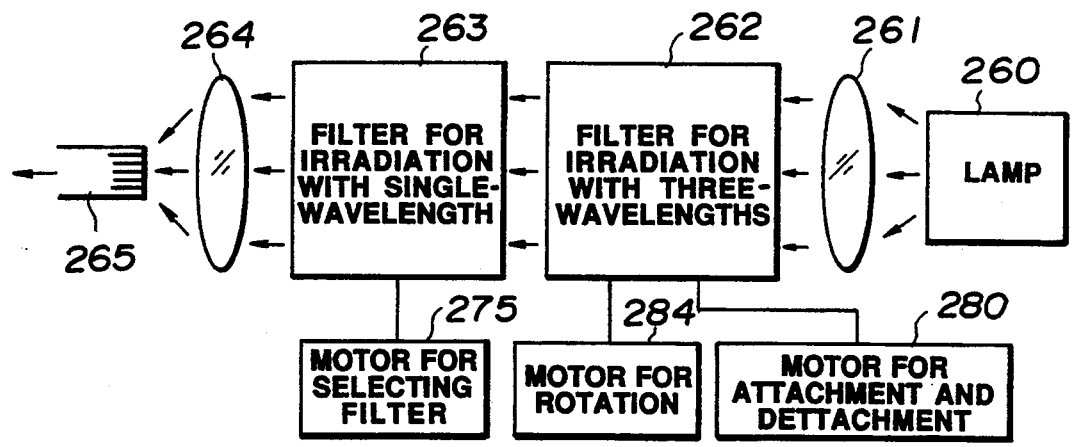
Figure 62:
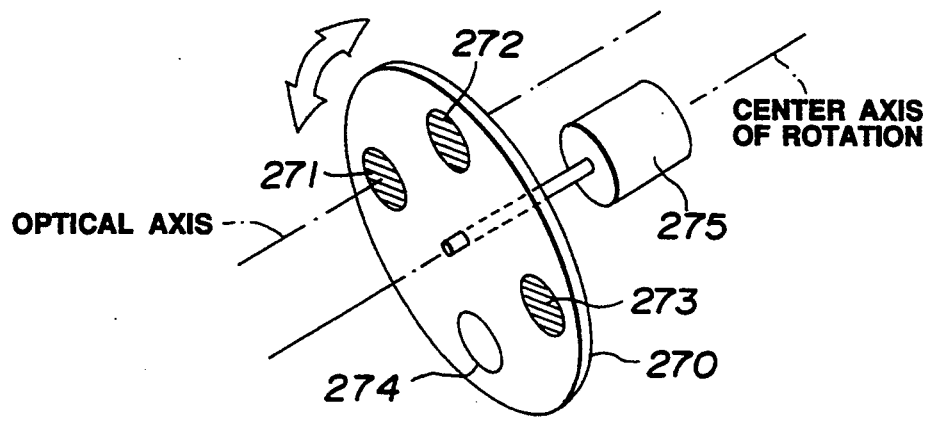
Figure 63:
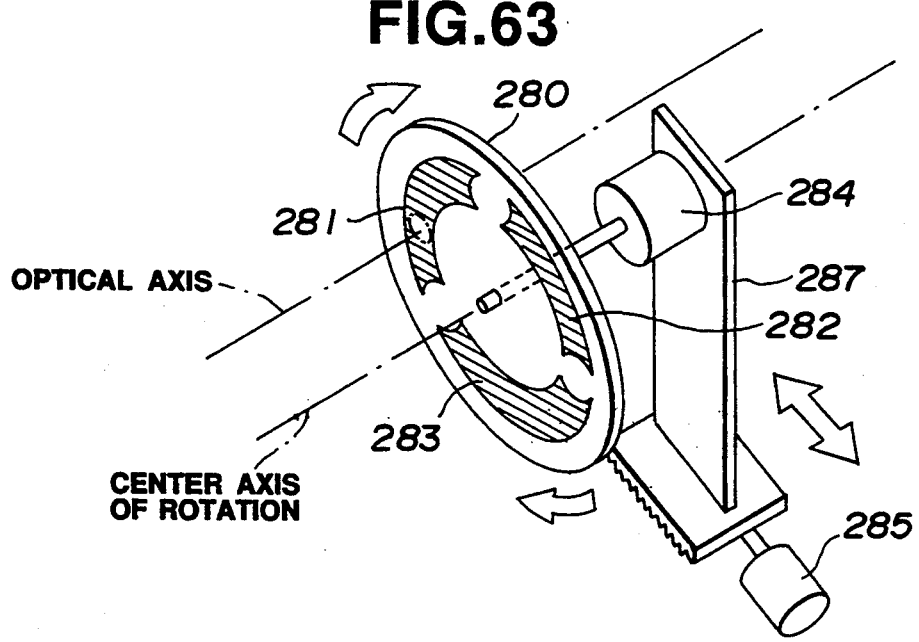

FIGS. 59 to 63 relate to an eighteenth embodiment of the present invention. FIG. 59 is a block diagram which illustrates a light source portion. FIG. 60 is a flow chart for setting the white balance in a special light mode. FIG. 61 is a block diagram which illustrates the structure of the optical system of the light source portion. FIG. 62 is a perspective view which illustrates the structure of single wavelength irradiation. FIG. 63 is a perspective view which illustrates the structure of three wavelength irradiation.

An electronic endoscope apparatus according to this embodiment has an arrangement that special light irradiation, for example, infrared rays, can be performed in addition to usual white light irradiation. The electronic endoscope apparatus is structured so that a special light observation mode in which the irradiation using light except for white light is performed is detected and the white balance is set to a predetermined value when the irradiation using light except for white light is performed.

Since the structure of the hardware of the electronic endoscope apparatus according to this embodiment is the same as that according to the fourteenth embodiment, the descriptions about the same elements as those shown in FIG. 46 are omitted here. Only the different elements will now be described.

In the electronic endoscope field, observation using special light such as infrared rays is sometimes performed in order to observe the blood flow or the like. The special light irradiation method employs single wavelength light or light having a plurality of wavelengths.

In the case where the single wavelength irradiation is performed, the image is usually observed on the monitor as it is. Therefore, a filter exclusively adapted to special light can be fastened to the light source portion. By inserting the filter into the optical path, the single wavelength irradiation is performed.

In the case where the plural wavelength observation is performed (in this case an image of each wavelength is usually quantitatively compared by using an image processing apparatus), a rotative filter having filters for corresponding wavelength is inserted in place of the RGB rotative filter adapted to the plane sequential irradiation to perform the irradiation. The insertion/removal of the special light filter can be instructed by using a panel switch 291 shown in FIG. 59 under control of the CPU 237 in the light source portion, the CPU 237 transmitting control information to the signal processing portion.

FIG. 61 illustrates the structure of an irradiation optical system in the light source portion of the electronic endoscope apparatus. Light beams emitted from a lamp 260 are, via a first lens 261, a rotative filter 262 for the three-wavelength irradiation, a single-wavelength irradiation filter 263 and a second lens 264, made incident upon a light guide 265 connected to the irradiation optical system in the endoscope insertion portion.

A single-wave irradiation filter 263, as shown in FIG. 62, comprises a disc-like member (a turret) 270 to which a plurality of optical filters 271 to 273 are fastened. The plurality of the optical filters 271 to 273 respectively have individual transmissive wavelength regions. Further, the disc-like member (the turret) 270 has a filter non-installation portion 274 for use in the case where the single-wavelength irradiation is not performed.

The turret 270 can be rotated by a motor 275. By rotating the turret 270 until it reaches a position at which a desired optical filter is inserted into the optical path, an arbitrary optical filter can be selected. The rotation of the filter selection motor 275 is controlled by a single-wavelength irradiation control circuit 276 in accordance with an instruction issued from the CPU 237 shown in FIG. 59.

As shown in FIG. 63, a turret 280 for the three-wavelength irradiation filter 262 can be rotated by a motor 284 in synchronization with an image signal. When the special light observation is performed, the turret 280 for the special light and having a plurality of optical filters 281 to 283 having individual transmissive wavelength regions is used to obtain sequential irradiation light of arbitrary three wavelengths.

In the case where the usual observation is performed, change over to a turret, to which red, green and blue optical filters are fastened, is conducted to obtain sequential irradiation light of arbitrary three wavelengths.

The rotative filter system can be moved by an attaching/detaching motor 285. Therefore, the rotative filter 262 can be removed from the optical path to stop the three-wavelength irradiation light.

As shown in FIG. 63, the rotating motor 284, to which the foregoing turret is secured to the rotational shaft thereof, is disposed on a support column of a movable member 287. The base portion of the movable member 287 is moved to be inserted/removed to and from the optical path when the attaching/detaching motor 285 is rotated. The rotating motor 284 and the attaching/detaching motor 285 are controlled by a three-wavelength irradiation control circuit 286 in accordance with instruction issued from the CPU 238 shown in FIG. 59.

Assuming that single-wavelength irradiation light corresponding to a certain optical filter is selected by using a panel switch 291, the CPU 237 rotates the single-wavelength irradiation turret 263 to select the instructed optical filter and to remove the three-wavelength irradiation turret from the optical path. As a result, irradiation using the single wavelength can be performed.

If the three-wavelength irradiation is selected, the CPU 237 rotates the single-wavelength irradiation turret 263 to the filter non-installation portion 274 and inserts the three-wavelength irradiation filter 280 into the optical path to perform the thee-wavelength sequential irradiation.

FIG. 60 is a flow chart for a SIO receipt interruption process to be performed by the CPU in the signal processing portion according to this embodiment.

When data from the light source portion is received, an interruption from the SIO 222 takes place so that the process shown in FIG. 60 is performed. In a case where the data corresponds to the shift of the mode to the special light observation mode, the following process is performed: if a discrimination has been made in step S31 that the special light observation mode is the single-wavelength observation, the white balance adjustment process is performed in steps S32 to S34 to set the levels of the RGB video outputs to the same level. That is, a monochrome image is realized in the case of the single-wavelength observation.

If a discrimination is made in steps S31 and S35 that the special light observation mode is the plural wavelength observation mode, the white balance is reset in step S36 to outwardly transmit images each of which has the same degree of amplification.

In this embodiment structured as described above, the white balance circuit is reset to make the output image to be monochrome-displayed when the single wavelength special light observation is performed. As a result, an image which can easily be recognized can be displayed. Further, this embodiment has the arrangement that the obtained three-wavelength image is transmitted while keeping their level ratio when the special light observation is performed with a plurality of wavelengths. Therefore, a diagnosis or an evaluation can easily be performed with the image processing apparatus.

Although this embodiment has the arrangement that the white balance control is performed to form a monochrome image when the single wavelength observation is performed, it can easily be understood that setting to another color tone except for the monochrome tone can easily be performed.

Figure 64:
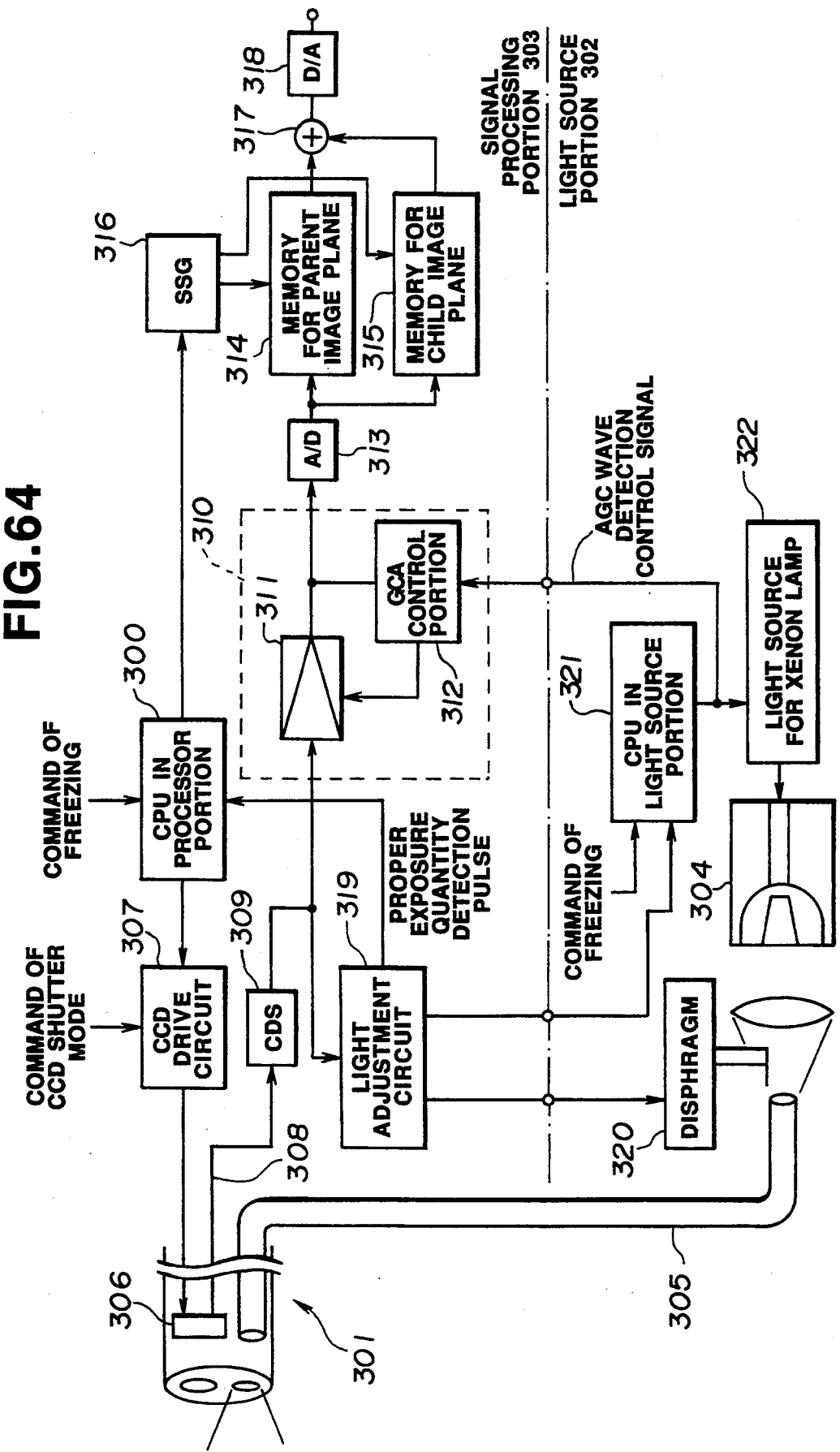
FIGS. 64 to 69 relate to a nineteenth embodiment.
Figure 65:
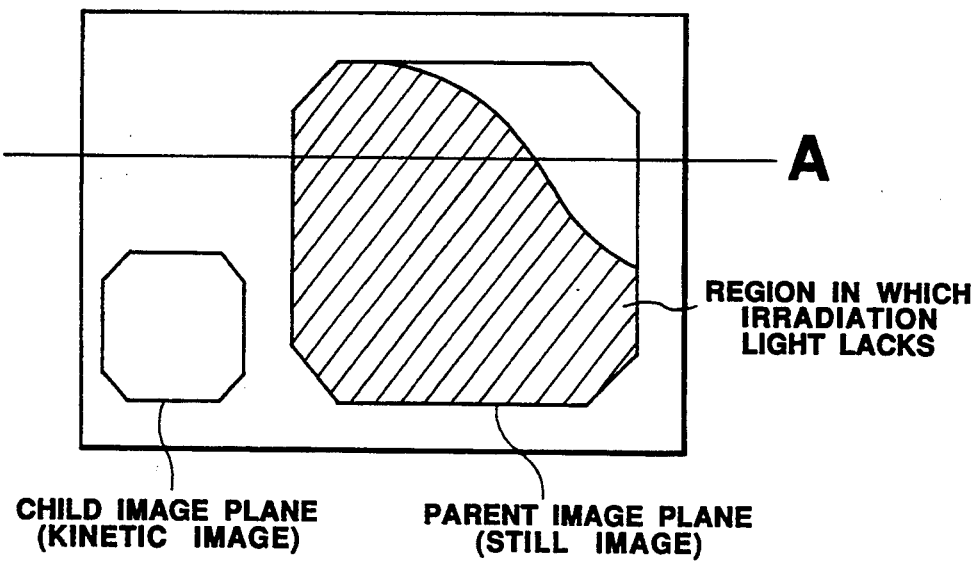
Figure 66:
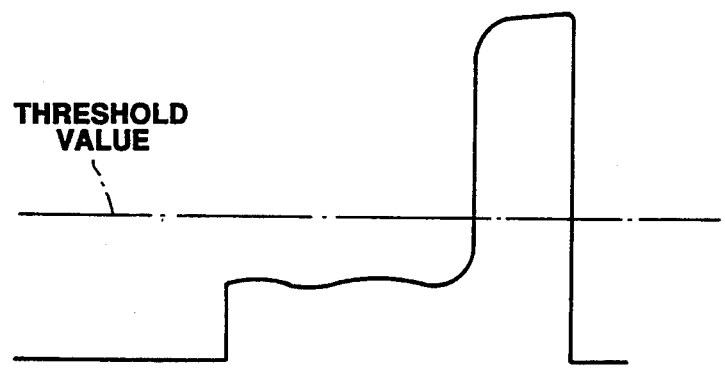
Figure 67:
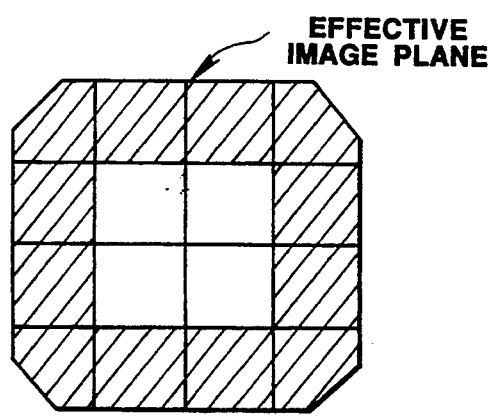
Figure 68:
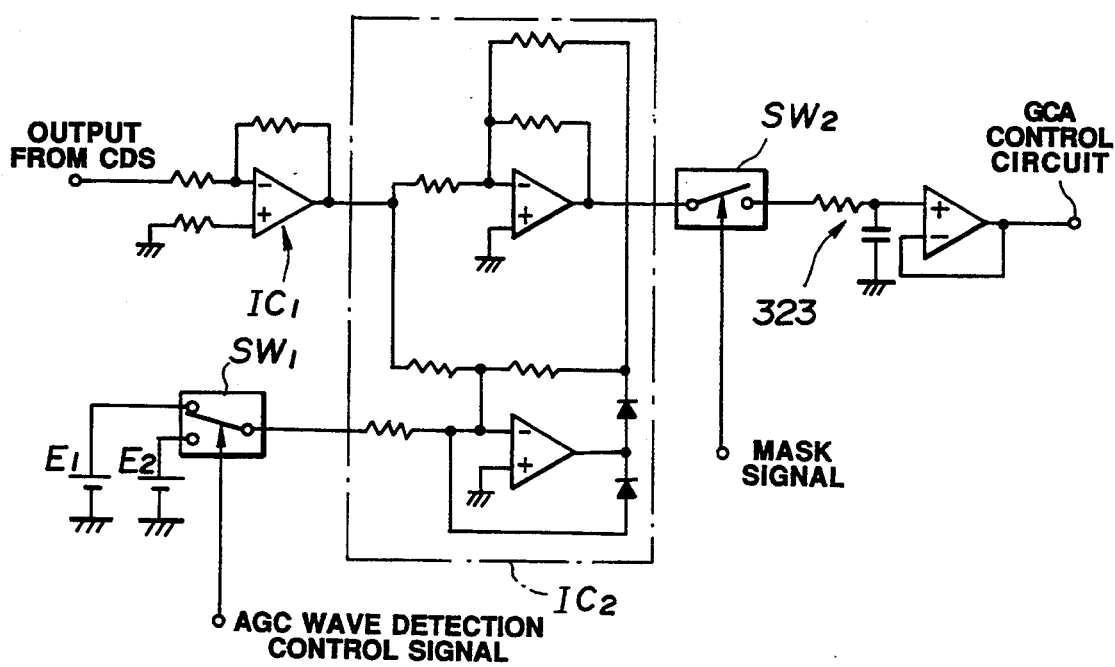
Figure 69:
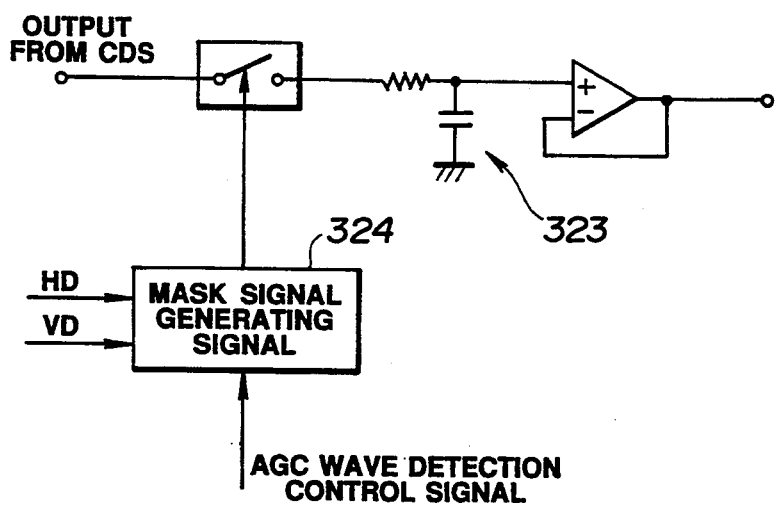

FIGS. 64 to 69 relate to a nineteenth embodiment of the present invention. FIG. 64 is a schematic structural view which illustrates an electronic endoscope. FIG. 65 is a structural view which illustrate a monitor image plane. FIG. 66 illustrates the waveform of a video signal for scanning line A of the image plane shown in FIG. 65. FIG. 67 illustrates AGC wave detection. FIG. 68 is a circuit diagram which illustrates an example of a GCA control portion. FIG. 69 is a circuit diagram which illustrates another structure of the GCA control portion.

An electronic endoscope apparatus according to this embodiment comprises an endoscope 301, a light source portion 302, a signal processing portion 303 and a monitor portion (omitted from illustration). The foregoing endoscope apparatus is structured so that the irradiation mode realized by the light source portion 302 is changed over between a continuous irradiation mode and a flash irradiation mode. Further, a threshold value for use in the wave detection performed by the AGC of the signal processing portion 303 is set or the wave detection range is changed when the flash irradiation is performed.

Light emitted from a xenon lamp 304 of the light source portion 302 is applied to a subject from the front surface of the endoscope 301 through a light guide 305. Light reflected from the subject is made incident upon a CCD 306 disposed similarly on the front surface of the endoscope 301. The CCD 306 is driven in response to a drive signal generated by a CCD drive circuit 307 disposed in the signal processing portion 303 so that incidental light is photoelectrically converted into an electric signal. The electric signal is received by an AGC circuit 310 via a signal line 308 passing through the endoscope 301 and via a CDS circuit 309 in the signal processing portion 303. The level of an output signal from the CDS circuit 309 is AGC-controlled by the AGC circuit 310 to be a predetermined level before it is supplied to an A/D converter 314.

The AGC circuit 310 comprises a gain control amplifier 311 for amplifying the output from the CDS circuit 309 and a GCA control portion 312 for controlling the gain of the gain control amplifier 311 by detecting the wave of the output from the gain control amplifier 311.

The output from the gain control amplifier 311 is stored in a parent image plane memory 314 and a child image plane memory 315 via an A/D converter 313. Writing/reading to and from the parent image plane memory 314 and the child image plane memory 315 is controlled by a SSG 316.

In a usual mode, a kinetic image, the contents of which is chronologically updated, is transmitted from the parent image plane memory 314 to be displayed on the foregoing monitor.

In the freezing mode, update of the contents in the parent image plane memory 314 is inhibited so that a still image is transmitted. On the other hand, the child image plane memory 315 transmits a kinetic image, the contents of which is chronologically updated. After the still image and the kinetic image have been synthesized with each other, the synthesized image is D/A-converted to be displayed on the monitor.

The CCD drive circuit 307 drives the CCD 306 in a shutter mode under control of the CPU 300 in the processor portion which has received a command of freezing. The SSG 316 reads the parent image plane memory 314 in the freeze mode under control of the CPU 300 in the processor portion which has received the command of freezing.

Image data read from the memories 314 and 315 is superimposed by an adder 317 before it is supplied to an output apparatus, such as the monitor, via a D/A converter 318 and so forth.

The electric signal transmitted from the CCD 306 is wave-detected by a light regulation circuit 319 similarly disposed in the signal processing portion 303 so that a light regulation signal is generated. The light regulation circuit 319 adjusts the diaphragm quantity of a diaphragm 320 in the light source portion 302 in response to the light regulation signal. As a result, control is so performed that the quantity of light to irradiate the subject is made to be a proper quantity. The light regulation circuit 319 transmits wave detection pulses to the CPU 300 in the processor portion when the light regulation circuit 319 detects the proper exposure quantity.

The CPU 321 in the light source portion 302 controls the irradiation mode of the xenon lamp 304 via a xenon lamp power source 322. This embodiment has a continuous mode for continuously emitting irradiation light and a flash mode for intermittently emitting intense irradiation light. When the CPU 321 in the light source portion 302 instructs the flash mode, it simultaneously transmits an AGC wave detection control signal to the GCA control portion 312 in the signal processing portion 303.

The freezing operation to be performed in the shutter mode (device shutter) of the CCD 306 will now be described. When the freezing command is supplied due to the operation of an observer, the CCD drive circuit 307 generates a drive signal to cause the CCD 306 to perform the shuttering operation. Since the foregoing freezing command is supplied to the CPU 321 of the light source portion 302, the CPU 321 instructs the xenon lamp power source 322 to change over the irradiation mode to perform the flash irradiation. When the xenon lam 304 performs the flash irradiation, the light quantity is increased to compensate the lack of the light quantity at the time of the shuttering operation performed by the CCD 306. When a proper exposure quantity is realized, the control performed by the CPU 300 in the processor portion freezes the image of the parent image plane. At this time, a still image formed when the proper exposure quantity is obtained is displayed on the parent image plane on the monitor, while the kinetic image is displayed on the child image plane.

Since irradiation light is maintained for a predetermined time after freezing has been performed in the flash irradiation, the CCD 306 returned to its usual operation after freezing has been performed is temporarily brought to an excessive exposure state with respect to the foregoing irradiation light. Since the AGC circuit 310 reacts to it in the foregoing state, an image having unsatisfactory image quality such as hunting is displayed on the child image plane.

Accordingly, this embodiment has an arrangement that an AGC wave detection control signal transmitted together with the flashing command issued from the CPU 321 in the light source portion causes the GCA control portion 312 to change over the method of wave-detecting the AGC. FIG. 65 illustrate an image displayed on the foregoing monitor. In order to easily make the description, an assumption is made that the upper right portion of the parent image plane is sufficiently irradiated with light and hatching sections except for the upper right portion are not irradiated with light sufficiently.

If the flash irradiation is performed in order to obtain a proper exposure quantity in the freezing operation in the CCD shutter mode, the video signal for the portion designated by scanning line A shown in FIG. 65 becomes as shown in FIG. 66. As shown in FIG. 66, the video signal for the upper right portion of the parent image is temporarily saturated due to the flash irradiation. The GCA control portion 312 sets predetermined threshold value for the video signal and changes over the control method to control the gain of the GCA 311 by using only signals smaller than the threshold value.

The change over of the AGC control method may be performed as follows.

The process is changed so that the GCA control portion 312 divides the effective image plane into plural sections as shown in FIG. 67 and only video signals of regions (hatching sections shown in FIG. 67) surrounding an image plane among the plurality of the divided regions, in which small video signal saturation takes place, are used to control the gain.

If, for example, the wall of the stomach is being observed, the central portion of the image plane is undesirably saturated with respect to the peripheral portion of the image plane. Therefore, it is effective to change the AGC operation by using only the video signals of the regions in the peripheral portion of the image plane in which the saturation tendency is restricted.

FIG. 68 illustrates a specific example of the circuit for use in the GCA control portion 312. The CDS output passes through a reversal amplifier IC1 before it is received by a limiter circuit IC2. In the limiter circuit IC2, voltages E1 and E2 selected by a switch SW1, which has received the foregoing AGC wave detection control signal, limit the CDS output, and signals, the upper limit of each of which is the limited CDS output, are transmitted. Only a desired signal among the foregoing limiter signals for one image plane is, by the switch SW2 to be opened/closed in response to the mask signal, caused to be converted into the control voltage for the GCA by a LPF/holding circuit 323. The LPF/holding circuit 323 comprises a resistor, a capacitor and a buffer.

FIG. 69 illustrates another structural example of the GCA control portion 312. The GCA control portion 312 is arranged so that the received CDS output is not limited but the mask signal is generated by the mask signal generating circuit 324 in response to the AGC wave detection control signal to change the wave detection range. The timing of the generation of the mask signal is made in synchronization with vertical synchronizing signal VD and horizontal synchronizing signal HD.

This embodiment has the arrangement that the flash irradiation for obtaining a proper exposure quantity is performed at the time of the freezing operation in the CCD shutter mode. Therefore, even if a portion of the image is saturated, setting of a threshold value for the AGC wave detection and the control of the subject range of the wave detection cause the AGC to react to the video signal which has been temporarily saturated due to the flash irradiation. As a result, hunting of the kinetic image is prevented.

Figure 70:
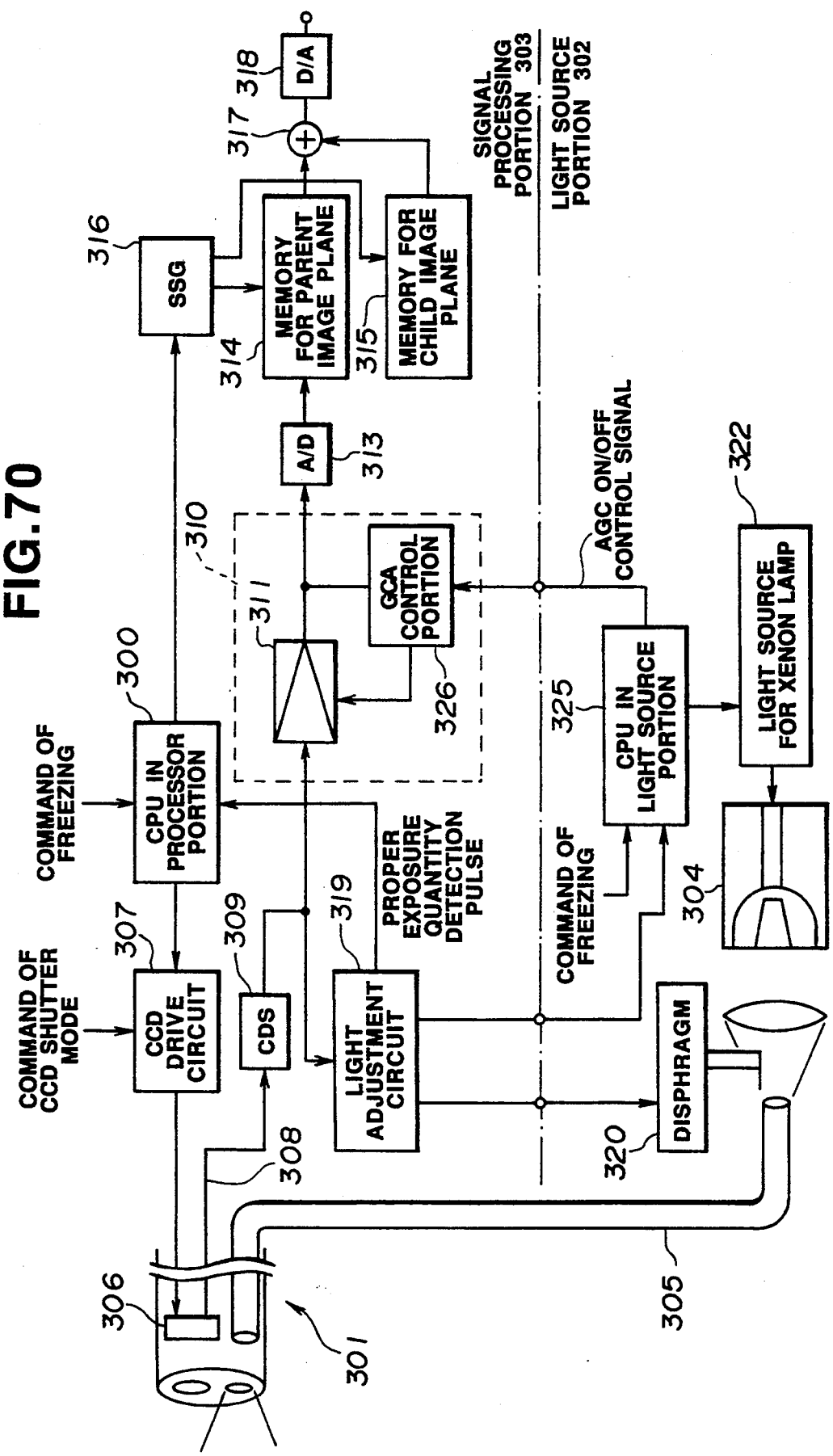
FIGS. 70 and 71 relate to a twentieth embodiment of the invention.
Figure 71A:
Figure 71B:
Figure 71C:
Figure 71D:
Figure 71E:
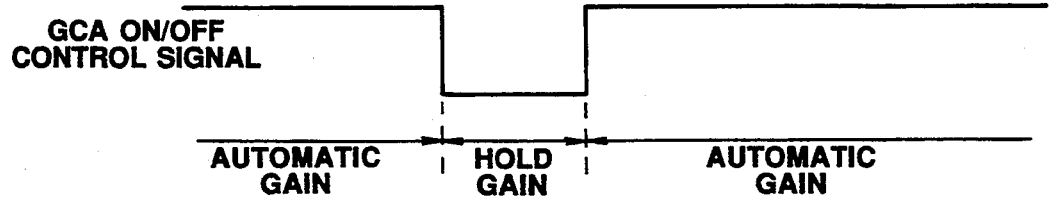

FIGS. 70 and 71 relate to a twentieth embodiment of the present invention. FIG. 70 is a schematic structural view which illustrates an electronic endoscope. FIG. 71 is a timing chart which illustrates the operation of the apparatus shown in FIG. 70.

The electronic endoscope apparatus according to this embodiment is structured so that the irradiation method of the light source portion is changed over between the continuous irradiation and the flash light irradiation. Further, the operation of the AGC is inhibited when the flash light irradiation is performed to maintain a predetermined gain. The same structures and operations as those of the nineteenth embodiment are given the same reference numerals and their descriptions are omitted here.

The apparatus according to this embodiment has an arrangement that the signal processing portion 302 according to the nineteenth embodiment is structured in such a manner that its GCA control portion 312 is replaced by a GCA control portion 326 for controlling operation/stopping of the AGC in response to an AGC on/off control signal transmitted from a CPU 325 in the light source portion.

The freezing operation to be performed in the CCD (the device shutter) mode will now be described with reference to FIG. 71.

An assumption is made that the CCD shutter mode command shown in FIG. 71 (a) has been selected. When a freezing command shown in FIG. 71 (b) is received in the foregoing state due to the operation performed by an observer, the CCD drive circuit 307 causes the CCD 306 to perform the shuttering operation. At this time, the CPU 325 in the light source portion instructs the xenon lamp power source 322 to change over the irradiation mode shown in FIG. 71 (c) to perform the flash irradiation. The flash irradiation performed by the xenon lamp 304 increases the light quantity to compensate the lack of the light quantity at the time of the shuttering operation of the CCD. The light regulation circuit 319 detects a proper exposure quantity and transmits a proper exposure quantity detection pulse shown in FIG. 71 (d) to the CPU 30 in the processor when the proper exposure quantity has been realized. The CPU 30 in the processor receives the foregoing detection pulse to control reading of the parent image memory 314 via the SSG 316 to freeze the image of the parent image plane. As a result, an image when the proper exposure quantity is obtained is displayed as a still image on the parent image plane of the monitor.

Since the child image plane displays the kinetic image, the display of an image having an unsatisfactory image quality such as hunting is prevented by the following operation change according to this embodiment.

The AGC off signal shown in FIG. 71 (e) is, together with the flash irradiation command, supplied to the GCA control portion 326. In accordance with change over information to the flash irradiation mode, the GCA control portion 326 stops the operation of the AGC and holds the gain control voltage for the GCA 311 until the flash irradiation is completed.

In this embodiment, even if the flash irradiation is performed in the freezing operation in the CCD shutter mode in order to obtain a proper exposure quantity, the AGC control is stopped to hold the gain. As a result, this embodiment is able to prevent the display of an image having an unsatisfactory image quality such as hunting on the monitor. Therefore, a proper observed image can be obtained.

Figure 72:
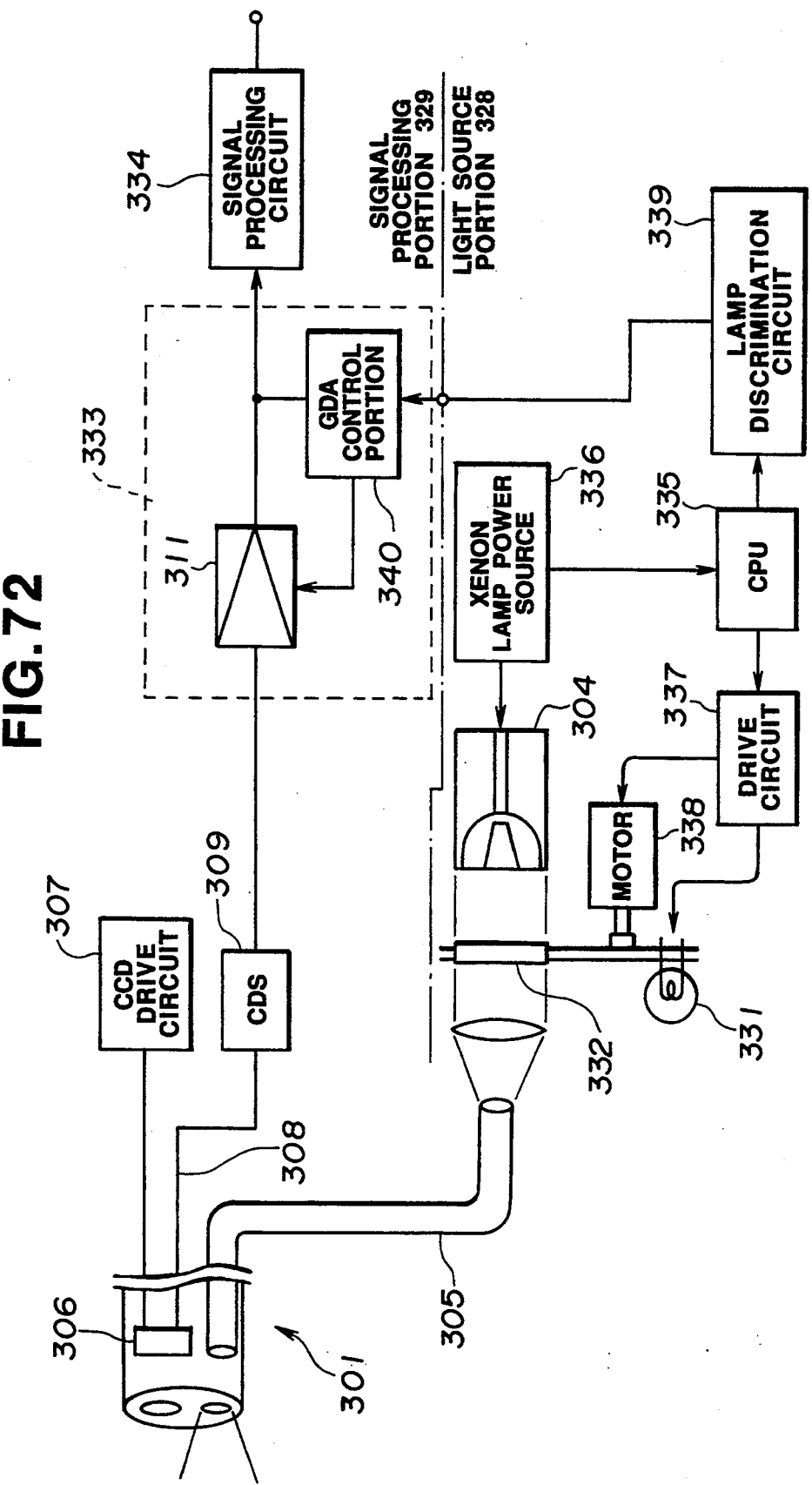
FIG. 72 is a schematic structural view which illustrates an electronic endoscope apparatus according to a twenty-first embodiment.

FIG. 72 is a schematic structural view which illustrates an electronic endoscope apparatus according to a twenty-first embodiment of the present invention.

The electronic endoscope apparatus according to this embodiment comprises a light source portion 328 having the xenon lamp 304 serving as a usual lamp and an emergency lamp 331. The light source portion 328 is structured so that change over to the emergency lamp 331 is performed to conduct the irradiation if the xenon lamp 304 is burned out. The same structures and operations as those of the nineteenth embodiment are given the same reference numerals and their descriptions are omitted here. The description will be made about only the difference portions.

Light emitted from the xenon lamp 304 in the light source portion 328 passes through a filter 332 for reducing the light quantity before light is made incident upon the light guide 305. Irradiation light, which has passed through the light guide 305 in the endoscope 301, is applied to a subject through the front surface of the endoscope 301. Light reflected from the subject is made incident upon the CCD 306 similarly disposed on the front surface of the endoscope 301. The CCD 306 is driven in response to a drive signal generated by the CCD drive circuit 307 in the signal processing portion 329 to photoelectrically convert incidental light into an electric signal. The gain of the electric signal is automatically controlled by a GCA 333 in the signal processing portion 329 via the cable 308 in the endoscope 301 before it is transmitted to an output apparatus, such as the foregoing monitor, via a signal processing circuit 334.

The GCA 333 comprises the gain control amplifier 311 and a GCA control portion 340 for changing the gain in response to a signal denoting the result of discrimination of the change over of the lamp and supplied from the light source portion 339.

A CPU 335 in the light source portion 328 supervises the values of electric currents passing through a xenon lamp power source 336 which supplies electric power to the xenon lamp 304. If the CPU 335 has detected a rapid reduction in the value of the electric current and discriminated that the xenon lamp 304 has been disconnected, the CPU 335 causes a drive circuit 337 to control a motor 338. As a result, the emergency lamp 331 is moved onto the optical axis to turn on the emergency lamp 331.

Generally, the emergency lamp of the electronic endoscope apparatus is able to emit light by a quantity smaller than that of the diagnosing xenon lamp. Therefore, if the emergency lamp is turned on due to the disconnection of the xenon lamp, the monitor image is undesirably darkened as compared with the case where the xenon lamp is used.

Accordingly, this embodiment has an arrangement that a lamp discrimination circuit 339 disposed in the light source discriminates whether the diagnosing xenon lamp or the emergency lamp is being turned on. The lamp discrimination circuit 339 discriminates as described above in accordance with the result of the supervision of the electric current performed by the CPU 335 and with the instruction to perform the change over.

If a discrimination is made that the emergency lamp is being turned on, control is performed so that the GCA gain control portion 340 of the GCA circuit 333 makes the maximum gain of the AGC to be larger than a value set to be adaptable to the case where the diagnosing xenon lamp is turned on.

According to this embodiment, even if the diagnosing xenon lamp is disconnected during an observation performed with the endoscope and therefore the change over to the emergency lamp is performed, a proper visual field can be kept by setting the maximum gain to be a small value to correspond to the reduction in the irradiation light quantity. Further, a sufficiently-bright observed image can be obtained.

While considering that the case where the emergency lamp is being turned on is an emergency state, the range in which the gain can be varied may be changed to sufficiently keep the visual field although the S/N ratio is sacrificed. In this case, a similar effect can be obtained.

Figure 73:
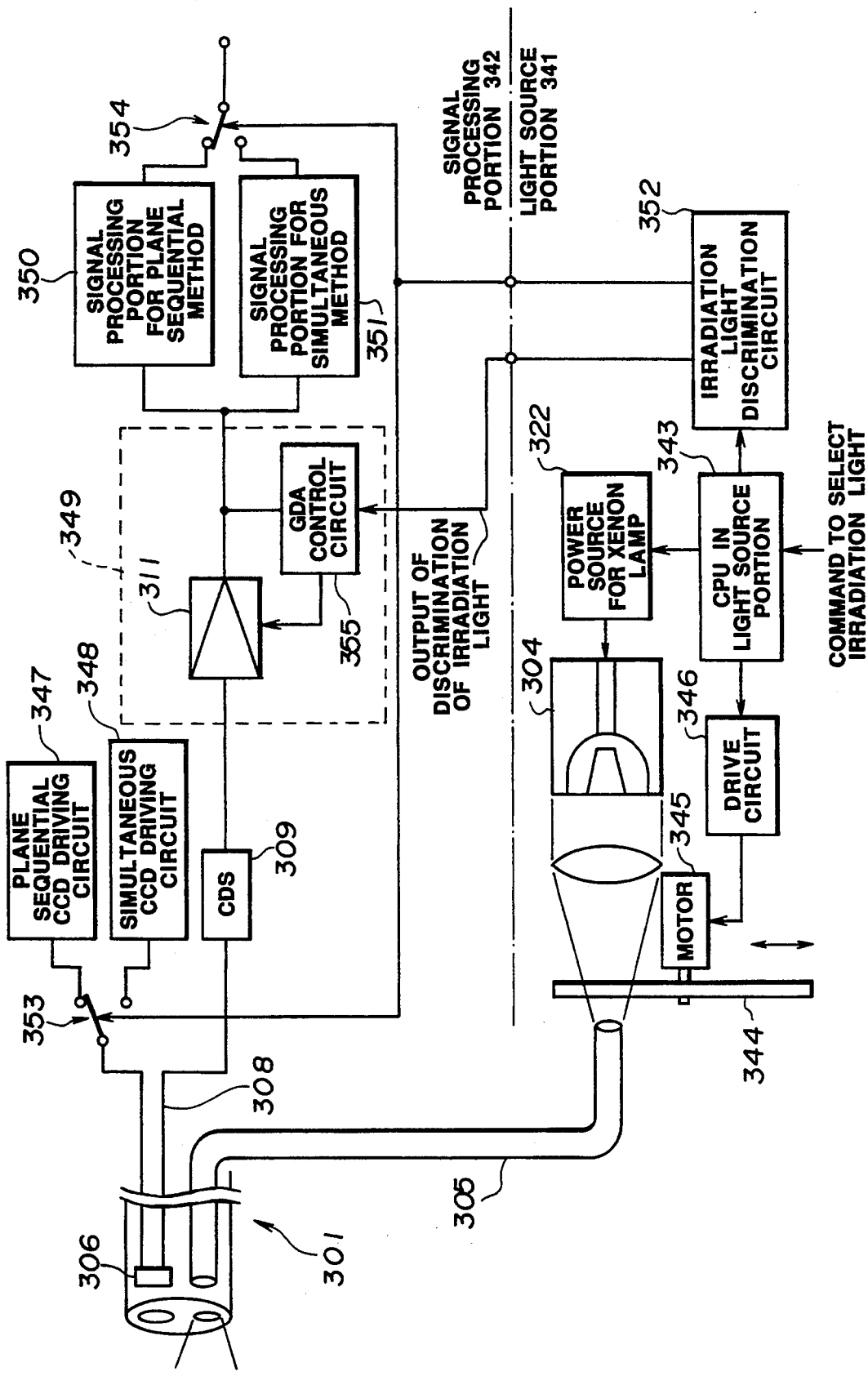
FIGS. 73 and 74 relate to a twenty-second embodiment.
Figure 74:
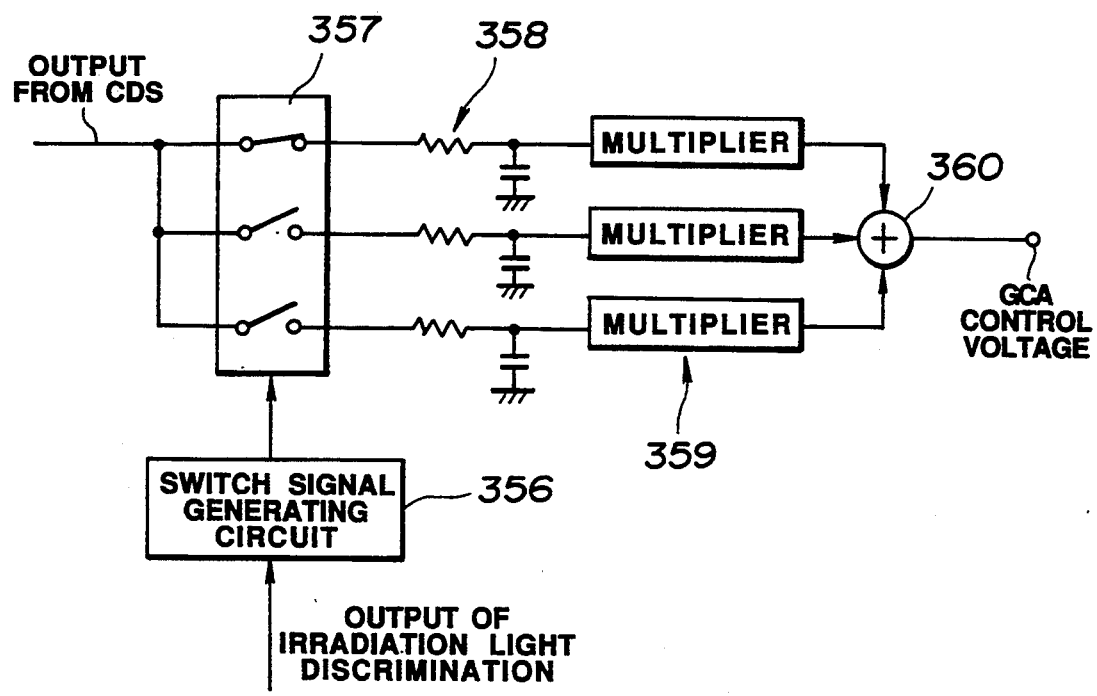

FIGS. 73 and 74 relate to a twenty-second embodiment of the present invention. FIG. 73 is a schematic structural view which illustrate an electronic endoscope apparatus. FIG. 74 is a block diagram which illustrates a structural example of the GCA control portion.

The electronic endoscope apparatus according to this embodiment is structured so that a light source portion 341 is able to perform irradiation light while changing over irradiation light between plane sequential imaging irradiation light and simultaneous imaging irradiation light. A signal processing portion 342 drives the CCD 306 while performing the change over between the plane sequential imaging method and the simultaneous imaging method and changes over its signal process to be adaptable to the foregoing method. The electronic endoscope apparatus discriminates the irradiation mode of the light source, whether the plane sequential imaging irradiation mode or the simultaneous imaging mode. In accordance with the discriminated imaging method, the wave detection method of the AGC is changed. The same structures and operations as those of the nineteenth embodiment are given the same reference numerals and their descriptions are omitted here. The description will be made about different portions.

A change over means provided for a front panel (omitted from illustration) is used to supply whether plane sequential imaging irradiation light or simultaneous imaging irradiation light is selected to a CPU 343 in the light source portion 341. The CPU 343 in the light source portion 341 moves a RGB filter 344 onto the optical axis of irradiation light emitted from the xenon lamp 304 if the plane sequential imaging irradiation light is selected. Then, the CPU 343 controls a drive circuit 346 to rotate a filter 344 by a motor 345.

If simultaneous imaging irradiation light is selected, the CPU 343 controls the drive circuit 346 to move the RGB filter 344 away from the optical axis to stop the rotation of the motor 345.

Irradiation light is made incident upon the light guide 305 to be applied to a subject through the front surface of the endoscope. Light reflected from the subject is photoelectrically converted into an electric signal by the CCD 306 disposed at the leading portion of the endoscope.

The signal processing portion 342 includes a plane sequential CCD drive circuit 347 for driving the CCD 306 to perform the plane sequential imaging operation and a simultaneous CCD drive circuit 348 for driving the CCD 306 to perform the simultaneous imaging operation.

The signal processing portion 342 further includes a plane sequential signal processing portion 350 and a simultaneous signal processing portion 351 in the rear of the GCA circuit 349. The two systems composed of the CCD drive circuits 347, 348, the signal processing circuits 350 and 351 are selected by using switches 353 and 354 in accordance with-irradiation light, which is being emitted and which has been discriminated by an irradiation light discrimination circuit 352 disposed in the light source portion 341.

The electric signal read from the CCD 306 is received by a GCA 349 via the cable 308 in the endoscope and via the CDS 309. An output from the CDS 309 is auto-gain-controlled by a GCA 349 to have a predetermined level, and then it is transmitted to an output apparatus, such as the monitor, via the signal processing portion adapted to each imaging method.

The GCA circuit 349 comprises the gain control amplifier 311 and a GCA control portion 355 for controlling the gain of the amplifier 311.

The operation of the GCA control portion for controlling the AGC operation will now be described.

An assumption is made here that, if plane sequential imaging irradiation light to be emitted from the light source portion 341 is selected, the output from the CCD 306 is performed so that R, G, B and R, ..., are sequentially supplied at field cycles. In accordance with a value obtained by integrating the G video signal components among the CDS outputs, the control voltage of the GCA 311 is determined.

As an alternative to using the G signal component, B signal component or R signal component may be used. In place of using single-type signal components, plural types of signal components may be integrated and combined, for example, the G components and the R components may be combined. Another method may be employed in which the R, G and B signals transmitted sequentially are integrated and added while multiplying with multipliers to obtain brightness component Y, and the integrated value of the brightness component Y is calculated to be used to determine the control value of the GCA.

When simultaneous imaging irradiation light is selected, the CDS outputs are integrated to determine the control voltage of the GCA. As an alternative to this, the brightness component Y contained in the signal may be extracted to be used.

FIG. 74 is a block diagram which illustrates a structural example of the GCA control portion 355.

If irradiation light is plane sequential imaging light, the signals transmitted as the outputs from the CDS in the sequential order as R, G and B, ..., are changed over by switches 357 operated by a switching signal generating circuit 356 to be distributed to three LPF/holding circuits 358. The signals held by the three LPF/holding circuits 358 are multiplied with coefficients by three multipliers 359 and then added by an adder 360. As a result, the integrated value of the brightness signal Y can be obtained, the integrated value being made the control voltage of the GCA.

The switching signal generating circuit 356 controls opening/closing of the switches 357 in accordance with a irradiation light discrimination output from the irradiation light discrimination circuit 352.

If only the G component is intended to be used, it can be performed by changing the switching operations performed by the switches 357.

If irradiation light is simultaneous imaging light, the control voltage of the GCA can be taken by always switching on one of the switches 357.

Since the embodiment has the arrangement that the wave detection method of the AGC in the processor portion is automatically optimized to be adaptable to the irradiation mode of the light source, an electronic endoscope freed from a complicated setting process and therefore exhibiting excellent operational facility can be provided.

Figure 75:
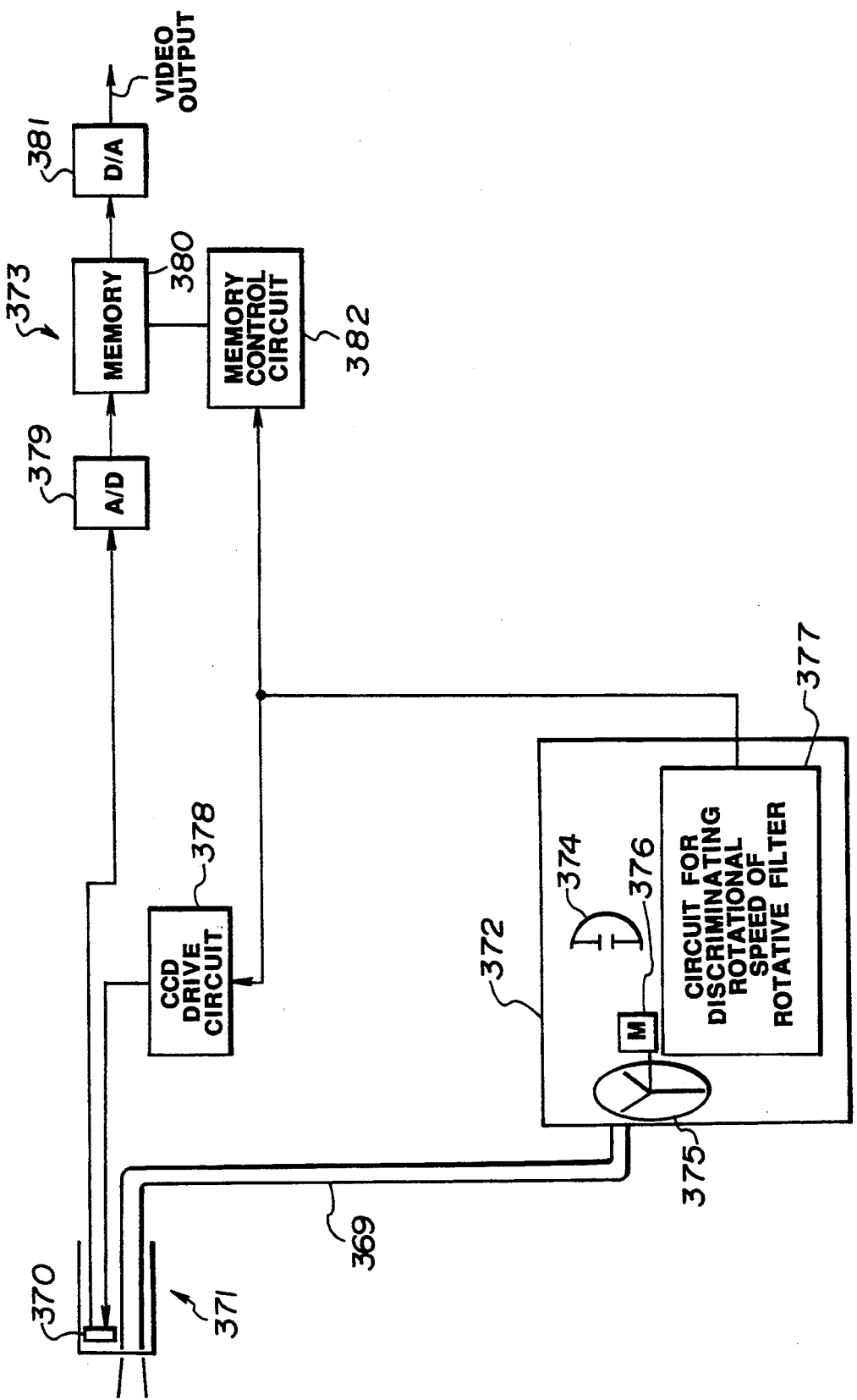

FIGS. 75 to 78 relate to a twenty-third embodiment of the present invention. FIG. 75 is a schematic structural view which illustrates an electronic endoscope apparatus. FIG. 76 is a structural view which illustrates the filter configuration of a rotative filter. FIG. 77 is a structural view relating to a process for detecting the speed of the rotative filter. FIG. 78 is an explanatory view relating to reading of a CCD and control of a memory.

The electronic endoscope apparatus according to this embodiment shown in FIG. 75 comprises a light guide 369, an electronic endoscope 371 having a CCD 370, a light source portion 327 for irradiating a subject with plane sequential irradiation light via the light guide 369 and a signal processing portion 373 for driving the CCD 370 and processing an obtained image signal to transmit a video signal.

The light source portion 372 comprises a lamp 374, a rotative filter 375 for separating light emitted by the lamp 374 into time sequential color irradiation light beams, a motor 376 for rotating the rotative filter 375 and a circuit 377 for discriminating the rotational speed of the rotative filter 375.

The CCD 370 is driven by a CCD drive circuit 378 of the signal processing portion 373 to convert the image of the subject into an image signal. The output from the CCD 370 is A/D-converted by an A/D converter 379 in the signal processing portion 373, and then it is made simultaneous and D/A-converted by a D/A converter 381 to be made a video signal to be transmitted.

A discrimination signal transmitted from the circuit 377 for discriminating the rotational speed of the rotative filter 375 is supplied to a memory control circuit 382 for controlling writing/reading to and from the memory 380 and to the CCD drive circuit 378.

Light separated into each light through the rotative filter 375 is applied to a subject through the light guide 369. Reflected light from the subject is imaged by the CCD 370.

FIGS. 76a to 76c illustrate structural examples of the rotative filter 375.

Figure 78A:
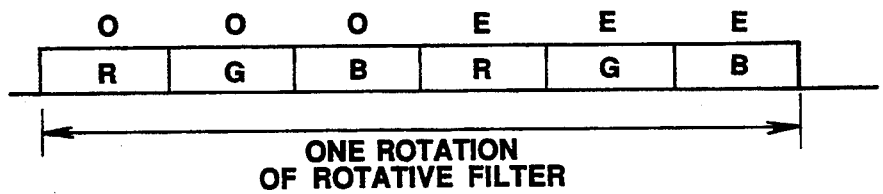
FIGS. 78a, 78b, 78c and 78d are explanatory views relating to reading of a CCD and control of a memory.

In a case of a filter in which R, G and B are sequentially disposed as shown in FIG. 76a, the CCD 370 is driven by the CCD drive circuit 378 to read the image signal from the CCD 370 at timing shown in FIG. 78a. The image signal read from the CCD 370 is A/D-converted, and time sequential R, G and B data items are made simultaneous by the memory 380. The R, G and B data items are D/A-converted so that a video signal is obtained and transmitted.

Figure 78B:
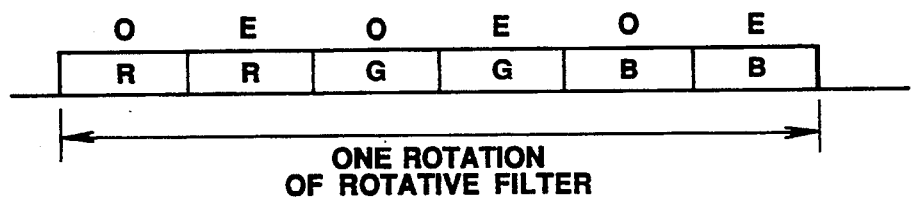
Figure 78C:
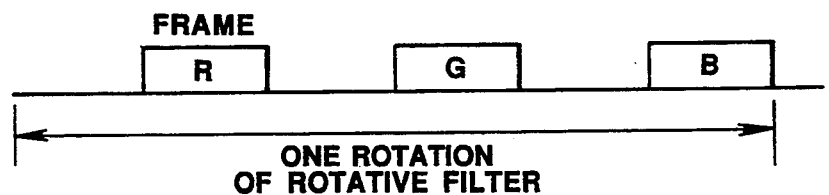
Figure 78D:
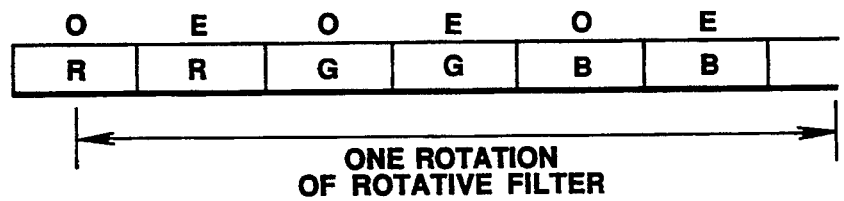

In a case of a filter in which R, G, G, B, and B are disposed as shown in FIG. 76b, the CCD 370 is driven and read at timing shown in FIG. 78b to be made simultaneous data by the memory 380. In a case of a filter in which shields are disposed among R, G and B shown in FIG. 76c, the CCD 370 is driven and read at timing shown in FIG. 78c to be made simultaneous by the memory 380. In a case of a rotative filter shown in FIG. 76b, timing shown in FIG. 78d may be used.

Assuming that imaging is usually performed at a rotational cycle of 20 Hz, the rotational cycle is made slower to 10 Hz or 5 Hz at the time of the imaging operation if the image plane has been darkened excessively to image a subject ordinarily. If the image plane is too bright and therefore the image is undesirably saturated, the rotational cycle is elongated to a speed of 30 Hz or 40 Hz at which reading from the CCD 370 is able to keep up with the timing.

As an example of a means for discriminating the rotational speed of the rotative filter 375, means, as shown in FIGS. 77a and 77b, may be available in which a plurality of rotational speed detection marks 383 are disposed at the outer periphery or the inner periphery of the rotative filter 375. The marks 383 are read by the circuit 377 for discriminating the rotational speed of the rotative filter 375 so that the CCD drive circuit 378 and the memory control circuit 382 are controlled.

The circuit 377 for discriminating the rotational speed of the rotative filter 375 is able to read the rotational speed in accordance with the difference in the quantity of reflected light between the marks 383 and the other portions having no mark.

As described above, this embodiment has the arrangement that, even if the rotational speed of the rotative filter is different, the rotational speed is detected to control the operation of the CCD and writing/reading to and from the memory. Therefore, a normal image can be obtained if the rotational speed of the rotative filter is different.

FIGS. 79 to 82 relate to a twenty-fourth embodiment of the present invention. FIG. 79 is a schematic structural view which illustrates an electronic endoscope apparatus. FIGS. 80a and 80b are structural views which illustrates an aperture in a rotative filter. FIGS. 81a and 81b are a structural views relating to detection of the numerical aperture of the rotative filter. FIG. 82a and 82b are explanatory views relating to reading of the CCD and control of the memory.

The electronic endoscope apparatus according to this embodiment is structured so that the numerical aperture of the rotational filter of the light source is discriminated and the result of the foregoing discrimination is used to change the drive of the CCD and the control of the memory. The same structures and operations as those of the twenty-third embodiment are given the same reference numerals and their descriptions are omitted here. The description will be made about different portions.

The light source portion 372 according to this embodiment has a circuit 385 for discriminating the aperture of the rotative filter 375 in place of the circuit 377 for discriminating the rotational speed of the rotative filter 375 according to the twenty-third embodiment.

Light separated into each color through the rotative filter 375 is applied to a subject via the light guide 369. Light reflected from the subject is imaged by the CCD 370.

Figure 80A:
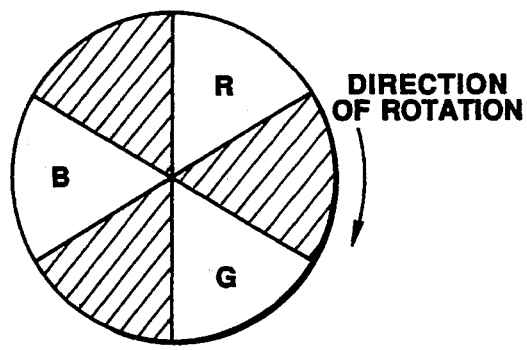
FIG. 80a and 80b are structural views which illustrates a film aperture of the rotative filter.
Figure 82A:
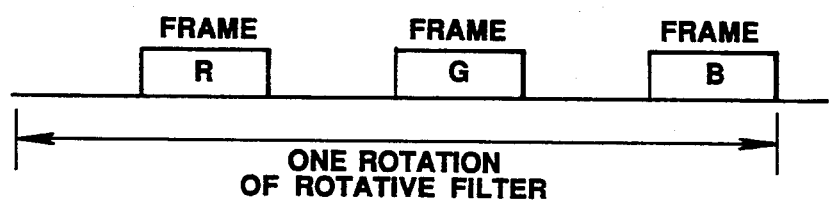
FIG. 82a, 82b and 82c are explanatory views relating to reading of a CCD and control of a memory.
Figure 82B:
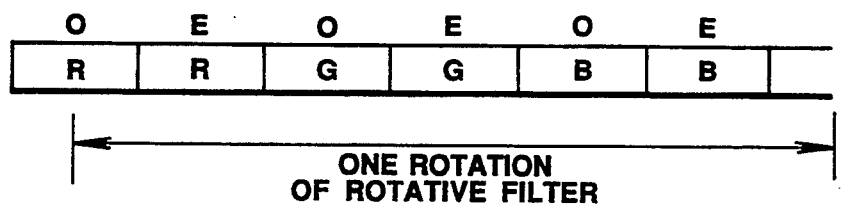
Figure 82C:
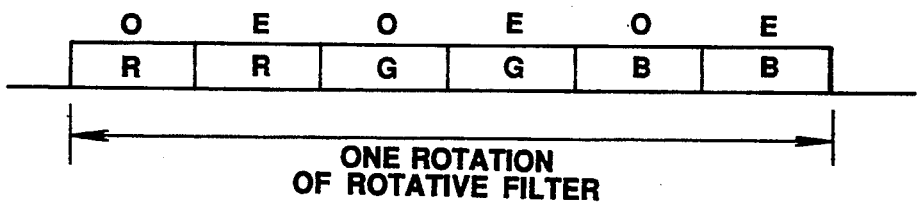

In a case of a filter in which shields are disposed among R, G and B as shown in FIG. 80a, the CCD 370 is driven by a CCD drive circuit 378 to read an image signal from the CCD 370 at timing shown in FIG. 82c. The image signal read from the CCD 370 is A/D-converted, and then time sequential R, G and B data items are made simultaneous by a memory 380. The R, G and B data items are D/A-converted so that a video output is obtained and transmitted.

Figure 80B:
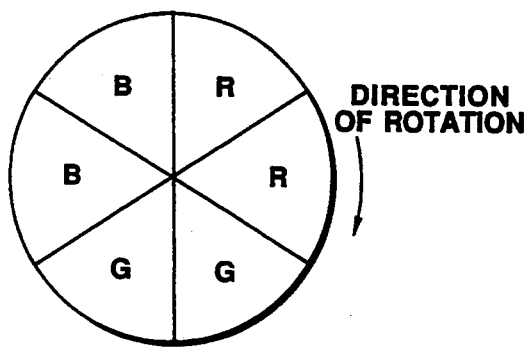

In a case of a filter in which R, R, G, G, B and B are disposed as shown in FIG. 80b, the CCD 370 is driven and read at timing shown in FIG. 82b, and then data is made simultaneous by the memory 380. In a case of a rotative filter shown in FIG. 80a, timing shown in FIG. 82c may be used.

Figure 81A:
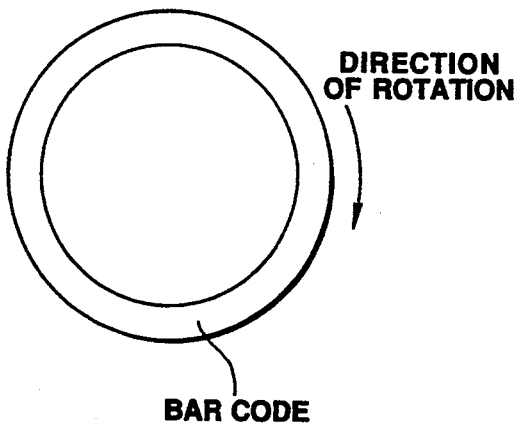
FIG. 81a and 81b are structural views relating to detection of the numerical aperture of the rotative filter.
Figure 81B:
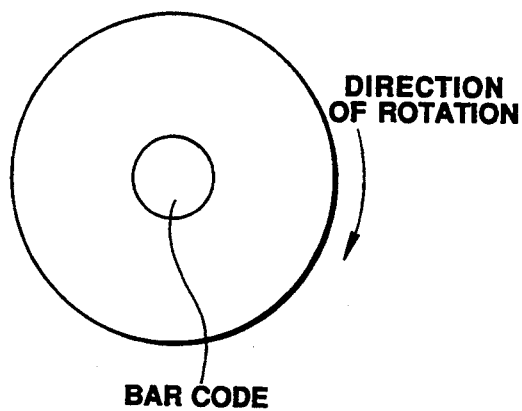

As examples of the structure for discriminating the numerical aperture of the rotative filter are shown in FIG. 81a and 81b in which a bar code is disposed on the outer periphery or the inner periphery of the rotative filter 375 and the bar code is read and discriminated by the circuit 385 for discriminating the aperture of the rotative filter 375. As a result, the drive of the CCD and writing/reading of the memory can be controlled properly.

Since the numerical aperture of the rotative filter is discriminated to automatically control the drive of the CCD and the memory, a proper image freed from undesirable color mixture can be obtained even if a rotative filter having a different numerical aperture is used.

Although an example in which the discrimination is made in accordance with the disposed bar code is described, another arrangement may be employed in which drive is performed as shown in FIG. 82b and whether or not a light shielding portion is detected in accordance with the output from the CCD to make a discrimination.

Figure 83:
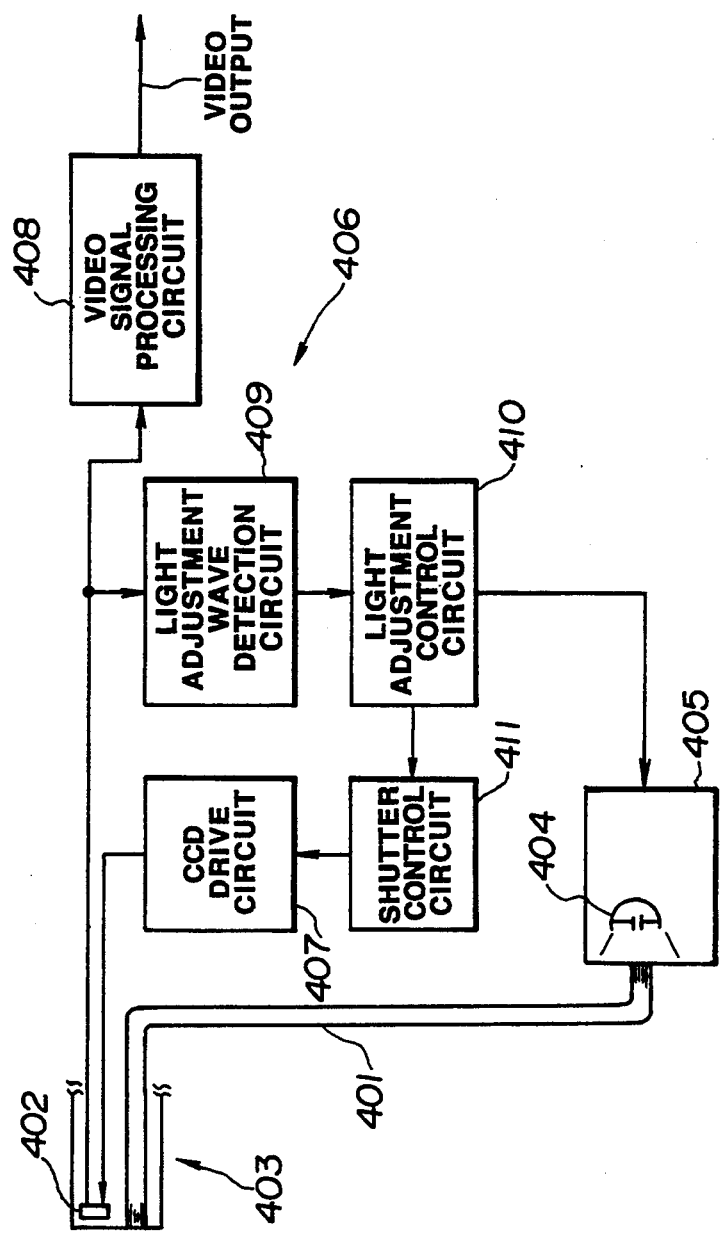
FIG. 83 is a schematic structural view which illustrates an electronic endoscope apparatus according to a twenty-fifth embodiment.

FIG. 83 is a schematic structural view which illustrates an electronic endoscope apparatus according to a twenty-fifth embodiment of the present invention.

The electronic endoscope apparatus according to this embodiment shown in FIG. 83 comprises a light guide 401, an electronic endoscope 403 having a CCD 402 including a color mosaic filter (omitted from illustration) on the imaging surface thereof, a light source portion 405 having a lamp 404 for irradiating a subject with white irradiation light via the light guide 401 and a signal processing portion 406 for driving the CCD 402 and processing an obtained image signal to transmit a video signal.

The foregoing electronic endoscope apparatus is structured so that whether or not the connected light source has a light quantity adjustment means is detected in accordance with an output from the CCD. If a discrimination is made that the light source has no light quantity adjustment means, the drive mode of the CCD is changed to perform light regulation by using a CCD shutter.

Light emitted from the light source portion 405 having no light regulation function is introduced through the light guide 401 so that the subject is irradiated with light. Reflected light from the subject is received by the CCD 402 to be imaged. An output signal from the CCD 402 is driven by the CCD drive circuit 407 and processed by the video signal processing circuit 408 to be transmitted as a video signal.

In a light regulation wave detection circuit 409, the level of the supplied signal of the output from the CCD is wave detected to supply the result of the detection to a light regulation control circuit 410. The light regulation control circuit 410, which has received the result, transmits a light regulation control signal to the light source portion 405 to control the light source portion 405. Since the light source portion 405 has no light regulation function, the quantity of light emitted by the light source is not controlled. Therefore, no change in the signal level corresponding to the light regulation control takes place in the output from the CCD. As a result, the light regulation control circuit 410 discriminates that the light source has no light regulation function and instructs a shutter control circuit 411 to change over the drive mode. The CCD drive circuit 407 controls the time in which the shutter of the CCD 402 is actuated to adjust the exposure quantity of the CCD 402. As result, a proper light regulation is realized so that a normal image is obtained.

This embodiment has the arrangement that the light regulation control signal is supplied to the light source, whether or not the light quantity is changed is discriminated in accordance with the output from the CCD, and, if a discrimination is made that the light source has no light regulation function, the exposure quantity is controlled by the CCD shutter. Therefore, this embodiment enables a normal image to be obtained even if a light source having no light regulation function is connected.

Figure 84:
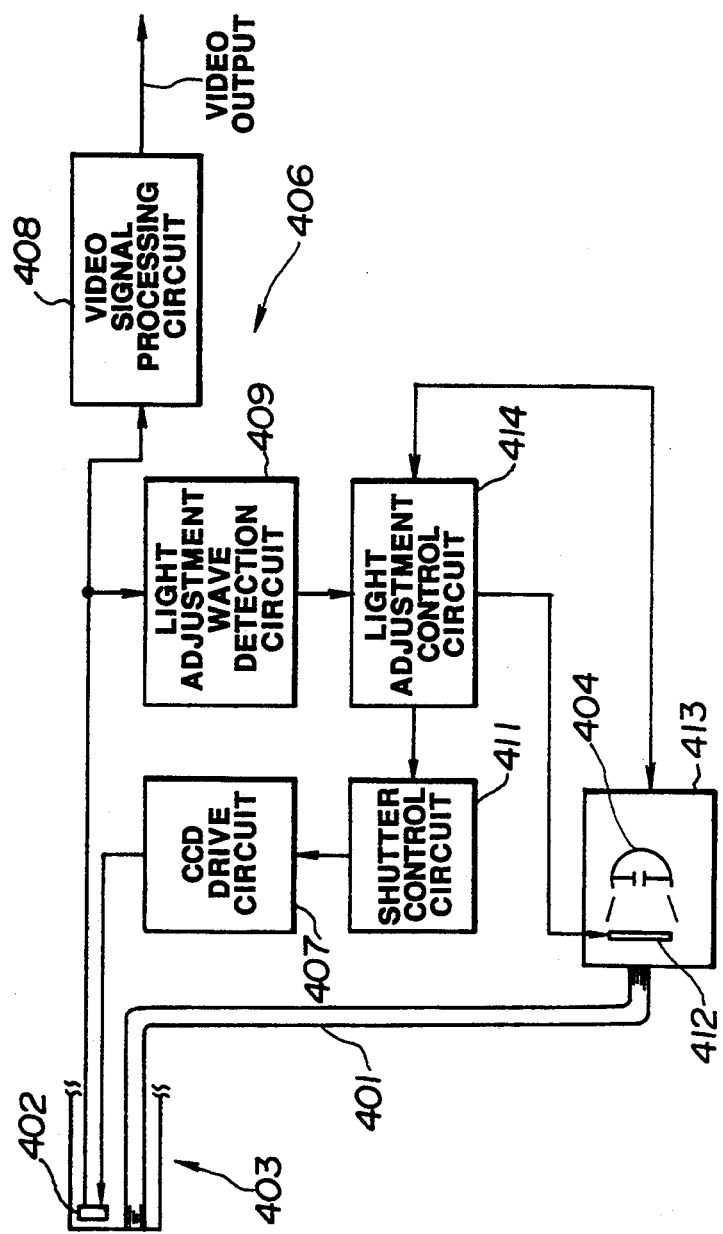
FIG. 84 is a schematic structural view which illustrates an electronic endoscope apparatus according to twenty-sixth embodiment.
Figure 88A:
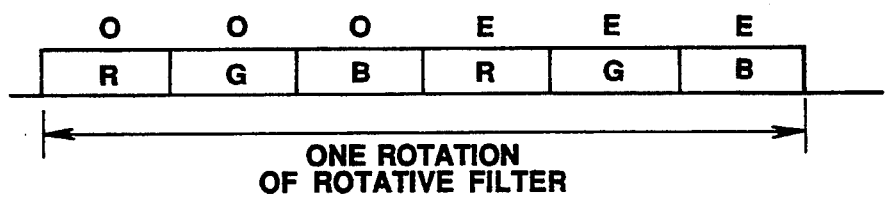
FIG. 88a, 88b, 88c and 88d are explanatory views relating to reading of a CCD and control of a memory.
Figure 88B:
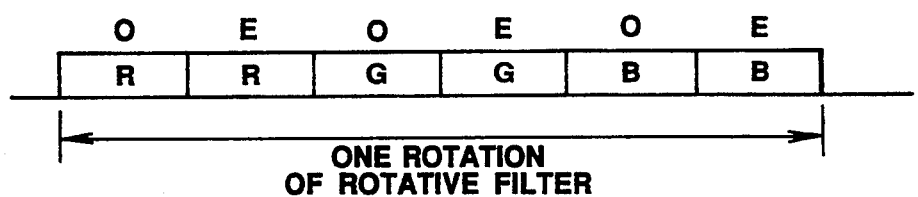
Figure 88C:
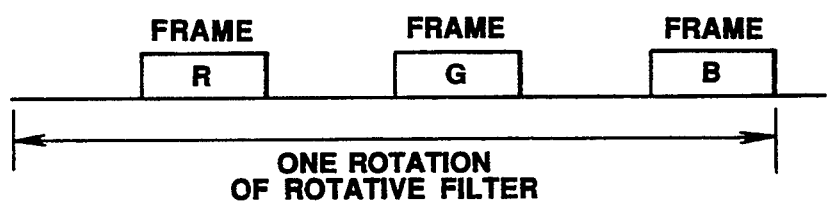
Figure 88D:
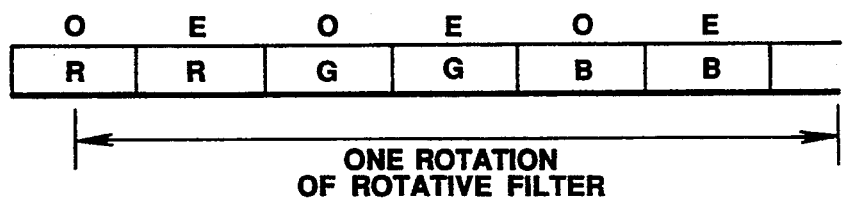

FIG. 84 is a schematic structural view which illustrates an electronic endoscope apparatus according to a twenty-sixth embodiment of the present invention.

The electronic endoscope apparatus according to this embodiment shown in FIG. 84 comprises a light source portion 413 having an arrangement that a diaphragm 412 serving as a light quantity adjustment means is added to the light source portion 405 according to the twenty-fifth embodiment. The diaphragm 412 is so arranged that its diaphragm quantity is controlled by a light regulation control circuit 414 of the signal processing portion 406. The electronic endoscope apparatus according to this embodiment is structured so that the fact that a trans-illumination state has been realized is detected by the light regulation control circuit 414. In accordance with the result of the foregoing detection, change over to light regulation performed by the CCD shutter operated by a shutter control circuit 415 is performed. The same structures and operations as those according to the twenty-fifth embodiment are given the same reference numerals and their descriptions are omitted here.

Light emitted from the light source portion 413 is introduced through the light guide 401 to be applied to a subject. Reflected light from the subject is received by the CCD 402 to be imaged. The CCD 402 is driven by the CCD drive circuit 407 to image the subject.

The light regulation wave detection circuit 409 wave-detect the signal level of the output from the CCD 402 to supply the result to the light regulation control circuit 414. In response to this, the light regulation control circuit 414 supplies a control signal to the diaphragm 412 of the light source to control the diaphragm 412 of the light source. Since the diaphragm 412 of the light source portion 413 is forcibly opened at the time of the trans-illumination, the light regulation control cannot be performed. Therefore, the light regulation control circuit 413, which has received the trans-illumination signal from the light source portion 413, instructs the shutter control circuit 415 to change over the time in which the shutter is opened. The exposure quantity of the CCD 402 is controlled by changing over the time in which the shutter is opened. Since the exposure quantity is controlled by using the CCD shutter at the time of the trans-illumination, a normal image can be obtained.

Although this embodiment has the arrangement that the light regulation control is changed over in response to the trans-illumination signal, the change over may be enabled by discriminating whether or not a reaction takes place in the light regulation control circuit 414 in place of using the trans-illumination signal.

Since this embodiment has the arrangement that the trans-illumination is detected to perform the change over to the light regulation by using the CCD shutter, the saturation of the image can be prevented and, accordingly, a normal image can be obtained.

FIGS. 85 to 88 relate to a twenty-seventh embodiment of the present invention. FIG. 85 is a schematic structural view which illustrates an electronic endoscope apparatus. FIG. 86 is a structural view which illustrates a color configuration of a rotative filter. FIG. 87 is a structural view which illustrates detection of the color configuration of the rotative filter. FIG. 88 is an explanatory view which relates to reading of the CCD and control of the memory.

The electronic endoscope apparatus according to this embodiment shown in FIG. 85 is structured so that the color configuration of the rotative filter is discriminated and the result of the discrimination is used to change the drive of the CCD and the control of the memory. The structures and operations as those of the twenty-third embodiment are given the same reference numerals and their discriminations are omitted here. The discrimination will be made about different portions.

A light source portion 421 according to this embodiment has a circuit 422 for discriminating the color configuration of the rotative filter 375 in place of the circuit 377 for discriminating the rotational speed of the rotative filter 375 according to the twenty-third embodiment.

Light separated into each color by the rotative filter 375 is applied to a subject via the light guide 369, and then reflected light from the subject is imaged by the CCD 370.

FIGS. 86a to 86c illustrate structural examples of the rotative filter 375. In a case of a filter shown in FIG. 86a in which R, G, B, R, G and B are sequentially disposed, the CCD 370 is driven by the CCD drive circuit 378 to read the image signals in the sequential order as G, B, R, G and B, FIG. 88a from the CCD 370. The image signals read from the CCD 370 are A/D-converted, and time sequential R, G and B data items are made simultaneous by the memory 380. By D/A-converting the R, G and B data items, a video output is obtained.

In a case of a filter shown in FIG. 86b in which R, R, G, G, B and B are sequential disposed, the CCD 370 is driven and read in a sequential order as R, R, G, G, B, and B, ..., shown in FIG. 88 (b), and then data items are made simultaneous by the memory 380. In a case of a filter shown in FIG. 86c in which shields are disposed among R, G and B, the CCD 370 is driven and read in a sequential order as R, G and B in an intermittent manner as shown in FIG. 88c because the shields are disposed among the R, G and B. Then, the data items are made simultaneous by the memory 380. In the case of the rotative filter shown in FIG. 86b, timing shown in FIG. 88d may be used.

Examples of the structure for discriminating the color configuration of the rotative filter 375 are shown in FIGS. 84a and 84b in which a bar code is disposed on the outer peripheral or the inner peripheral of the rotative filter 375 and the bar code is read and discriminated by the circuit 422 for discriminating the color configuration of the rotative filter 375. As a result, the drive of the CCD and writing/reading of the memory can properly be controlled.

As described above, this embodiment has the arrangement that the color configuration of the rotative filter is discriminated to automatically control the drive of the CCD and the memory. Therefore, a proper image freed from undesirable color mixture can be obtained even if a rotative filter, in which the color configuration is different, is used.

Figure 89:
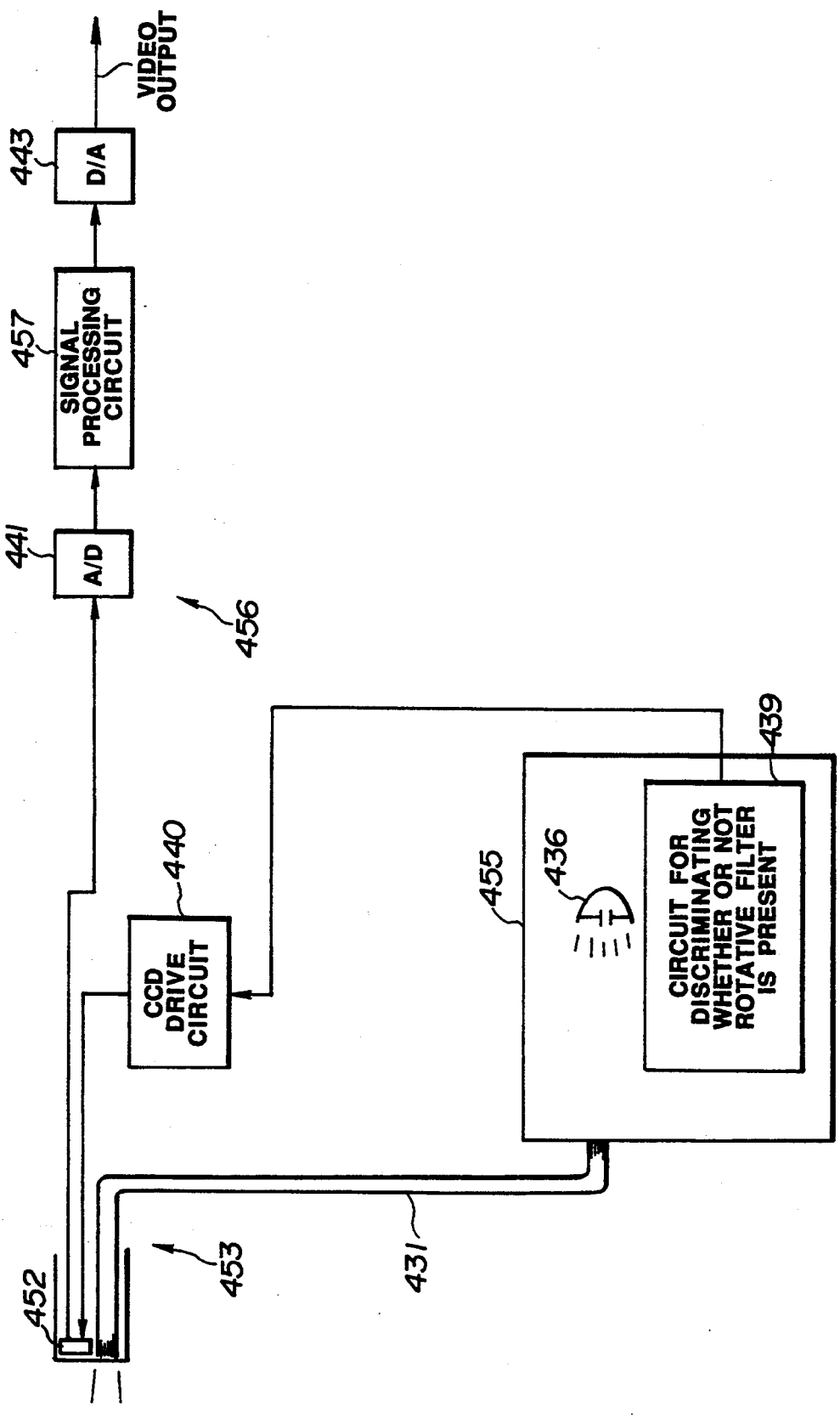
Figure 90:
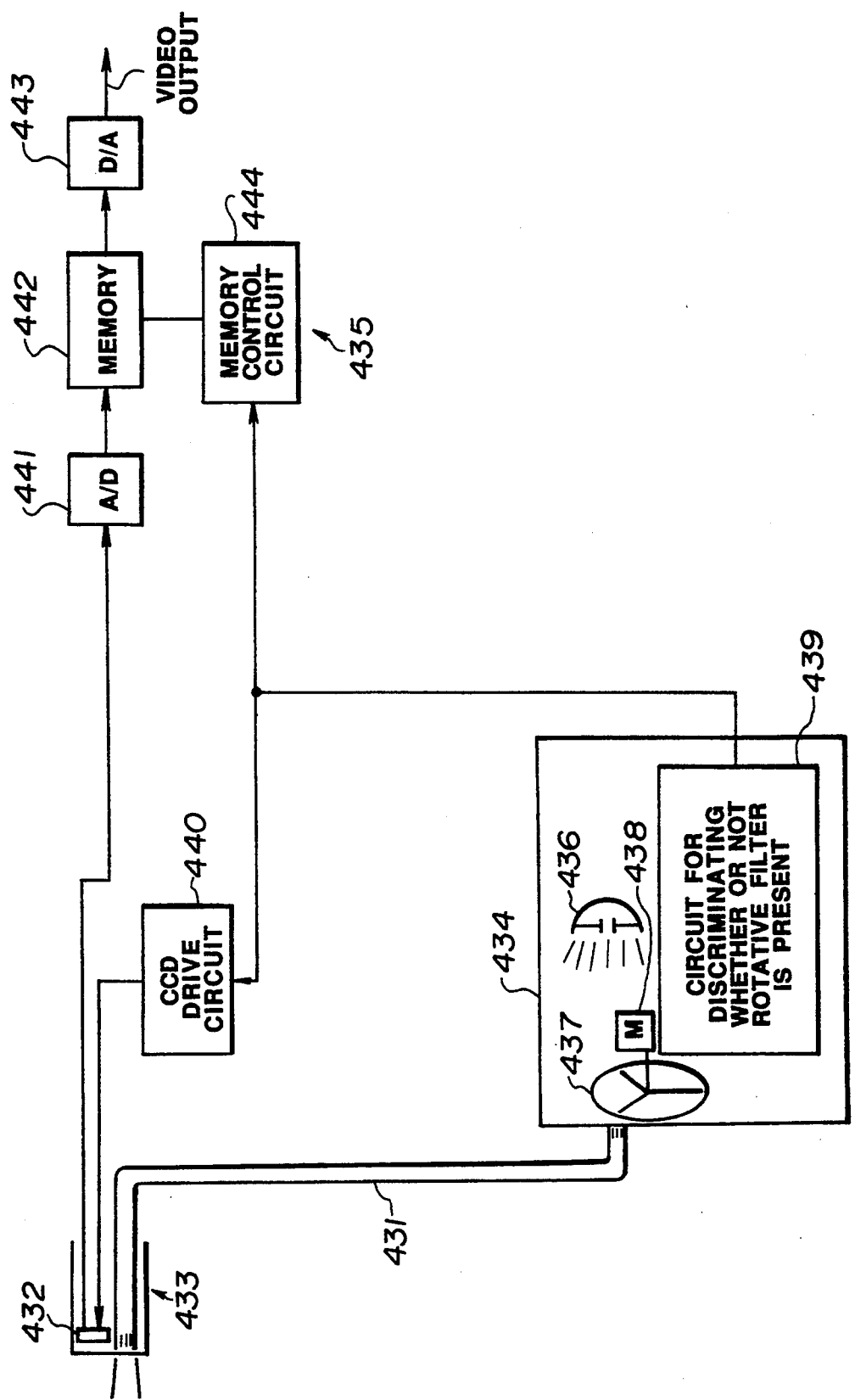
Figure 91:
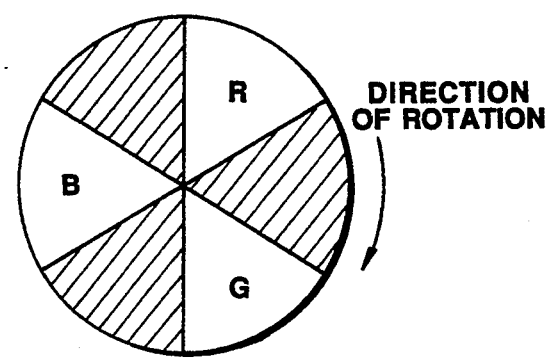

FIGS. 89 to 92 relate to a twenty-eighth embodiment of the present invention. FIG. 89 is a schematic structural view which illustrates an electronic endoscope apparatus having no rotative filter. FIG. 90 is a schematic structural view which illustrates an electronic endoscope apparatus having a rotative filter. FIG. 91 is a structural view which illustrates the rotative filter. FIGS. 92a to 92e are explanatory view which relates to reading of the CCD and control of the memory.

The electronic endoscope apparatus according to this embodiment is structured so that the color configuration of the rotative filter of the light source is discriminated and the result of the discrimination is used to change the drive of the CCD and the control of the memory. The same structures and the operations as those of the twenty-third embodiment are given the same reference numerals and their descriptions are omitted here. The description will be made about only different portions.

The electronic endoscope apparatus according to this embodiment shown in FIGS. 89 and 90 is an apparatus having an arrangement that the light source portion for performing white-light irradiation and a light source portion for performing plane sequential irradiation can be changed over.

The electronic endoscope apparatus according to this embodiment is structured so that whether the light source is the plane sequential irradiation light source or the white light irradiation light source is discriminated, and the result of the discrimination is used to optimally change the drive of the CCD or the like.

The electronic endoscope apparatus according to this embodiment shown in FIG. 90 comprises a light guide 431, an electronic endoscope 433 having a CCD 432, a light source portion 434 for irradiating a subject with plane sequential irradiation light via the light guide 431 and a signal processing portion 435 for processing an obtained image signal to transmit a video signal.

The light source portion 434 shown in FIG. 90 comprises a lamp 436, a rotative filter 437 for separating light emitted by the lamp 436 into time sequential color irradiation light, a motor 438 for rotating the rotative filter 437 and a circuit 439 for discriminating whether or not the rotative filter 437 is present.

Light separated to each color by the rotative filter 432 is applied to a subject via the light guide 431. Reflected light from the subject is received and imaged by the CCD 432.

The CCD 432 is driven by a CCD drive circuit 440 of the signal processing portion 435 to convert the image of the subject into an electric signal. The output from the CCD 432 is A/D-converted by an A/D converter 441 of the signal processing portion 435, made simultaneous by the memory 442 and D/A-converted by a D/A converter 443 to be made a video signal before it is transmitted.

The discrimination signal transmitted from the circuit 439 for discriminating whether or not the rotative filter 437 is present is supplied to a memory control circuit 444 for controlling writing/reading of the memory 442 and to the CCD drive circuit 440.

The electronic endoscope apparatus shown in FIG. 89 comprises a light guide 431, an electronic endoscope 453 having a CCD 452 including a color mosaic filter (omitted from illustration) disposed on the imaging surface thereof and a lamp 436 for irradiating a subject with white irradiation light via the light guide 431. The foregoing electronic endoscope further comprises a light source portion 455 provided with the foregoing circuit 439 for discriminating whether or not the rotative filter 437 is present and a signal processing portion 456 for driving the CCD 452 and processing an obtained image signal to transmit a video signal.

White irradiation light emitted from the light source portion 455 is guided by the light guide 431 to be applied to the subject. Reflected light from the subject is received and imaged by the CCD 452. The CCD 452 is driven by the CCD drive circuit 440 of the signal processing portion 456 to convert the image of the subject into an image signal. The output from the CCD 452 is A/D-converted by an A/D converter 441 of the signal processing portion 456, made simultaneous by a signal processing circuit 457, D/A-converted by the D/A converter 443 to be made a video signal before it is transmitted.

A discrimination signal transmitted from the circuit 439 for discriminating whether or not the rotative filter 437 is present is supplied to the CCD drive circuit 440.

Figure 92A:
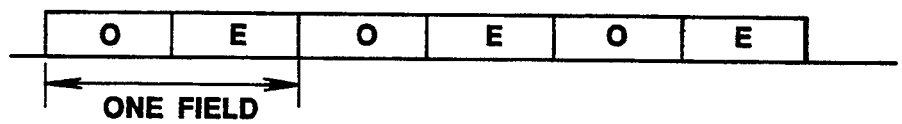
FIGS. 92a, 92b, 92c, 92d and 92e are explanatory views relating to reading of a CCD and control of a memory.
Figure 92B:
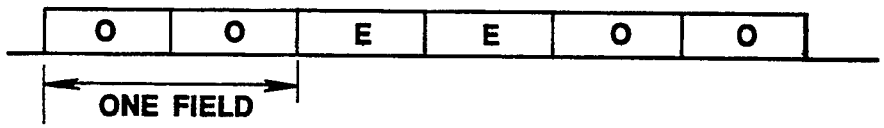

In the case where the light source portion is adapted to the white light irradiation method as shown in FIG. 89, light from the lamp 436 is as it is passed through the light guide 431 to irradiate the subject and image reflected light. If a subject is intended to be imaged while preventing occurrence of blur, the CCD 452 is, as shown in FIG. 92a, driven so that a frame signal is obtained at a halved cycle. In a case where a sufficient dynamic range is intended to be obtained, the same field is read twice as shown in FIG. 92b and they are added. In a case where the operation is intended to be performed to realize an excellent S/N ratio, the drive is performed in a usual manner to read the electric signal.

The electric signal is converted into a digital signal by the A/D converter 441, and then it is processed to be D/A-converted before it is transmitted as a video signal.

In a case where the light source portion is adapted to the plane sequential irradiation method as shown in FIG. 90, light emitted from the lamp 436 is separated by the rotative filter 437 in which shields are disposed among the R, G and B filters as shown in FIG. 91. Light passes through the light guide 431 to be applied to a subject, and reflected light from the subject is imaged by the CCD 432.

Figure 92C:
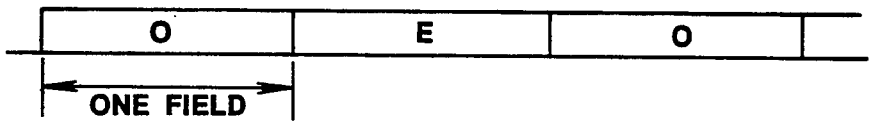
Figure 92D:
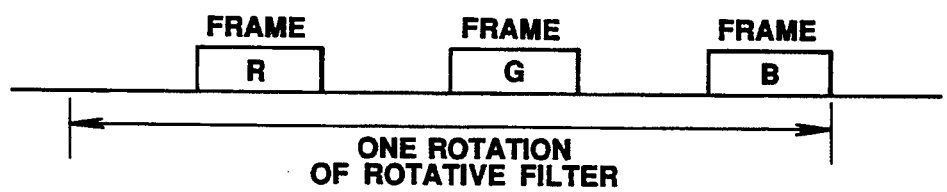
Figure 92E:
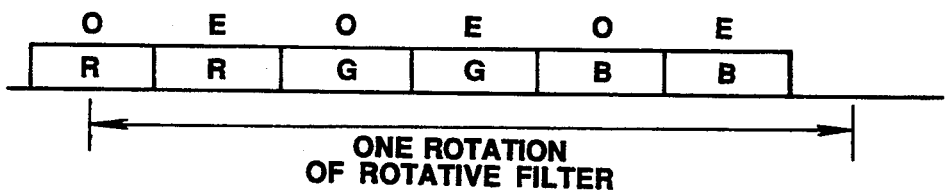

In a case where the CCD 432 is adapted to frame transfer, drive is performed as shown in FIG. 92d. In a case where the CCD 432 is adapted to interline transfer, drive is performed as shown in FIG. 92e. As a result, an electric signal is read from the CCD 432. The electric signal is converted into a digital signal by an A/D converter 441, and then it is made simultaneous by the memory 442 and D/A-converted to be transmitted as a video signal. The change over of the drive method of the CCD 439 is controlled by the circuit 439 for discriminating whether or not the rotative filter 437 is present disposed in the light source portion. If the filter 437 is present, a discrimination is made that the subject method is the plane sequential irradiation method and, accordingly, drive is performed as shown in FIGS. 92d or 92e. If no filter is present, a discrimination is made that the subject method is the white light irradiation method and the change over is performed to perform the drive as shown in FIGS. 92a, 92b or 92c.

Since the discrimination is made whether the light source is adapted to the plane sequential method or the white light method to control the drive of the CCD, an optimum drive method can be selected regardless of the fact that the light source is adapted to the plane sequential method or the white light method.

The structure is arranged such that the circuit for discriminating whether or not the rotative filter is present is provided in the light source portion to discriminate a-fact that the light source is adapted to the plane sequential method or the white light method. However, another structure may be employed in which drive is first performed as shown in FIG. 92a by the white light method to image the subject, and a fact that the read electric signal is changed between odd-number fields and even-number fields by the rotative filter is detected to detect whether or not the rotative filter is present. Also the foregoing structure is able to discriminate that the subject method is the plane sequential method or the white light method. As an alternative to this, the same field may be subjected to a comparison by employing the CCD drive method shown in FIG. 92b.

In each of the foregoing embodiments, the imaging means is not limited to that provided for the endoscope. An external-attachment type TV camera to be connected to the ocular portion of an optical fiber endoscope may be employed.

As many apparently widely different embodiments of this invention may be made without departing from the spirit and scope thereof, it is to be understood that the invention is not limited to the specific embodiments thereof except as defined in the appended claims.

What claimed is:

1. An electronic endoscope apparatus comprising:
   irradiation light generating means for generating irradiation light for irradiating a subject;
   signal processing means for signal-processing an image signal obtained by imaging a subject irradiated with irradiation light;
   information supply means for supplying irradiation light generating means information about said irradiation light generating means; and
   signal processing operation changing means for changing the signal processing operation to be performed by said signal processing means in accordance with irradiation light generating means information supplied from said information supply means.

2. An electronic endoscope apparatus according to claim 1, wherein said information supply means supplies, to said signal processing operation changing means, at least one of information about said irradiation light generating means and information about the operational state of said irradiation light generating means.

3. An electronic endoscope apparatus according to claim 1, wherein said information supply means is irradiation type control means for controlling said irradiation light generating means to change the type of irradiation light, said information supply means supplying, as irradiation light generating means information, a signal to be generated at the time of said control.

4. An electronic endoscope apparatus according to claim 1, wherein said information supply means is irradiation state control means for controlling said irradiation light generating means to change the operational state of said irradiation light generating means, said information supply means supplying, as irradiation light generating means information, a signal to be generated at the time of said control.

5. An electronic endoscope apparatus according to claim 1, wherein said information supply means obtains said irradiation light generating means information by using said image signal.

6. An electronic endoscope apparatus according to claim 1, wherein said information supply means obtains said irradiation light generating means information in accordance with change in a quantity of the drive of drive means for driving said irradiation light generating means.

7. An electronic endoscope apparatus according to claim 1, wherein said information supply means obtains said irradiation light generating means information by identifying identification information items which are different among a plurality of said irradiation light generating means.

8. An electronic endoscope apparatus according to claim 1, wherein said signal processing operation changing means includes a type which causes said signal processing means to change at least one of the brightness level and the color level of said image signal in accordance with said irradiation light generating means information.

9. An electronic endoscope apparatus according to claim 1, wherein said signal processing means includes white balance adjustment means for adjusting the balance of the color level of said image signal, and
   said signal processing operation changing means changes the contents of color level balance adjustment operation to be performed by said white balance adjustment means in accordance with said irradiation light generating means information.

10. An electronic endoscope apparatus according to claim 1, wherein said information supply means obtains said irradiation light generating means information by using a portion of irradiation light generated by said irradiation light generating means.

11. An electronic endoscope apparatus according to claim 10, wherein said information supply means obtains irradiation light generating means information by detecting the color temperature or spectrum energy distribution of irradiation light.

12. An electronic endoscope apparatus according to claim 1, wherein said signal processing operation changing means includes a type which changes the drive mode of said imaging means in accordance with said irradiation light generating means information.

13. An electronic endoscope apparatus according to claim 12, wherein said signal processing operation changing means includes a type which changes the operation for controlling storage means for storing said signal and provided for said signal processing means in accordance with said irradiation light generating means information.

14. An electronic endoscope apparatus according to claim 1, wherein said signal processing means includes automatic gain control means for controlling said image signal to have a predetermined level, and said signal processing operation changing means changes the operational contents of said automatic gain control means for automatically controlling the gain of said signal in accordance with said irradiation light generating means information.

15. An electronic endoscope apparatus according to claim 14, wherein said signal processing operation changing means varies the gain to be realized by said automatic gain control means in accordance with said irradiation light generating means information.

16. An electronic endoscope apparatus according to claim 14, wherein said signal processing operation changing means changes the wave detection method or the wave detection range for automatically controlling the gain of said signal in said automatic gain control means in accordance with said irradiation light generating means information.

17. An electronic endoscope apparatus according to claim 14, wherein said signal processing operation changing means stops said operation for automatically controlling the gain of said image signal to be performed by said automatic gain control means and transmits a signal obtained by maintaining the gain realized immediately before said stop if said irradiation light generating means information is information for notifying that change over to an emergency lamp has been performed.

18. An electronic endoscope apparatus comprising:
irradiation light generating means for generating irradiation light for irradiating a subject;
signal processing means for signal-processing an image signal obtained by imaging a subject irradiated with irradiation light;
irradiation type information supply means for supplying information about the type of said irradiation light generating means; and
signal processing operation changing means for changing the signal processing operation to be performed by said signal processing means in accordance with type information supplied from said irradiation type information supply means.

19. An electronic endoscope apparatus according to claim 18, wherein said signal processing operation changing means changes over the signal processing operation of said signal processing means to be adaptable to the type of said irradiation light generating means in accordance with said type information supplied from said irradiation type information supply means.

20. An electronic endoscope apparatus according to claim 18, wherein said type information supplied from said irradiation type information supply means is information about the irradiation method of irradiation light or the type of irradiation light or whether or not a predetermined function is provided.

21. An electronic endoscope apparatus according to claim 20, wherein said irradiation type information supply means is discrimination means for discriminating the difference occurring in one or more type information items among said type information.

22. An electronic endoscope apparatus according to claim 21, wherein said discrimination means includes a type for discriminating that irradiation light generated by said irradiation light generating means is plane sequential light or white irradiation light or special irradiation light.

23. An electronic endoscope apparatus according to claim 21, wherein said discrimination means includes a type for discriminating whether said irradiation light generating means is set to an irradiation light irradiation method adapted to a single-plate color imaging method or an irradiation light irradiation method adapted to a plane sequential imaging method.

24. An electronic endoscope apparatus according to claim 21, wherein said discrimination means includes a type which discriminates whether said irradiation light generating means emits irradiation light including visible rays or special irradiation light including at least a wavelength region except for the visible rays.

25. An electronic endoscope apparatus according to claim 21, wherein said discrimination means includes a type which discriminates whether or not an automatic light regulation control means for detecting the light quantity of irradiation light to automatically regulate light is provided for said irradiation light generating means.

26. An electronic endoscope apparatus according to claim 24, wherein said special irradiation light emitted by said irradiation light generating means includes infrared rays.

27. An electronic endoscope apparatus according to claim 24, wherein said signal processing means includes white balance adjustment means for adjusting the color level balance of said image signal, and said signal processing operation changing means regenerates and resets the setting of said white balance adjustment means to be adaptable to special irradiation light if said discrimination means has discriminated that said irradiation light generating means is emitting special irradiation light.

28. An electronic endoscope apparatus according to claim 25, wherein said signal processing operation changing means includes a type which performs control to regulate light while changing the mode for driving said imaging means if said discrimination means has discriminated that no automatic light regulation control means for adjusting the light quantity of irradiation light is provided.

29. An electronic endoscope apparatus comprising:
irradiation light generating means for generating irradiation light for irradiating a subject;
signal processing means for signal-processing an image signal obtained by imaging a subject irradiated with irradiation light;
operational state information supply means for discriminating the operational state of said irradiation light generating means for generating irradiation light to supply information about the operational state of said irradiation light generating means; and
signal processing operation changing means for changing the signal processing operation to be performed by said signal processing means in accordance with said information about the operational state of said irradiation light generating means supplied from said operational state information supply means.

30. An electronic endoscope apparatus according to claim 29, wherein said signal processing operation changing means changes over the signal processing operation to be performed by said signal processing means to be adaptable to said irradiation light generating means in accordance with said operational state information supplied from said operational state information supply means.

31. An electronic endoscope apparatus according to claim 29, wherein said operational state information supply means is discrimination means for discriminating an error or the quantity of deviation of the state of said irradiation light generating means from a standard state.

32. An electronic endoscope apparatus according to claim 31, wherein said discrimination means includes a type which discriminates the light quantity of the irradiation light source or said irradiation light generating means or the color distribution of irradiation light.

33. An electronic endoscope apparatus according to claim 31, wherein said discrimination means includes a type which detects the quantity of deviation in the optical axis between light quantity adjustment means and irradiation light.

34. An electronic endoscope apparatus according to claim 31, wherein said discrimination means includes a type which discriminates dispersion in the spectrum characteristics among wavelength region separation means for separating irradiation light emitted by said irradiation light generating means into a plurality of difference wavelength regions.

35. An electronic endoscope apparatus according to claim 29, wherein said operational state information supply means is discrimination means for discriminating whether or not the state of said irradiation light generating means is abnormal.

36. An electronic endoscope apparatus according to claim 35, wherein said discrimination means includes a type which detects a fact that the irradiation light source of said irradiation light generating means has been changed over from a usual lamp to an emergency lamp.

37. An electronic endoscope apparatus according to claim 36, wherein said discrimination means includes a type which discriminates a fact that change over to an emergency lamp has been performed in accordance with change in the electric current to be supplied to the irradiation light source of said irradiation light generating means.

38. An electronic endoscope apparatus according to claim 36, wherein said discrimination means includes a type which detects fall of the color temperature in accordance with an electric signal supplied from said imaging means to discriminate that change over to an emergency lamp has been performed.

39. An electronic endoscope apparatus according to claim 36, wherein said signal processing means includes white balance adjustment means for adjusting the color level balance of said image signal, and
said signal processing operation changing means includes a type which varies setting of an initial value of said white balance adjustment means if said discrimination means has detected that said irradiation light source has been changed over to said emergency lamp so that said setting can be adapted to the characteristics of said emergency lamp.

40. An electronic endoscope apparatus according to claim 36, wherein said signal processing means includes white balance adjustment means for adjusting the color level balance of said image signal, and
said signal processing operation changing means includes a type which changes the gain of said automatic gain control means if said discrimination means has detected that said usual lamp has been changed over to said emergency lamp.

41. An electronic endoscope apparatus according to claim 35, wherein said discrimination means includes a type which detects an abnormal state generated due to aging of said irradiation light generating means.

42. An electronic endoscope apparatus according to claim 41, wherein said discrimination means includes a type which detects change in the light quantity of the irradiation light source of said irradiation light generating means.

43. An electronic endoscope apparatus according to claim 42, wherein said signal processing operation changing means includes a type which varies the drive mode of said imaging means to correspond to the difference in the configuration of a plurality of filters provided for a rotative filter detected by said discrimination means.

44. An electronic endoscope apparatus according to claim 42, wherein said signal processing means includes an automatic gain control means for controlling said image signal to have a predetermined level, and
said signal processing operation changing means varies the gain of said automatic gain control means to correspond to the change in the light quantity of said irradiation light source of said irradiation light generating means detected by said discrimination means.

45. An electronic endoscope apparatus according to claim 42, wherein said signal processing means includes an automatic gain control means to control said image signal to have a predetermined level,
said discrimination means includes detection means for receiving a portion of irradiation light to detect the light quantity of said irradiation light source, and
said signal processing operation changing means performs control to raise the gain of said automatic gain control means if said detection means has detected that the light quantity of said irradiation light source has been reduced.

46. An electronic endoscope apparatus according to claim 45, wherein said signal processing means includes means for highlighting the outline of said image of said subject, and
said signal processing operation changing means includes a type which performs control to restrict the outline highlighting level realized by said means for highlighting said outline to be low if said detection means has detected that the light quantity of said irradiation light source has been reduced.

47. An electronic endoscope apparatus according to claim 45, wherein said signal processing means includes means for highlighting the chromaticity among image information of said subject, and
said signal processing operation changing means includes a type which performs control to restrict the highlighting level of said chromaticity realized by said means for highlighting said chromaticity to be low if said detection means has detected that said light quantity of said irradiation light source has been reduced.

48. An electronic endoscope apparatus according to claim 29, wherein said operational state information supply means is discrimination means for discriminating the state of said irradiation light generating means among a plurality of usual states.

49. An electronic endoscope apparatus according to claim 48, wherein said plurality of usual states to be discriminated by said discrimination means are at least one of irradiation state of said light source of said irradiation light generating means and the state of said light quantity adjustment means for adjusting the light quantity of irradiation light generated by said irradiation light generating means.

50. An electronic endoscope apparatus according to claim 48, wherein said discrimination means detects the difference in the configuration of a plurality of filters provided for a rotative filter for time-sequentially separating irradiation light generated by said irradiation light generating means into a plurality of wavelength regions.

51. An electronic endoscope apparatus according to claim 48, wherein said irradiation light generating means includes automatic light regulation control means for adjusting the light quantity of irradiation light, and said signal processing operation changing means includes a type which changes over the wave detection method for obtaining a control signal for controlling the gain of said automatic light regulation control means in accordance with the irradiation mode of said irradiation light generating means discriminated by said discrimination means.

52. An electronic endoscope apparatus according to claim 48, wherein said discrimination means includes a type which discriminates whether or not said irradiation light generating means is in a trans-illumination state.

53. An electronic endoscope apparatus according to claim 52, wherein said signal processing operation changing means includes a type which performs control to regulate light while changing the drive mode of said imaging means if said discrimination means has discriminated that a trans-illumination state has been realized.

54. An electronic endoscope apparatus according to claim 48, wherein said discrimination means detects the difference in the rotational speed of a rotative filter for time-sequentially separating irradiation light generated by said irradiation light generating means into a plurality of wavelength regions.

55. An electronic endoscope apparatus according to claim 54, wherein said signal processing means includes a type which varies the drive mode of said imaging means to correspond to the difference in the rotational speed of said rotative filter detected by said discrimination means.

56. An electronic endoscope apparatus according to claim 48, wherein said discrimination means detects the difference in the numerical aperture among a plurality of filters provided for a rotative filter for time-sequentially separating irradiation light generated by said irradiation light generating means into a plurality of wavelength regions.

57. An electronic endoscope apparatus according to claim 56, wherein said signal processing operation changing means includes a type which varies the drive mode of said imaging means to correspond to the difference in the numerical aperture of said rotative filter detected by said discrimination means.

58. An electronic endoscope apparatus according to claim 48, wherein said discrimination means includes a type which discriminates the adjustment state of said light quantity adjustment means for adjusting the light quantity of irradiation light.

59. An electronic endoscope apparatus according to claim 58, wherein said signal processing means includes white balance adjustment means for adjusting the color level balance of said image signal, and said signal processing operation changing means includes a type which varies setting of said white balance adjustment means to be adaptable to an adjustment state of said light quantity adjustment means detected by said discrimination means.

60. An electronic endoscope apparatus according to claim 58, wherein said signal processing operation changing means performs control to cause said signal processing means to vary the color level of said image signal if said discrimination means has discriminated that the light quantity limitation of said light quantity adjustment means is larger than a predetermined value.

61. An electronic endoscope apparatus according to claim 48, wherein said discrimination means includes a type which discriminates the difference in the irradiation mode of said irradiation light generating means.

62. An electronic endoscope apparatus according to claim 61, wherein said discrimination means discriminates whether the mode is a continuous irradiation mode or a flash irradiation mode.

63. An electronic endoscope apparatus according to claim 62, wherein said signal processing means includes automatic gain control means for controlling said image signal to have a predetermined level and means for generating a still image of said subject, and said signal processing operation changing means includes a type which stops the control operation to be performed by said automatic gain control means and maintains the gain realized immediately before said stoppage if said discrimination means has discriminated that the mode is said flash irradiation mode when control is so performed that said signal processing means processes said signal in a still image mode.

64. An electronic endoscope apparatus according to claim 62, wherein said signal processing means includes automatic gain control means for controlling said image signal to have a predetermined level and means for generating a still image of said subject, and said signal processing operation changing means includes a type which changes the detection range for obtaining a signal to control the gain of said automatic gain control means if said discrimination means has discriminated that the mode is said flash irradiation mode when control is so performed that said signal processing means processes said signal in said still image mode.

65. An electronic endoscope apparatus according to claim 61, wherein said discrimination means discriminates whether the mode is a white light irradiation mode or a plane sequential irradiation mode.

66. An electronic endoscope apparatus according to claim 65, wherein said signal processing operation changing means includes a type which varies the drive mode of said imaging means to be adaptable to the irradiation mode discriminated by said discrimination means.

67. An electronic endoscope apparatus according to claim 65, wherein said signal processing means includes white light irradiation mode signal processing means for signal-processing an image signal obtained by said imaging means under white light irradiation and plane sequential irradiation mode signal processing means for signal-processing an image signal obtained by said imaging means under plane sequential irradiation light, and said signal processing operation changing means is selection means which selects said white light irradiation mode signal processing means or said plane sequential irradiation mode signal processing means to be adaptable to the irradiation mode of said irradiation light generating means discriminated by said discrimination means.

68. An electronic endoscope apparatus according to claim 65, wherein said signal processing means includes white balance adjustment means for adjusting the color level balance of said image signal, and said signal processing operation changing means includes a type which varies setting of said white balance adjustment means to be adaptable to the spectrum characteristics of a color mosaic filter disposed on the imaging surface of imaging means to be used in said white light irradiation mode if said discrimination means has discriminated that the mode is said white light irradiation mode, and which varies setting of said white balance adjustment means to be adaptable to the spectrum characteristics of a rotative filter for separating irradiation light emitted from said irradiation light generating means to be used in said plane sequential irradiation mode into a plurality of wavelength regions if said discrimination means has discriminated that the mode is said plane sequential irradiation mode.

69. An electronic endoscope apparatus comprising:
irradiation light generating means for, in accordance with a predetermined function, generating irradiation light for irradiating a subject;
signal processing means for signal-processing an image signal obtained by imaging said subject irradiated with irradiation light;
function information detection means for detecting information about said predetermined function possessed by said irradiation light generating means; and
signal processing operation changing means for changing the signal processing operation to be performed by said signal processing means in accordance with said function information detected by said function information detection means.

70. An electronic endoscope apparatus according to claim 69, wherein said signal processing operation changing means changes over the signal processing operation to be performed by said signal processing means to be adaptable to the function of said irradiation light generating means in accordance with information supplied by said function information supply means.

71. An electronic endoscope apparatus according to claim 69, wherein said irradiation light generating means has a predetermined function for changing the generation state of irradiation light.

72. An electronic endoscope apparatus according to claim 69, wherein said irradiation light generating means is composed of a plurality of irradiation light generating means having different functions.

73. An electronic endoscope apparatus comprising:
irradiation light generating means for generating irradiation light for irradiating a subject;
irradiation type information supply means for supplying irradiation type information about the type of irradiation light generated by said irradiation light generating means;
signal processing means for signal-processing an image signal obtained by imaging a subject irradiated with irradiation light, said signal processing means having a signal changing structure at least a portion of which is selectively changeable; and
signal processing function changing means for instructing, in accordance with said irradiation type information supplied by said irradiation type information supply means, at least a portion of said structure of said signal processing means for processing said signal to be selectively changed to change said signal processing operation.

74. An electronic endoscope apparatus according to claim 73, wherein said at least a portion of said structure of said signal processing means for processing said signal is constituted by a field programmable gate array.

75. An electronic endoscope apparatus according to claim 73, wherein said signal processing means is arranged so that a plurality of different processing means for performing different processing operations are disposed in parallel, and
said irradiation type information supply means is selection means for selecting processing means from said plurality of different processing means that is adaptable to the type of irradiation light which is being applied in accordance with said irradiation type information supplied by said irradiation type information supply means.

76. An electronic endoscope apparatus comprising:
irradiation light generating means for generating irradiation light for irradiating a subject;
signal processing means for signal-processing an image signal obtained by imaging said subject with irradiation light and structured such that at least a portion of said signal processing operation can be adjusted;
irradiation light generation state detection means for detecting an irradiation light generation state of said irradiation light generating means; and
signal processing operation changing means for changing said signal processing operation by adjusting the operational state of said signal processing means in accordance with the result of said detection performed by said irradiation light generation state detection means.

* * * * *